United States Patent
Fischer et al.

(10) Patent No.: US 8,258,267 B2
(45) Date of Patent: Sep. 4, 2012

(54) HUMAN ANTI-IP-10 ANTIBODIES USES THEREOF

(75) Inventors: Nicolas Fischer, Geneva (CH); Marie Kosco-Vilbois, Minzier (FR); Olivier Leger, St. Sixt (FR)

(73) Assignee: NovImmune S.A., Geneva (CH)

( * ) Notice: Subject to any disclaimer, the term of this patent is extended or adjusted under 35 U.S.C. 154(b) by 192 days.

(21) Appl. No.: 12/529,124

(22) PCT Filed: Feb. 28, 2008

(86) PCT No.: PCT/US2008/002650
§ 371 (c)(1), (2), (4) Date: Aug. 25, 2010

(87) PCT Pub. No.: WO2008/106200
PCT Pub. Date: Sep. 4, 2008

(65) Prior Publication Data
US 2010/0322941 A1 Dec. 23, 2010

Related U.S. Application Data

(60) Provisional application No. 60/904,265, filed on Feb. 28, 2007.

(51) Int. Cl.
A61K 39/395 (2006.01)
A61K 39/40 (2006.01)
C07K 17/00 (2006.01)

(52) U.S. Cl. ............... 530/387.1; 530/387.3; 530/388.1; 530/388.15; 530/388.23; 530/388.85; 424/130.1; 424/133.1; 424/141.1; 424/142.1; 424/158.1

(58) Field of Classification Search .................. None
See application file for complete search history.

(56) References Cited

U.S. PATENT DOCUMENTS

| 2003/0166589 A1 | 9/2003 | Karin | 514/44 |
|---|---|---|---|
| 2004/0096446 A1 | 5/2004 | Lane | 424/145.1 |
| 2004/0191255 A1 | 9/2004 | Lillard et al. | 424/145.1 |
| 2005/0025744 A1 | 2/2005 | Lane | 424/85.6 |
| 2005/0191293 A1 | 9/2005 | Deshpande et al. | 424/143.1 |
| 2008/0019973 A1 | 1/2008 | Lane et al. | 424/145.1 |
| 2008/0063646 A1 | 3/2008 | Balasa et al. | 424/158.1 |
| 2009/0081787 A1 | 3/2009 | Yoneyama et al. | 435/375 |

FOREIGN PATENT DOCUMENTS

| WO | WO 02/15932 | 2/2002 |
|---|---|---|
| WO | WO 02/098346 | 12/2002 |
| WO | WO 03/006045 | 1/2003 |
| WO | WO 2004/045525 | 6/2004 |
| WO | WO 2004/082714 | 9/2004 |
| WO | WO 2004/101511 | 11/2004 |
| WO | WO 2005/023201 | 3/2005 |
| WO | WO 2005/058815 | 6/2005 |
| WO | WO 2005/060457 | 7/2005 |
| WO | WO 2006/118085 | 11/2006 |
| WO | WO 2008/044824 | 4/2008 |

OTHER PUBLICATIONS

Arai et al., "IP-10 and Mig Facilitate Accumulation of T Cells in the Virus-Infected Liver," Cellular Immunol., vol. 219:48-56 (2002).
Christen et al., "Among CXCR3 Chemokines, IFN-gamma-Inducible Protein of 10 kDa (CXC Chemokine Ligand (CXCL) 10) but not Monokine Induced by IFN-gamma (CXCL9) Imprints a Pattern for the Subsequent Development of Autoimmune Disease," J. of Immunol., vol. 171:6838-6845 (2003).
Chothia et al., "Conformations of immunoglobulin hypervariable regions," Nature, vol. 342:877-883 (1989).
Dufour et al,, "INF-gamma-Inducible Protein 10 (IP-10; CXCL10)-Deficient Mice Reveal a Role for IP-10 in Effector T Cell Generation and Trafficking," J. of Immunol., vol. 168:3195-3204 (2002).
Liu et al, "Chemokine Receptor CXCR3: An Unexpected Enigma," Current Topics in Developmental Biology, vol. 68:149-181 (2005).
Liu et al., "Neutralization of the Chemokine CXCL10 Reduces Inflammatory Cell Invasion and Demyelination and Improves Neurological Function in a Viral Mode of Multiple Sclerosis," J. of Immunol., vol. 167: 4091-4097 (2001).
Tannenbaum et al., "The CXC Chemokines IP-10 and Mig are Necessary for IL-12-Mediated Regression of the Mouse RENCA Tumor," J. of Immunol, vol. 161:927-932 (1998).

*Primary Examiner* — Chun Dahle
(74) *Attorney, Agent, or Firm* — Mintz Levin Cohn Ferris Glovsky and Popeo, P.C.; Ivor R. Elrifi

(57) ABSTRACT

The invention relates to fully human antibodies, and fragments thereof, that bind to interferon-inducible-protein-10 (IP-IO, CXCL1O), thereby modulating the interaction between IP-IO and its receptor, CXCR3, and/or modulating the biological activities of IP-IO. The invention also relates to the use of such anti-IP-10 antibodies in the prevention or treatment of immune-related disorders and in the amelioration of one or more symptoms associated with an immune-related disorder.

7 Claims, 13 Drawing Sheets

Fig. 10

HUMAN ANTI-IP-10 ANTIBODIES USES THEREOF

RELATED APPLICATIONS

This patent application is a national stage application, filed under 35 U.S.C. §371, of International Application No. PCT/US2008/002650, filed on Feb. 28, 2008, which claims the benefit of and priority to U.S. Provisional Patent Application Ser. No. 60/904,265, filed Feb. 27, 2007, each of which is herein incorporated by reference in its entirety.

INCORPORATION-BY-REFERENCE OF SEQUENCE LISTING

The contents of the text file named "412NATLSeqList.txt", which was created on Feb. 19, 2010 and is 90.6 KB in size, are hereby incorporated by reference in their entirety.

FIELD OF THE INVENTION

This invention relates generally to fully human anti-IP-10 monoclonal antibodies as well as to methods for use thereof.

BACKGROUND OF THE INVENTION

Interferon-inducible protein-10 (IP-10, CXCL10) is a CXC chemokine that signals through the CXCR3 receptor. IP-10 selectively chemoattracts Th1 lymphocytes and monocytes, and inhibits cytokine-stimulated hematopoietic progenitor cell proliferation. IP-10 was originally identified as an IFN-g-inducible gene in monocytes, fibroblasts and endothelial cells. It has since been shown that IP-10 mRNA is also induced by LPS, IL-1b, TNF-a, IL-12 and viruses. Additional cell types that have been shown to express IP-10 include activated T-lymphocytes, splenocytes, keratinocytes, osteoblasts, astrocytes and smooth muscle cells.

Elevated levels of IP-10 expression has been implicated in a variety of diseases and disorders. Accordingly, there exists a need for therapies that target IP-10 activity.

SUMMARY OF THE INVENTION

The present invention provides fully human monoclonal antibodies that specifically bind interferon inducible protein 10 (IP-10, also referred to herein as CXCL10). Exemplary monoclonal antibodies include NI-0801; CF1N1R3P4_C7 ("C7"); CF1H1R3P3_G11 ("G11"); CF1H1R3P4_B5 ("B5"); CF1A11R3P3_F3 ("F3"); CC21R3P1_F1 ("CC_F1"); CB21R3P3_E5 ("E5"); CC21R3P1_H6 ("H6"); CC21R3P5_C5 ("C5"); CB1R3P4_D3 ("D3"); CB2R2P4_C3 ("C3"); CC21R3P4_F4 ("F4"); CC21R3P1_C1a ("C1a"); CC21R3P3_C1 ("C1"); CC21R3P1_E7 ("E7"); CE7C1R3H8_J9 ("J9"); CB21R3P1_F1 ("CB_F1"); CC21R3P1_A2 ("A2"); CB21R3P6_G7 ("G7"); and CC21R3P1_B9 ("B9").

Alternatively, the monoclonal antibody is an antibody that binds to the same epitope as NI-0801, C7, G11, B5, F3, CC_F1, E5, H6, C5, D3, F4, C1a, C1, E7, J9, CB_F1, A2, G7, C3, or B9. The antibodies are respectively referred to herein as huIP-10 antibodies.

huIP-10 antibodies of the invention also include antibodies that include a heavy chain variable amino acid sequence that is at least 90%, 92%, 95%, 97%, 98%, 99% or more identical the amino acid sequence of SEQ ID NO: 2, 12, 18, 26, 31, 41, 51, 54, 61, 68, 75, 83, 92, 102, 109, 116, 123 or 137 and/or a light chain variable amino acid that is at least 90%, 92%, 95%, 97%, 98%, 99% or more identical the amino acid sequence of SEQ ID NO: 4, 14, 23, 28, 33, 43, 56, 63, 70, 77, 85, 94, 104, 111, 118, 125, 139 or 145.

Preferably, the three heavy chain complementarity determining regions (CDRs) include an amino acid sequence at least 90%, 92%, 95%, 97%, 98%, 99% or more identical to each of: (i) a VH CDR1 sequence selected from the group consisting of SEQ ID NOs: 5, 34, 44, 64, 86, 95 and 127; (ii) a VH CDR2 sequence selected from the group consisting of SEQ ID NOs: 6, 15, 35, 45, 65, 87, 96 and 128; (iii) a VH CDR3 sequence selected from the group consisting of SEQ ID NOs: 7, 21, 36, 46, 52, 57, 66, 78, 88, 97, 105, 129, 132 and 140; and a light chain with three CDR that include an amino acid sequence at least 90%, 92%, 95%, 97%, 98%, 99% or more identical to each of (iv) a VL CDR1 sequence selected from the group consisting of SEQ ID NOs: 8, 16, 37, 47, 71, 79, 98, 106, 112, 119, 133 and 141; (v) a VL CDR2 sequence selected from the group consisting of SEQ ID NOs: 9, 38, 48, 58, 72, 80, 89, 99, 113, 120 and 142; and (vi) a VL CDR3 sequence selected from the group consisting of SEQ ID NOs: 10, 24, 29, 39, 49, 59, 73, 81, 90, 100, 107, 114, 121, 126 and 143.

In one embodiment, the huIP-10 antibodies of the invention include a variable heavy chain region comprising the amino acid sequence of SEQ ID NO:2 and a light chain variable region comprising the amino acid sequence of SEQ ID NO:4.

The huIP-10 antibodies of the invention include a $V_H$ CDR1 region comprising the amino acid sequence of SEQ ID NO: 5, a $V_H$ CDR2 region comprising the amino acid sequence of SEQ ID NO:6; and a $V_H$ CDR3 region comprising the amino acid sequence of SEQ ID NO:7. The huIP-10 antibodies include a $V_L$ CDR1 region comprising the amino acid sequence of SEQ ID NO: 8; a $V_L$ CDR2 region comprising the amino acid sequence of SEQ ID NO:9; and a $V_L$ CDR3 region comprising the amino acid sequence of SEQ ID NO: 10. In a preferred embodiment, the huIP-10 antibody includes a $V_H$ CDR1 region comprising the amino acid sequence of SEQ ID NO: 5, a $V_H$ CDR2 region comprising the amino acid sequence of SEQ ID NO:6; a $V_H$ CDR3 region comprising the amino acid sequence of SEQ ID NO:7, a $V_L$ CDR1 region comprising the amino acid sequence of SEQ ID NO: 8; a $V_L$ CDR2 region comprising the amino acid sequence of SEQ ID NO:9; and a $V_L$ CDR3 region comprising the amino acid sequence of SEQ ID NO: 10.

Preferably, the huIP-10 antibodies are formatted in an IgG isotype. More preferably, the huIP-10 antibodies are formatted in an IgG1 isotype. An exemplary IgG1-formatted antibody is the IgG1-formatted NI-0801 antibody comprising the heavy chain sequence of SEQ ID NO: 135 and the light chain sequence of SEQ ID NO:134, as shown below:

```
>NI-0801 Light Chain Amino Acid Sequence
                                       (SEQ ID NO: 134)
NFMLTQPHSVSESPGKTVTISCTGSGGSIASNYVQWYQQRPGSSPTTVIY

EDNQRPSGVPDRFSGSIDSSSNSASLTISGLKTEDEADYYCQSYDPLPVW

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS
```

-continued

>NI-0801 Heavy Chain Amino Acid Sequence
(SEQ ID NO: 135)
QVQLVESGGGVVQPGRSLRLSCAASGFTFSNSGIHWVRQAPGKGLEWVAV

ISYDGSNKYYADSVKGRFTISRDNSKNTLYLQMNSLRAEDTAVYYCARLR

DNAEYTDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKRVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

The closest germline for the huIP-10 antibodies described herein are shown below in Table 1:

TABLE 1

Closest germlines for the huIP-10 antibodies.

| Clone ID | VH dp number | VL dp number |
|---|---|---|
| NI-0801 | Vh3_DP-49_(3-30.5) | Vlambda6_6a |
| CF1N1R3P4_C7 | Vh3_DP-49_(3-30.5) | Vlambda6_6a |
| CF1H1R3P3_G11 | Vh3_DP-49_(3-30.5) | Vlambda6_6a |
| CF1A11R3P3_F3 | Vh3_DP-49_(3-30.5) | Vlambda6_6a |
| CF1H1R3P4_B5 | Vh3_DP-49_(3-30.5) | Vlambda6_6a |
| CC21R3P1_F1 | Vh3_DP-49_(3-30.5) | Vlambda6_6a |
| CC21R3P1_B9 | Vh3_DP-49_(3-30.5) | Vlambda3_DPL16_(3l) |
| CB21R3P3_E5 | Vh3_DP-49_(3-30.5) | Vlambda6_6a |
| CC21R3P1_H6 | Vh3_DP-49_(3-30.5) | Vlambda3_3h |
| CC21R3P5_C5 | Vh3_DP-49_(3-30.5) | Vlambda3_3j |
| CB1R3P4_D3 | Vh3_DP-49_(3-30.5) | Vlambda3_DPL16_(3l) |
| CB2R2P4_C3 | Vh2_DP-27,28_(2-70) | Vlambda1_DPL2_(1c) |
| CC21R3P4_F4 | Vh3_DP-49_(3-30.5) | Vlambda3_3h |
| CC21R3P1_C1a | Vh3_DP-49_(3-30.5) | Vlambda3_3h |
| CC21R3P3_C1 | Vh3_DP-49_(3-30.5) | Vlambda3_3h |
| CC21R3P1_E7 | Vh3_DP-49_(3-30.5) | Vlambda1_DPL2_(1c) |
| CE7C1R3H8_J9 | Vh3_DP-49_(3-30.5) | Vlambda1_DPL2_(1c) |
| CB21R3P1_F1 | Vh3_DP-49_(3-30.5) | Vlambda3_DPL16_(3l) |
| CC21R3P1_A2 | Vh3_DP-86_(3-66) | Vlambda1_DPL2_(1c) |
| CB21R3P6_G7 | Vh1_DP-10_(1-69) | Vlambda1_DPL2_(1c) |

In another aspect, the invention provides methods of treating, preventing or alleviating a symptom of an immune-related disorder by administering a huIP-10 antibody to a subject. For example, the huIP-10 antibodies are used to treat, prevent or alleviate a symptom associated with an autoimmune disease or inflammatory disorder. Optionally, the subject is further administered with a second agent such as, but not limited to, an anti-cytokine or anti-chemokine reagent that recognizes cytokines such as interleukin 1 (IL-1), IL-2, IL-4, IL-6, IL-12, IL-13, IL-15, IL-17, IL-18, IL-20, IL-21, IL-22, IL-23, IL-27 and IL-31, and/or chemokines such as MIP1 alpha, MIP1 beta, RANTES, MCP1, IP-10, ITAC, MIG, SDF and fractalkine.

The subject is suffering from or is predisposed to developing an immune related disorder, such as, for example, an autoimmune disease or an inflammatory disorder. Preferably, the subject is a mammal, and more preferably, the subject is a human.

BRIEF DESCRIPTION OF THE DRAWINGS

FIG. 1A-FIG. 3B are a series of graphs depicting the dose-dependent neutralizing activity of huIP-10 antibodies of the invention on hIP-10-induced calcium flux (FIGS. 1A-1B) or cell chemotaxis (FIG. 2A-2B). FIGS. 3A-3B depict the dose-dependent neutralizing activity on native hIP-10.

FIG. 10 is an illustration depicting an alignment of the IP-10 protein sequences from several species: human (SEQ ID NO: 147), cyno (SEQ ID NO: 148), rhesus (SEQ ID NO: 149), rabbit (SEQ ID NO: 150), dog (SEQ ID NO: 151), pig (SEQ ID NO: 152), rat (SEQ ID NO: 153), mouse (SEQ ID NO: 154), goat (SEQ ID NO: 155), cotton rat (SEQ ID NO: 156) and hamster (SEQ ID NO: 157).

DETAILED DESCRIPTION

Figure 1A:
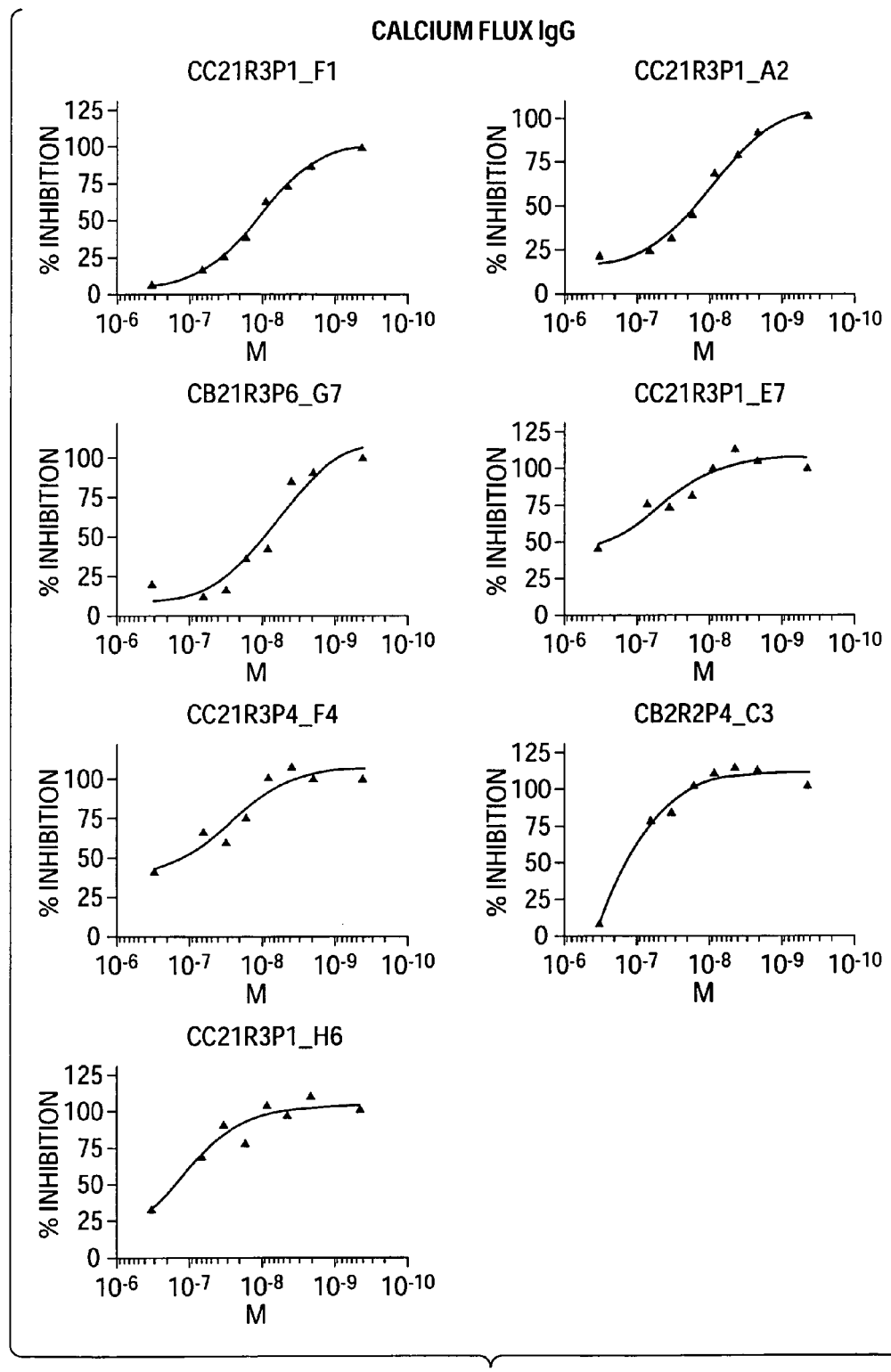

The present invention provides fully human monoclonal antibodies specific for interferon-inducible protein 10 (IP-10, CXCL10). The antibodies are collectively referred to herein as huIP-10 antibodies. The huIP-10 antibodies specifically bind IP-10. As used herein, the terms "specific for", "specific binding", "directed against" (and all grammatical variations thereof) are used interchangeably in the context of antibodies that recognize and bind to an IP-10 epitope when the equilibrium binding constant ($K_d$) is $\leq 1$ μM, e.g., $\leq 100$ nM, preferably $\leq 10$ nM, and more preferably $\leq 1$ nM. For example, the huIP-10 antibodies provided herein exhibit a $K_d$ in the range approximately between $\leq 200$ pM to about 1 pM.

The huIP-10 antibodies are, for example, IP-10 antagonists or inhibitors that modulate at least one biological activity of IP-10. Biological activities of IP-10 include, for example, binding the IP-10 receptor (CXCR3), IP-10 induced calcium flux, IP-10 induced cell chemotaxis, IP-10 binding to glycosaminoglycan, and IP-10 oligomerization. For example, the huIP-10 antibodies completely or partially inhibit IP-10 activity by partially or completely blocking the binding of IP-10 to the IP-10 receptor (CXCR3). The IP-10 antibodies are considered to completely inhibit IP-10 activity when the level of IP-10 activity in the presence of the huIP-10 antibody is decreased by at least 95%, e.g., by 96%, 97%, 98%, 99% or 100% as compared to the level of IP-10 activity in the absence of binding with a huIP-10 antibody described herein. The IP-10 antibodies are considered to partially inhibit IP-10 activity when the level of IP-10 activity in the presence of the huIP-10 antibody is decreased by less than 95%, e.g., 10%, 20%, 25%, 30%, 40%, 50%, 60%, 75%, 80%, 85% or 90% as compared to the level of IP-10 activity in the absence of binding with a huIP-10 antibody described herein.

The huIP-10 antibodies of the invention are produced by immunizing an animal with IP-10, such as, for example, murine or human IP-10 or an immunogenic fragment, derivative or variant thereof. Alternatively, the animal is immunized with cells transfected with a vector containing a nucleic acid molecule encoding IP-10, such that IP-10 is expressed and associated with the surface of the transfected cells. Alternatively, the antibodies are obtained by screening a library that contains antibody or antigen binding domain sequences for binding to IP-10. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

huIP-10 antibodies of the invention include, for example, the heavy chain complementarity determining regions (CDRs) shown below in Table 2, the light chain CDRs shown in Table 3, and combinations thereof.

TABLE 2

VH CDR sequences from antibody clones that bind and neutralize IP-10

| Clone ID | Heavy CDR1 (SEQ ID NO) | Heavy CDR2 | Heavy CDR3 |
|---|---|---|---|
| NI-0801 | NSGIH.... (SEQ ID 5) | VISY.....DGSNKYYADSVKG (SEQ NO 6) | LRDNAEYT...............DY (SEQ NO 7) |
| CF1N1R3P4_C7 | NSGIH.... (SEQ ID 5) | VISY.....DGSNKFYADSVKG (SEQ NO 15) | LRDNAEYT...............DY (SEQ NO 7) |
| CF1H1R3P3_G11 | NSGIH.... (SEQ ID 5) | VISY.....DGSNKFYADSVKG (SEQ NO 15) | LRDNGEYL...............DY (SEQ NO 21) |
| CF1A11R3P3_F3 | NSGIH.... (SEQ ID 5) | VISY.....DGSNKFYADSVKG (SEQ NO 15) | LRDNGEYL...............DY (SEQ NO 21) |
| CF1H1R3P4_B5 | NSGIH.... (SEQ ID 5) | VISY.....DGSNKFYADSVKG (SEQ NO 15) | LRDNGEYL...............DY (SEQ NO 21) |
| CC21R3P1_F1 | NSGIH.... (SEQ ID 5) | VISY.....DGSNKFYADSVKG (SEQ NO 15) | DGSESEYL...............DY (SEQ NO 132) |
| CC21R3P1_B9 | SYGMH.... (SEQ ID 34) | VISY.....DGSNKYYADSVKG (SEQ NO 6) | DGGWYDWYF..............DL (SEQ NO 140) |
| CB21R3P3_E5 | SYGMH.... (SEQ NO 34) | VISY.....DGSIKYYADSVKG (SEQ NO 35) | APDGHQL................DY (SEQ NO 57) |
| CC21R3P1_H6 | NYGMH.... (SEQ NO 95) | VISY.....DGSNRYYADSVKG (SEQ NO 96) | DAGGPL.................DY (SEQ NO 97) |
| CC21R3P5_C5 | TYGMH.... (SEQ NO 86) | VISY.....DGGTKYYADSVKG (SEQ NO 87) | DLGDLPPGL..............DY (SEQ NO 88) |
| CB1R3P4_D3 | SYGMH.... (SEQ NO 34) | VISY.....DGSIKYYADSVKG (SEQ NO 35) | AGYSTDWHP..............DY (SEQ NO 36) |
| CB2R2P4_C3 | TSGMSVI.. (SEQ NO 44) | RID......SDDEKHYNTSLKT (SEQ NO 45) | LRAGSGPYVF.............DS (SEQ NO 46) |
| CC21R3P4_F4 | NYGMH.... (SEQ NO 95) | VISY.....DGSNRYYADSVKG (SEQ NO 96) | DAGGPL.................DY (SEQ NO 97) |
| CC21R3P1_C1a | SYGMH.... (SEQ NO 34) | VISY.....DGSNKYYADSVKG (SEQ NO 6) | DEFDAF.................DI (SEQ NO 78) |
| CC21R3P3_C1 | SYGMH.... (SEQ NO 34) | VISY.....DGSIKYYADSVKG (SEQ NO 35) | DWGFSGSLTF.............DY (SEQ NO 105) |
| CC21R3P1_E7 | TYGMH.... (SEQ NO 86) | VISY.....DGGTKYYADSVKG (SEQ NO 87) | DLGDLPPGL..............DY (SEQ NO 88) |
| CE7C1R3H8_J9 | TYGMH.... | VISY.....DGGTKYYADSVKG (SEQ NO 87) | DLGDLPPGL..............DY (SEQ NO 88) |
| CB21R3P1_F1 | SYGMH.... (SEQ NO 34) | VISY.....DGSIKYYADSVKG (SEQ NO 35) | VMGTDPHSYYYM...........DV (SEQ NO 52) |
| CC21R3P1_A2 | DTYMN.... (SEQ NO 127) | SIY......SDDSTYYADSVKG (SEQ NO 128) | DKEYVTSTGGAYYYFYYM.....DV (SEQ NO 129) |

TABLE 2-continued

VH CDR sequences from antibody clones that bind and neutralize IP-10

| Clone ID | Heavy CDR1 (SEQ ID NO) | Heavy CDR2 | Heavy CDR3 |
|---|---|---|---|
| CB21R3P6_G7 | SFSIT.... (SEQ NO 64) | EITP.....MFGLANYAQKFQG (SEQ NO 65) | DGRFDVSDLLTDKPKVTINYNGMDV (SEQ NO 66) |

TABLE 3

VL CDR sequences from antibody clones that bind and neutralize IP-10

| Clone ID | Light CDR1 | Light CDR2 | Light CDR3 |
|---|---|---|---|
| NI-0801 | TGSGGS......IASNYVQ (SEQ NO 8) | ED.....NQRPS (SEQ NO 9) | QSYDPLPV........WV (SEQ NO 10) |
| CF1N1R3P4_C7 | TGSGGS......IDRNYVQ (SEQ NO 16) | ED.....NQRPS (SEQ NO 9) | QSYDPLPV........WV (SEQ NO 10) |
| CF1H1R3P3_G11 | TGSGGS......IDRNYVQ (SEQ NO 16) | ED.....NQRPS (SEQ NO 9) | QSYDPLPV........WV (SEQ NO 10) |
| CF1A11R3P3_F3 | TGSGGS......IDRNYVQ (SEQ NO 16) | ED.....NQRPS (SEQ NO 9) | QSYDSINL........WV (SEQ NO 29) |
| CF1H1R3P4_B5 | TGSGGS......IDRNYVQ (SEQ NO 16) | ED.....NQRPS (SEQ NO 9) | QSYVETPE........WV (SEQ NO 24) |
| CC21R3P1_F1 | TGSGGS......IDRNYVQ (SEQ NO 16) | ED.....NQRPS (SEQ NO 9) | QSYDSINL........WV (SEQ NO 29) |
| CC21R3P1_B9 | QGDS........LTSYYAS (SEQ NO 141) | GN.....DNRPS (SEQ NO 142) | GSRDSSGYQ.......VV (SEQ NO 143) |
| CB21R3P3_E5 | TGSSGS......IASNYVQ (SEQ NO 133) | ED.....DQRPS (SEQ NO 58) | QSYVSSK.........WV (SEQ NO 59) |
| CC21R3P1_H6 | GGDN........IGRKSVH (SEQ NO 98) | DD.....TDRPS (SEQ NO 99) | QVWDSSIDHS......WV (SEQ NO 100) |
| CC21R3P5_C5 | GGSS........IESKSVH (SEQ NO 119) | KD.....SNRPS (SEQ NO 120) | QVWDSSTG........VV (SEQ NO 121) |
| CB1R3P4_D3 | QGDS........LRSYYAS (SEQ NO 37) | GK.....NNRPS (SEQ NO 38) | NSRDSSGNH.......VV (SEQ NO 39) |
| CB2R2P4_C3 | SGSSSN......IGSNTVN (SEQ NO 47) | NN.....DQRPS (SEQ NO 48) | ASWDDSLNG.......RV (SEQ NO 49) |
| CC21R3P4_F4 | GGNN........IGDKSVQ (SEQ NO 112) | DD.....SDRPS (SEQ NO 113) | QVWDSSSDHPE.....VV (SEQ NO 114) |
| CC21R3P1_C1a | GGNN........IGSRSVH (SEQ NO 79) | YD.....SDRPS (SEQ NO 80) | QVWDTSSGH.......YV (SEQ NO 81) |
| CC21R3P3_C1 | GGNN........IGSKSVH (SEQ NO 106) | YD.....SDRPS (SEQ NO 80) | QVWDSSSDH.......VV (SEQ NO 107) |
| CC21R3P1_E7 | SGSSSN......IGSNTVN (SEQ NO 47) | TN.....NQRPS (SEQ NO 89) | AAWDDSLNGN......VV (SEQ NO 90) |
| CE7C1R3H8_J9 | SGSSSN......IGSNTVN (SEQ NO 47) | TN.....NQRPS (SEQ NO 89) | AAWDDSSEPR......VV (SEQ NO 126) |
| CB21R3P1_F1 | QGDS........LRSYYAS (SEQ NO 37) | GK.....NNRPS (SEQ NO 38) | NSRDSSGNH.......VL (SEQ NO 158) |
| CC21R3P1_A2 | SGSSSN......IGSDTVN (SEQ NO 71) | NN.....NQRPS (SEQ NO 72) | AAWDDSLNG.......LV (SEQ NO 73) |
| CB21R3P6_G7 | SGSSSN......IGSNTVN (SEQ NO 47) | NN.....DQRPS (SEQ NO 48) | ASWDDSLNG.......RV (SEQ NO 49) |

An exemplary huIP-10 monoclonal antibody is the NI-0801 antibody described herein. As shown below, the NI-0801 antibody includes a heavy chain variable region (SEQ ID NO:2) encoded by the nucleic acid sequence shown in SEQ ID NO:1, and a light chain variable region (SEQ ID NO:3) encoded by the nucleic acid sequence shown in SEQ ID NO:4.

>NI-0801 VH nucleic acid sequence
(SEQ ID NO: 1)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAACTCTGGCA

TACACTGGGTCCGCCAGGCTCCAGGCAAGGGACTGGAGTGGGTGGCAGTT

ATATCATATGATGGAAGTAACAAATACTACGCAGACTCCGTGAAGGGCCG

ATTCACCATCTCCAGAGACAACTCCAAGAACACTCTGTATCTGCAAATGA

ACAGCCTGAGAGCTGAGGACACGGCTGTCTATTATTGTGCAAGATTGAGG

GATAATGCGGAGTATACTGATTACTGGGGCCAGGGAACCCTGGTCACCGT

CTCGAGT

>NI-0801 VH amino acid sequence
(SEQ ID NO: 2)
QVQLVESGGGVVQPGRSLRLSCAASGFTFSNSGIHWVRQAPGKGLEWVAV

ISYDGSNKYYADSVKGRFTISRDNSKNTLYLQMNSLRAEDTAVYYCARLR

DNAEYTDYWGQGTLVTVSS

>NI-0801 VL nucleic acid sequence
(SEQ ID NO: 3)
AATTTTATGCTGACTCAGCCCCACTCTGTGTCGGAGTCTCCGGGAAGAC

GGTAACCATCTCCTGCACCGGCAGCGGTGGCAGCATTGCCAGCAACTATG

TGCAGTGGTACCAACAGCGCCCGGGCAGTTCCCCCACCACTGTCATCTAT

GAGGATAACCAGAGACCCTCTGGGGTCCCTGATCGGTTCTCTGGCTCCAT

CGACAGCTCCTCCAATTCTGCCTCCCTCACCATCTCTGGGCTGAAGACTG

AGGACGAGGCTGACTACTACTGTCAGTCTTATGATCCGCTTCCGGTGTGG

GTTTTCGGCGGAGGGACCAAGCTGACCGTCCTAG

>NI-0801 VL amino acid sequence
(SEQ ID NO: 4)
NFMLTQPHSVSESPGKTVTISCTGSGGSIASNYVQWYQQRPGSSPTTVIY

EDNQRPSGVPDRFSGSIDSSSNSASLTISGLKTEDEADYYCQSYDPLPVW

VFGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the NI-0801 antibody have the following sequences: NSGIH (SEQ ID NO:5); VISYDGSNKYYADSVKG (SEQ ID NO:6); and LRDNAEYTDY (SEQ ID NO:7). The light chain CDRs of the NI-0801 antibody have the following sequences: TGSGGSIASNYVQ (SEQ ID NO:8); EDNQRPS (SEQ ID NO:9); and QSYDPLPVWV (SEQ ID NO:10).

An exemplary huIP-10 monoclonal antibody is the CF1N1R3P4_C7 ("C7") antibody described herein. As shown below, the C7 antibody includes a heavy chain variable region (SEQ ID NO:12) encoded by the nucleic acid sequence shown in SEQ ID NO:11, and a light chain variable region (SEQ ID NO:14) encoded by the nucleic acid sequence shown in SEQ ID NO:13.

>CF1N1R3P4_C7 VH nucleic acid sequence
(SEQ ID NO: 11)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAACTCTGGCA

TACACTGGGTCCGCCAGGCTCCAGGCAAGGGACTGGAGTGGGTGGCAGTT

ATATCATATGATGGAAGTAACAAATTCTACGCAGACTCCGTGAAGGGCCG

ATTCACCATCTCCAGAGACAACTCCAAGAACACTCTGTATCTGCAAATGA

ACAGCCTGAGAGCTGAGGACACGGCTGTCTATTATTGTGCAAAATTGAGG

GATAATGCGGAGTATACTGATTACTGGGGCCAGGGAACCCTGGTCACCGT

CTCGAGTG

>CF1N1R3P4_C7 VH amino acid sequence
(SEQ ID NO: 12)
QVQLVESGGGVVQPGRSLRLSCAASGFTFSNSGIHWVRQAPGKGLEWVAV

ISYDGSNKFYADSVKGRFTISRDNSKNTLYLQMNSLRAEDTAVYYCAKLR

DNAEYTDYWGQGTLVTVSS

>CF1N1R3P4_C7 VL nucleic acid sequence
(SEQ ID NO: 13)
AATTTTATGCTGACTCAGCCCCACTCTGTGTCGGAGTCTCCGGGGAAGAC

GGTGACCATCTCCTGCACCGGCAGCGGTGGCAGCATTGACAGAAACTATG

TGCAGTGGTACCAGCAGCGCCCGGGCAGTTCCCCCACCACTGTGATCTAT

GAGGATAACCAAAGACCCTCTGGGGTCCCGGATCGATTCTCTGGCTCCAT

CGACAGCTCCTCCAACTCTGCCTCCCTCACCATCTCTGGACTAAAAACTG

AAGACGAGGCTGACTACTACTGTCAGTCTTATGATCCGCTTCCGGTGTGG

GTTTTCGGCGGAGGGACCAAGCTCACCGTCCTA

>CF1N1R3P4_C7 VL amino acid sequence
(SEQ ID NO: 14)
NFMLTQPHSVSESPGKTVTISCTGSGGSIDRNYVQWYQQRPGSSPTTVIY

EDNQRPSGVPDRFSGSIDSSSNSASLTISGLKTEDEADYYCQSYDPLPVW

VFGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the C7 antibody have the following sequences: NSGIH (SEQ ID NO:5); VISYDGSNKFYADSVKG (SEQ ID NO:15); and LRDNAEYTDY (SEQ ID NO:7). The light chain CDRs of the C7 antibody have the following sequences: TGSGGSIDRNYVQ (SEQ ID NO:16); EDNQRPS (SEQ ID NO:9); and QSYDPLPVWV (SEQ ID NO: 10).

An exemplary huIP-10 monoclonal antibody is the CF1H1R3P3_G11 ("G11") antibody described herein. As shown below, the G11 antibody includes a heavy chain variable region (SEQ ID NO:18) encoded by the nucleic acid sequence shown in SEQ ID NO:17, and a light chain variable region (SEQ ID NO: 14) encoded by the nucleic acid sequence shown in SEQ ID NO:19.

```
>CF1H1R3P3_G11 VH nucleic acid sequence
                                       (SEQ ID NO: 17)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAACTCTGGCA

TACACTGGGTCCGCCAGGCTCCAGGCAAGGGACTGGAGTGGGTGGCAGTT

ATATCATATGATGGAAGTAACAAATTCTACGCAGACTCCGTGAAGGGCCG

ATTCACCATCTCCAGAGACAACTCCAAGAACACTCTGTATCTGCAAATGA

ACAGCCTGAGAGCTGAGGACACGGCTGTCTATTATTGTGCAAAATTGAGG

GATAATGGTGAGTACTTAGACTACTGGGGCCAGGGAACCCTGGTCACCGT

CTCGAGT

>CF1H1R3P3_G11 VH amino acid sequence
                                       (SEQ ID NO: 18)
QVQLVESGGGVVQPGRSLRLSCAASGFTFSNSGIHWVRQAPGKGLEWVAV

ISYDGSNKFYADSVKGRFTISRDNSKNTLYLQMNSLRAEDTAVYYCAKLR

DNGEYLDYWGQGTLVTVSS

>CF1H1R3P3_G11 VL nucleic acid sequence
                                       (SEQ ID NO: 19)
AATTTTATGCTGACTCAGCCCCACTCTGTGTCGGAGTCTCCGGGGAAGAC

GGTGACCATCTCCTGCACCGGCAGCGGTGGCAGCATTGACAGAAACTATG

TGCAGTGGTACCAGCAGCGCCCGGGCAGTTCCCCCACCACTGTGATCTAT

GAGGATAACCAAAGACCCTCTGGGGTCCCGGATCGATTCTCTGGCTCCAT

CGACAGCTCCTCCAACTCTGCCTCCCTCACCATCTCTGGACTAAAAACTG

AAGACGAGGCTGACTACTACTGTCAGTCTTATGATCCGCTTCCGGTGTGG

GTTTTCGGCGGAGGGACCAAGCTCACCGTCCTA

>CF1H1R3P3_G11 VL amino acid sequence
                                       (SEQ ID NO: 14)
NFMLTQPHSVSESPGKTVTISCTGSGGSIDRNYVQWYQQRPGSSPTTVIY

EDNQRPSGVPDRFSGSIDSSSNSASLTISGLKTEDEADYYCQSYDPLPVW

VFGGGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the Gilantibody have the following sequences: NSGIH (SEQ ID NO:5); VISYDGSNKFYADSVKG (SEQ ID NO:15); and LRDNGEYLDY (SEQ ID NO:21). The light chain CDRs of the G11 antibody have the following sequences: TGSGGSIDRNYVQ (SEQ ID NO:16); EDNQRPS (SEQ ID NO:9); and QSYDPLPVWV (SEQ ID NO: 10).

An exemplary huIP-10 monoclonal antibody is the CF1H1R3P4_B5 ("B5") antibody described herein. As shown below, the B5 antibody includes a heavy chain variable region (SEQ ID NO:18) encoded by the nucleic acid sequence shown in SEQ ID NO:17, and a light chain variable region (SEQ ID NO: 22) encoded by the nucleic acid sequence shown in SEQ ID NO: 23.

```
>CF1H1R3P4_B5 VH nucleic acid sequence
                                       (SEQ ID NO: 17)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAACTCTGGCA

TACACTGGGTCCGCCAGGCTCCAGGCAAGGGACTGGAGTGGGTGGCAGTT

ATATCATATGATGGAAGTAACAAATTCTACGCAGACTCCGTGAAGGGCCG

ATTCACCATCTCCAGAGACAACTCCAAGAACACTCTGTATCTGCAAATGA

ACAGCCTGAGAGCTGAGGACACGGCTGTCTATTATTGTGCAAAATTGAGG

GATAATGGTGAGTACTTAGACTACTGGGGCCAGGGAACCCTGGTCACCGT

CTCGAGT

>CF1H1R3P4_B5 VH amino acid sequence
                                       (SEQ ID NO: 18)
QVQLVESGGGVVQPGRSLRLSCAASGFTFSNSGIHWVRQAPGKGLEWVAV

ISYDGSNKFYADSVKGRFTISRDNSKNTLYLQMNSLRAEDTAVYYCAKLR

DNGEYLDYWGQGTLVTVSS

>CF1H1R3P4_B5 VL nucleic acid sequence
                                       (SEQ ID NO: 22)
AATTTTATGCTGACTCAGCCCCACTCTGTGTCGGAGTCTCCGGGGAAGAC

GGTGACCATCTCCTGCACCGGCAGCGGTGGCAGCATTGACAGAAACTATG

TGCAGTGGTACCAGCAGCGCCCGGGCAGTTCCCCCACCACTGTGATCTAT

GAGGATAACCAAAGACCCTCTGGGGTCCCGGATCGATTCTCTGGCTCCAT

CGACAGCTCCTCCAACTCTGCCTCCCTCACCATCTCTGGACTAAAAACTG

AAGACGAGGCTGACTACTACTGTCAGTCTTATGTGGAGACGCCTGAGTGG

GTTTTCGGCGGAGGGACCAAGCTCACCGTCCTAG

>CF1H1R3P4_B5 VL amino acid sequence
                                       (SEQ ID NO: 23)
NFMLTQPHSVSESPGKTVTISCTGSGGSIDRNYVQWYQQRPGSSPTTVIY

EDNQRPSGVPDRFSGSIDSSSNSASLTISGLKTEDEADYYCQSYVETPEW

VFGGGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the B5 antibody have the following sequences: NSGIH (SEQ ID NO:5); VISYDGSNKFYADSVKG (SEQ ID NO:15); and LRDNGEYLDY (SEQ ID NO:21). The light chain CDRs of the B5 antibody have the following sequences: TGSGGSIDRNYVQ (SEQ ID NO:16); EDNQRPS (SEQ ID NO:9); and QSYVETPEWV (SEQ ID NO: 24).

An exemplary huIP-10 monoclonal antibody is the CF1A11R3P3_F3 ("F3") antibody described herein. As shown below, the F3 antibody includes a heavy chain variable region (SEQ ID NO:18) encoded by the nucleic acid sequence shown in SEQ ID NO:17, and a light chain variable region (SEQ ID NO:28) encoded by the nucleic acid sequence shown in SEQ ID NO:27.

>CF1A11R3P3_F3 VH nucleic acid sequence
(SEQ ID NO: 17)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAACTCTGGCA

TACACTGGGTCCGCCAGGCTCCAGGCAAGGGACTGGAGTGGGTGGCAGTT

ATATCATATGATGGAAGTAACAAATTCTACGCAGACTCCGTGAAGGGCCG

ATTCACCATCTCCAGAGACAACTCCAAGAACACTCTGTATCTGCAAATGA

ACAGCCTGAGAGCTGAGGACACGGCTGTCTATTATTGTGCAAAATTGAGG

GATAATGGTGAGTACTTAGACTACTGGGGCCAGGGAACCCTGGTCACCGT

CTCGAGT

>CF1A11R3P3_F3 VH amino acid sequence
(SEQ ID NO: 18)
QVQLVESGGGVVQPGRSLRLSCAASGFTFSNSGIHWVRQAPGKGLEWVAV

ISYDGSNKFYADSVKGRFTISRDNSKNTLYLQMNSLRAEDTAVYYCAKLR

DNGEYLDYWGQGTLVTVSS

>CF1A11R3P3_F3 VL nucleic acid sequence
(SEQ ID NO: 27)
AATTTTATGCTGACTCAGCCCCACTCTGTGTCGGAGTCTCCGGGGAAGAC

GGTGACCATCTCCTGCACCGGCAGCGGTGGCAGCATTGACAGAAACTATG

TGCAGTGGTACCAGCAGCGCCCGGGCAGTGCCCCCATCACTGTGATCTAT

GAGGATAACCAAAGACCCTCTGGGGTCCCGGATCGATTCTCTGGCTCCAT

CGACAGCTCCTCCAACTCTGCCTCCCTCACCATCTCTGGACTACGGACTG

ACGACGAGGCTGACTACTACTGTCAGTCTTATGATAGCATCAATCTTTGG

GTTTTCGGCGGAGGGACCAAGGTCACCGTCCTAGG

>CF1A11R3P3_F3 VL amino acid sequence
(SEQ ID NO: 28)
NFMLTQPHSVSESPGKTVTISCTGSGGSIDRNYVQWYQQRPGSAPITVIY

EDNQRPSGVPDRFSGSIDSSSNSASLTISGLRTDDEADYYCQSYDSINLW

VFGGGTKVTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the F3 antibody have the following sequences: NSGIH (SEQ ID NO:5); VISYDGSNKFYADSVKG (SEQ ID NO:15); and LRDNGEYLDY (SEQ ID NO:21). The light chain CDRs of the F3 antibody have the following sequences: TGSGGSIDRNYVQ (SEQ ID NO:16); EDNQRPS (SEQ ID NO:9); and QSYDSINLWV (SEQ ID NO: 29).

An exemplary huIP-10 monoclonal antibody is the CB1R3P4_D3 ("D3") antibody described herein. As shown below, the D3 antibody includes a heavy chain variable region (SEQ ID NO:31) encoded by the nucleic acid sequence shown in SEQ ID NO:30, and a light chain variable region (SEQ ID NO:33) encoded by the nucleic acid sequence shown in SEQ ID NO:32.

>CB1R3P4_D3 VH nucleic acid sequence
(SEQ ID NO: 30)
CAGGTGCAGCTGGTGCAGTTTGGGGGAGGCGTGGTCCAGCCTGGGAGGT

CCTTGAGACTCTCCTGTGCAGCCTCTGGATTCACCTTCAGTAGCTATGG

CATGCACTGGGTCCGCCAGGCTCCAGGCAAGGGGCTGGAGTGGGTGGCA

GTTATATCATATGATGGAAGTATTAAATACTATGCAGACTCCGTGAAGG

GCCGATTCACCATCTCCAGAGAAAATGCCAAGAACTCCGTGTATCTGCA

AATGGACAGCCTGAGAGTCGGGGACACGGCTGTGTATTACTGTACAAGA

GCCGGGTATAGTACTGACTGGCATCCCGACTACTGGGGCCAGGGACAA

TGGTCACCGTCTCGAGT

>CB1R3P4_D3 VH amino acid sequence
(SEQ ID NO: 31)
QVQLVQFGGGVVQPGRSLRLSCAASGFTFSSYGMHWVRQAPGKGLEWVA

VISYDGSIKYYADSVKGRFTISRENAKNSVYLQMDSLRVGDTAVYYCTR

AGYSTDWHPDYWGQGTMVTVSS

>CB1R3P4_D3 VL nucleic acid sequence
(SEQ ID NO: 32)
TCTTCTGAGCTGACTCAGGACCCTGCTGTGTCTGTGGCCTTGGGACAGA

CAGTCAGGATCACATGCCAAGGAGACAGCCTCAGAAGCTATTATGCAAG

CTGGTACCAGCAGAAGCCAGGACAGGCCCCTGTACTTGCCATCTATGGT

AAAAACAACCGGCCCTCAGGGATCCCAGACCGATTCTCTGGCTCCAGCT

CAGGAAACACAGCTTCCTTGACCATCACTGGGGCTCAGGCGGAAGATGA

GGCTGACTATTACTGTAACTCCCGGGACAGCAGTGGTAACCATGTGGTA

TTCGGCGGAGGGACCAAGCTGACCGTCCTA

>CB1R3P4_D3 VL amino acid sequence
(SEQ ID NO: 33)
SSELTQDPAVSVALGQTVRITCQGDSLRSYYASWYQQKPGQAPVLAIYG

KNNRPSGIPDRFSGSSSGNTASLTITGAQAEDEADYYCNSRDSSGNHVV

FGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the D3 antibody have the following sequences: SYGMH (SEQ ID NO:34); VISYDGSIKYYADSVKG (SEQ ID NO:35); and AGYSTDWHPDY (SEQ ID NO:36). The light chain CDRs of the D3 antibody have the following sequences: QGDSLRSYYAS (SEQ ID NO:37); GKNNRPS (SEQ ID NO:38); and NSRDSSGNHVV (SEQ ID NO: 39).

An exemplary huIP-10 monoclonal antibody is the CB2R2P4_C3 ("C3") antibody described herein. As shown below, the C3 antibody includes a heavy chain variable region (SEQ ID NO:41) encoded by the nucleic acid sequence shown in SEQ ID NO:40, and a light chain variable region (SEQ ID NO:43) encoded by the nucleic acid sequence shown in SEQ ID NO:42.

>CB2R2P4_C3 VH nucleic acid sequence
(SEQ ID NO: 40)
CAGGTCACCTTGAGGGAGTCTGGTCCTGCGCTGGTGAAACCCACACAGAC

CCTCACACTGACCTGCACCTTCTCTGGATTCTCACTCACCACTAGTGGAA

```
TGTCTGTGATTTGGATCCGTCAGCCCCAGGGAAGGCCCTGGAGTGGCTT

GCACGCATTGATTCGGATGACGAGAAACACTACAACACATCTCTGAAGAC

CAGGCTCGCCATCTCCAAGGACACCTCCAAAAACCAGGTGGTCCTTACAA

TGACCAACATGGACCCTGTGGACACAGGCACCTATTACTGTGCACGGCTT

CGGGCTGGTTCAGGTCCATATGTTTTTGACTCCTGGGGGCAAGGGACCAC

GGTCACCGTCTCGAGT

>CB2R2P4_C3 VH amino acid sequence
                                        (SEQ ID NO: 41)
QVTLRESGPALVKPTQTLTLTCTFSGFSLTTSGMSVIWIRQPPGKALEWL

ARIDSDDEKHYNTSLKTRLAISKDTSKNQVVLTMTNMDPVDTGTYYCARL

RAGSGPYVFDSWGQGTTVTVSS

>CB2R2P4_C3 VL nucleic acid sequence
                                        (SEQ ID NO: 42)
CAGTCTGTGCTGACTCAGCCACCCTCAGCGTCTGGGACCCCCGGGCAGAG

GGTCACCATCTCTTGTTCTGGAAGCAGCTCCAACATCGGGAGTAACACTG

TAAACTGGTACCAGCGACTCCCAGGAGCGGCCCCCCAACTCCTCATCTAC

AATAATGACCAGCGGCCCTCAGGGATCCCTGACCGATTCTCTGGCTCCAA

GTCTGGCACCTCAGGCTCCCTGGTCATCAGTGGGCTCCAGTCTGAAGACG

AGGCTGATTACTACTGTGCGTCATGGGATGACAGTCTGAATGGTCGGGTG

TTCGGCGGAGGGACCAAGCTGACCGTCCTAG

>CB2R2P4_C3 VL amino acid sequence
                                        (SEQ ID NO: 43)
QSVLTQPPSASGTPGQRVTISCSGSSSNIGSNTVNWYQRLPGAAPQLLIY

NNDQRPSGIPDRFSGSKSGTSGSLVISGLQSEDEADYYCASWDDSLNGRV

FGGGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the C3 antibody have the following sequences: TSGMSVI (SEQ ID NO:44); RIDSDDEKHYNTSLKT (SEQ ID NO:45); and LRAGSGPYVFDS (SEQ ID NO:46). The light chain CDRs of the C3 antibody have the following sequences: SGSSSNIGSNTVN (SEQ ID NO:47); NNDQRPS (SEQ ID NO:48); and ASWDDSLNGRV (SEQ ID NO:49).

An exemplary huIP-10 monoclonal antibody is the CB21R3P131 ("CB_F1") antibody described herein. As shown below, the CB_F1 antibody includes a heavy chain variable region (SEQ ID NO:51) encoded by the nucleic acid sequence shown in SEQ ID NO:50, and a light chain variable region (SEQ ID NO:145) encoded by the nucleic acid sequence shown in SEQ ID NO:144.

```
>CB21R3P1_F1 VH nucleic acid sequence
                                        (SEQ ID NO: 50)
CAGGTGCAGCTGGTGGAGTCTGGGGGAGGCGTGGTCCGGCCTGGAGGTC

CCTGAGACTCTCCTGTGCAGCCTCTGGATTCACCTTCAGTAGCTATGGCA

TGCACTGGGTCCGCCAGGCTCCAGGCAAGGGGCTGGAGTGGGTGGCAGTT

ATATCATATGATGGAAGTATTAAATACTATGCAGACTCCGTGAAGGGCCG

ATTCACCATCTCCAGAGACAATTCCAAGAACACGCTGTATCTGCAAATGA

ACAGCCTGAGAGCTGAGGACACGGCCATTTATTACTGTGCGAGAGTGATG

GGGACGGATCCCCACTCCTACTACATGGACGTCTGGGGGAAGGGGAC

CCTGGTCACCGTCTCGAGT

>CB21R3P1_F1 VH amino acid sequence
                                        (SEQ ID NO: 51)
QVQLVESGGGVVRPGRSLRLSCAASGFTFSSYGMHWVRQAPGKGLEWVAV

ISYDGSIKYYADSVKGRFTISRDNSKNTLYLQMNSLRAEDTAIYYCARVM

GTDPHSYYYMDVWGKGTLVTVSS

>CB21R3P1_F1 VL nucleic acid sequence
                                        (SEQ ID NO: 144)
TCTTCTGAGCTGACTCAGGACCCTGCTGTGTCTGTGGCCTTGGGACAGAC

AGTCAGGATCACATGCCAAGGAGACAGCCTCAGAAGCTATTATGCAAGCT

GGTACCAGCGGAAGCCAGGACAGGCCCCTGTACTTGTCATCTATGGTAAA

AACAACCGGCCCTCAGGGATCCCAGACCGATTCTCTGGCTCCAGCTCAGG

AAACACAGCTTCCTTGACCATCACTGGGGCTCAGGCGGAAGATGAGGCTG

ACTATTACTGTAACTCCCGGGACAGCAGTGGTAACCATGTGCTTTTCGGC

GGAGGGACCAAGCTGACCGTCCTA

>CB21R3P1_F1 VL amino acid sequence
                                        (SEQ ID NO: 145)
SSELTQDPAVSVALGQTVRITCQGDSLRSYYASWYQRKPGQAPVLVIYGK

NNRPSGIPDRFSGSSSGNTASLTITGAQAEDEADYYCNSRDSSGNHVLFG

GGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the CB_F1 antibody have the following sequences: SYGMH (SEQ ID NO:34); VISYDGSIKYYADSVKG (SEQ ID NO:35); and VMGTDPHSYYYMDV (SEQ ID NO:52). The light chain CDRs of the CB_F1 antibody have the following sequences: QGDSLRSYYAS (SEQ ID NO:37); GKNNRPS (SEQ ID NO:38); and NSRDSSGNHVL (SEQ ID NO: 158).

An exemplary huIP-10 monoclonal antibody is the CB21R3P3_E5 ("E5") antibody described herein. As shown below, the E5 antibody includes a heavy chain variable region (SEQ ID NO:54) encoded by the nucleic acid sequence shown in SEQ ID NO:53, and a light chain variable region (SEQ ID NO:56) encoded by the nucleic acid sequence shown in SEQ ID NO:55.

```
>CB21R3P3_E5 VH nucleic acid sequence
                                        (SEQ ID NO: 53)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAGCTATGGCA

TGCACTGGGTCCGCCAGGCTCCAGGCAAGGGGCTGGAGTGGGTGGCAGTT

ATATCATATGATGGAAGTATTAAATACTATGCAGACTCCGTGAAGGGCCG

ATTCACCATCTCCAGAGACAATTCCAAGAACACGCTGTATCTGCAAATGA
```

```
ACAGCCTGAGAGCTGAGGACGCGGCTGTGTATTACTGTGCGAGAGCACCA

GATGGCCACCAACTTGACTACTGGGGCAGGGGCACCCTGGTCACCGTCTC

GAGT
```

>CB21R3P3_E5 VH amino acid sequence
(SEQ ID NO: 54)
```
QVQLVESGGGVVQPGRSLRLSCAASGFTFSSYGMHWVRQAPGKGLEWVAV

ISYDGSIKYYADSVKGRFTISRDNSKNTLYLQMNSLRAEDAAVYYCARAP

DGHQLDYWGRGTLVTVSS
```

>CB21R3P3_E5 VL nucleic acid sequence
(SEQ ID NO: 55)
```
AATTTTATGCTGACTCAGCCCCACTCTGTGTCGGAGTCTCCGGGGAAGAC

GGTAACCATCTCCTGCACCGGCAGCAGTGGCAGCATTGCCAGCAACTATG

TGCAGTGGTACCAGCAGCGCCCGGGCAGTGCCCCCACCACTGTGATCTAT

GAAGATGACCAAAGACCCTCTGACGTCCCTGATCGCTTCTCTGGCTCCAT

CGACAGCTCCTCCAACTCTGCCTCCCTCACCATCTCTGGACTGAGGACTG

AGGACGAGGCTGACTACTACTGTCAGTCTTATGTTAGCAGCAAGTGGGTG

TTCGGCGGAGGGACCAAGCTGACCGTCCTA
```

>CB21R3P3_E5 VL amino acid sequence
(SEQ ID NO: 56)
```
NFMLTQPHSVSESPGKTVTISCTGSSGSIASNYVQWYQQRPGSAPTTVIY

EDDQRPSDVPDRFSGSIDSSSNSASLTISGLRTEDEADYYCQSYVSSKWV

FGGGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the E5 antibody have the following sequences: SYGMH (SEQ ID NO:34); VISYDGSIKYYADSVKG (SEQ ID NO:35); and APDGHQLDY (SEQ ID NO:57). The light chain CDRs of the E5 antibody have the following sequences: TGSSGSIASNYVQ (SEQ ID NO:133); EDDQRPS (SEQ ID NO:58); and QSYVSSKVWV (SEQ ID NO: 59).

An exemplary huIP-10 monoclonal antibody is the CB21R3P6_G7 ("G7") antibody described herein. As shown below, the G7 antibody includes a heavy chain variable region (SEQ ID NO:61) encoded by the nucleic acid sequence shown in SEQ ID NO:60, and a light chain variable region (SEQ ID NO:63) encoded by the nucleic acid sequence shown in SEQ ID NO:62.

>CB21R3P6_G7 VH nucleic acid sequence
(SEQ ID NO: 60)
```
CAGGTGCAGCTGGTGCAGTCTGGGGCTGAGGTGAAGAAGCCTGGGTCCTC

GGTGACGGTCTCCTGCAAGGCCTCTGGAGGCACCTTCAGCAGCTTTTCTA

TCACCTGGCTGCGACAGGCCCCTGGACAAGGGCTTGAGTGGATGGGAGAG

ATCACCCCTATGTTTGGTATAGCAAACTACGCACAGAAGTTCCAGGGTAG

GGTCACGATTAGCGCGGACGAGTCCACGAGCACAGCCTACATGGAGTTGA

GTGGCCTGACATCTGAAGCACACGGCCATGTATTATTGTGCGAGAGATGGT

CGGTTTGATGTTTCCGATCTTTTGACTGACAAACCCAAAGTAACGATAAA

CTACAACGGGATGGACGTCTGGGGCCAAGGCACCCTGGTCACCGTCTCGA

GT
```

>CB21R3P6_G7 VH amino acid sequence
(SEQ ID NO: 61)
```
QVQLVQSGAEVKKPGSSVTVSCKASGGTFSSFSITWLRQAPGQGLEWMGE

ITPMFGIANYAQKFQGRVTISADESTSTAYMELSGLTSEDTAMYYCARDG

RFDVSDLLTDKPKVTINYNGMDVWGQGTLVTVSS
```

>CB21R3P6_G7 VL nucleic acid sequence
(SEQ ID NO: 62)
```
CAGTCTGTGCTGACTCAGCCACCCTCAGCGTCTGGGACCCCCGGGCAGAG

GGTCACCATCTCTTGTTCTGGAAGCAGCTCCAACATCGGGAGTAACACTG

TAAACTGGTACCAGCGACTCCCAGGAGCGGCCCCCCAACTCCTCATCTAC

AATAATGACCAGCGGCCCTCAGGGATCCCTGACCGATTCTCTGGCTCCAA

GTCTGGCACCTCAGGCTCCCTGGTCATCAGTGGGCTCCAGTCTGAAGATG

AGGCTGATTACTACTGTGCGTCATGGGATGACAGTCTGAATGGTCGGGTG

TTCGGCGGAGGGACCAAGCTGACCGTCCTA
```

>CB21R3P6_G7 VL amino acid sequence
(SEQ ID NO: 63)
```
QSVLTQPPSASGTPGQRVTISCSGSSSNIGSNTVNWYQRLPGAAPQLLIY

NNDQRPSGIPDRFSGSKSGTSGSLVISGLQSEDEADYYCASWDDSLNGRV

FGGGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the G7 antibody have the following sequences: SFSIT (SEQ ID NO:64); EITPMFGIANYAQKFQG (SEQ ID NO:65); and DGRFDVSDLLTDKPKVTINYNGMDV (SEQ ID NO:66). The light chain CDRs of the G7 antibody have the following sequences: SGSSSNIGSNTVN (SEQ ID NO:47); NNDQRPS (SEQ ID NO:48); and ASWDDSLNGRV (SEQ ID NO:49).

An exemplary huIP-10 monoclonal antibody is the CC21R3P1_A2 ("A2") antibody described herein. As shown below, the A2 antibody includes a heavy chain variable region (SEQ ID NO:68) encoded by the nucleic acid sequence shown in SEQ ID NO:67, and a light chain variable region (SEQ ID NO:70) encoded by the nucleic acid sequence shown in SEQ ID NO:69.

>CC21R3P1_A2 VH nucleic acid sequence
(SEQ ID NO: 67)
```
CAGCTGGTGGAGTCTGGAGGAGGCTTGATCCAGCCTGGGGGGTCCCTGAG

ACTTTCCTGTGCAGCCTCTGGATTCAGCGTCAGTGACACCTACATGAACT

GGGTCCGCCAGGCTCCAGGGAAGGGCCTGGAGTGGGTGTCAAGTATTTAT

AGCGATGATAGCACATACTACGCAGACTCCGTGAAGGGCAGATTCACCAT

CTCCAGAGACAATTCCAAGAACACGCTGTTTCTTCAAATAAACAGTTTGA

GAGCCGAGGACACGGCTGTCTATTACTGTGCGAGAGATAAGGAGTATGTA

ACATCAACTGGGGGCGCCTACTACTACTTCTACTACATGGACGTCTGGGG
```

CCAGGGCACCCTGGTCACCGTCTCGAGT

>CC21R3P1_A2 VH amino acid sequence
(SEQ ID NO: 68)
QLVESGGGLIQPGGSLRLSCAASGFSVSDTYMNWVRQAPGKGLEWVSSIY

SDDSTYYADSVKGRFTISRDNSKNTLFLQINSLRAEDTAVYYCARDKEYV

TSTGGAYYYFYYMDVWGQGTLVTVSS

>CC21R3P1_A2 VL nucleic acid sequence
(SEQ ID NO: 69)
CAGTCTGTGCTGACTCAGCCACCCTCAGCGTCTGGGACCCCCGGGCAGAG

AGTCTCCATCTCCTGTTCTGGAAGCAGCTCCAACATCGGAAGTGATACTG

TGAACTGGTACCAGCACCTCCCAGGAACGGCCCCCAAACTCCTCATCTAT

AATAATAATCAGCGGCCCTCAGGGGTCCCTGACCGATTCTCTGGCTCCAA

GTCTGGCACCTCAGCCTCCCTGGCCATCAGTGGGCTCCAGTCTGAGGATG

AGGCTGATTATTACTGTGCCGCATGGGATGACAGCCTGAATGGTCTGGTA

TTCGGCGGAGGGACCAAGGTCACCGTCCTA

>CC21R3P1_A2 VL amino acid sequence
(SEQ ID NO: 70)
QSVLTQPPSASGTPGQRVSISCSGSSSNIGSDTVNWYQHLPGTAPKLLIY

NNNQRPSGVPDRFSGSKSGTSASLAISGLQSEDEADYYCAAWDDSLNGLV

FGGGTKVTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the A2 antibody have the following sequences: DTYMN (SEQ ID NO:127); SIYSDDSTYY-ADSVKG (SEQ ID NO:128); and DKEYVTSTGGAYYY-FYYMDV (SEQ ID NO:129). The light chain CDRs of the A2 antibody have the following sequences: SGSSSNIGS-DTVN (SEQ ID NO:71); NNNQRPS (SEQ ID NO:72); and AAWDDSLNGLV (SEQ ID NO:73).

An exemplary huIP-10 monoclonal antibody is the CC21R3P1_C1A ("C1a") antibody described herein. As shown below, the C1a antibody includes a heavy chain variable region (SEQ ID NO:75) encoded by the nucleic acid sequence shown in SEQ ID NO:74, and a light chain variable region (SEQ ID NO:77) encoded by the nucleic acid sequence shown in SEQ ID NO:76.

>CC21R3P1_C1A VH nucleic acid sequence
(SEQ ID NO: 74)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAGCTATGGCA

TGCACTGGGTCCGCCAGGCTCCAGGCAAGGGGCTGGAGTGGGTGGCAGTT

ATATCATATGATGGAAGTAATAAATACTATGCAGACTCCGTGAAGGGCCG

ATTCACCATCTCCAGAGACAATTCCAAGAACACGCTGTATCTGCAAATGA

ACAGCCTGAGAGCTGAGGACACGGCTGTGTATTACTGTGCGAAAGACGAG

TTTGATGCTTTTGATATCTGGGGCCGAGGGACAATGGTCACCGTCTCGAG

T

>CC21R3P1_C1A VH amino acid sequence
(SEQ ID NO: 75)
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAKDE

FDAFDIWGRGTMVTVSS

>CC21R3P1_C1A VL nucleic acid sequence
(SEQ ID NO: 76)
TCCTATGTGCTGACTCAGCCCCCCTCAGTGTCGGTGGCCCCAGGAACGAC

GGCCAGGATTACCTGTGGGGGAAACAATATCGGAAGTAGGAGTGTGCATT

GGTACCAGCAGAAGCCAGGCCAGGCCCCTCTACTGGTCATCTATTATGAT

AGTGACCGGCCCTCAGGGATCCCTCTGCGATTCTCTGGCTCCAACTCTGG

AAACACGGCCACCCTGACCATCAGTAGGGTCGAAGCCGGGGATGAGGCCG

ACTATTACTGTCAGGTGTGGGATACTAGTAGTGGTCATTATGTCTTCGGA

ACTGGGACCAAGGTCACCGTCCTA

>CC21R3P1_C1A VL amino acid sequence
(SEQ ID NO: 77)
SYVLTQPPSVSVAPGTTARITCGGNNIGSRSVHWYQQKPGQAPLLVIYYD

SDRPSGIPLRFSGSNSGNTATLTISRVEAGDEADYYCQVWDTSSGHYVFG

TGTKVTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the C1a antibody have the following sequences: SYGMH (SEQ ID NO:34); VISYDGSNKYY-ADSVKG (SEQ ID NO:6); and DEFDAFDI (SEQ ID NO:78). The light chain CDRs of the C1a antibody have the following sequences: GGNNIGSRSVH (SEQ ID NO:79); YDSDRPS (SEQ ID NO:80); and QVWDTSSGHYV (SEQ ID NO: 81).

An exemplary huIP-10 monoclonal antibody is the CC21R3P3_C1 ("C1") antibody described herein. As shown below, the C1 antibody includes a heavy chain variable region (SEQ ID NO:102) encoded by the nucleic acid sequence shown in SEQ ID NO:101, and a light chain variable region (SEQ ID NO:104) encoded by the nucleic acid sequence shown in SEQ ID NO:103.

>CC21R3P3_C1 VH nucleic acid sequence
(SEQ ID NO: 101)
CAGGTGCAGCTGGTGGAGTCTGGGGGAGGCGTGGTCCAGCCTGGGAGGTC

CCTGAGACTCTCCTGTGCAGCCTCTGGATTCACCTTCAGTAGCTATGGCA

TGCACTGGGTCCGCCAGGCTCCAGGCAAGGGGCTGGAGTGGGTGGCAGTT

ATATCATATGATGGAAGTATTAAATACTATGCAGACTCCGTGAAGGGCCG

ATTCACCATCTCCAGAGACAATTCCAGGAACACGCTGTATCTGCAGATGA

ACAGCCTGAGACCTGAGGACACGGCTGTTTATTACTGTGCGAAAGATTGG

GGATTTAGCGGCTCCCTAACATTTGATTATTGGGGCCAAGGGACAATGGT

CACCGTCTCGAGT

>CC21R3P3_C1 VH amino acid sequence
(SEQ ID NO: 102)
QVQLVESGGGVVQPGRSLRLSCAASGFTFSSYGMHWVRQAPGKGLEWVAV

ISYDGSIKYYADSVKGRFTISRDNSRNTLYLQMNSLRPEDTAVYYCAKDW

GFSGSLTFDYWGQGTMVTVSS

>CC21R3P3_C1 VL nucleic acid sequence
(SEQ ID NO: 103)
TCCTATGTGCTGACTCAGCCACCCTCAGTGTCAGTGGCCCCAGGAAAGAC

GGCCAGGATTACCTGTGGGGGAAACAACATTGGAAGTAAAAGTGTGCACT

GGTACCAGCAGAAGCCAGGCCAGGCCCCTGTGCTGGTCATCTATTATGAT

AGCGACCGGCCCTCAGGGATCCCTGAGCGATTCTCTGGCTCCAACTCTGG

GAACACGGCCACCCTGACCATCAGCAGGGTCGAAGCCGGGGATGAGGCCG

ACTATTACTGTCAGGTGTGGGATAGTAGTAGTGATCATGTGGTATTCGGC

GGAGGGACCAAGGTCACCGTCCTA

>CC21R3P3_C1 VL amino acid sequence
(SEQ ID NO: 104)
SYVLTQPPSVSVAPGKTARITCGGNNIGSKSVHWYQQKPGQAPVLVIYYD

SDRPSGIPERFSGSNSGNTATLTISRVEAGDEADYYCQVWDSSSDHVVFG

GGTKVTVL

The amino acids encompassing the complementarity determining regions (CDR) are as defined by Chothia et al. and B. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the C1 antibody have the following sequences: SYGMH (SEQ ID NO:34); VISYDGSIKYY-ADSVKG (SEQ ID NO:35); and DWGFSGSLTFDY (SEQ ID NO:105). The light chain CDRs of the C1 antibody have the following sequences: GGNNIGSKSVH (SEQ ID NO:106); YDSDRPS (SEQ ID NO:80); and QVWDSSS-DHVV (SEQ ID NO: 107).

An exemplary huIP-10 monoclonal antibody is the CC21R3P1_E7 ("E7") antibody described herein. As shown below, the E7 antibody includes a heavy chain variable region (SEQ ID NO:83) encoded by the nucleic acid sequence shown in SEQ ID NO:82, and a light chain variable region (SEQ ID NO:85) encoded by the nucleic acid sequence shown in SEQ ID NO:84.

>CC21R3P1_E7 VH nucleic acid sequence
(SEQ ID NO: 82)
CAGCTGGTGGAGTCTGGGGGAGGCGTGGTCCAGCCTGGGAGGTCCCTGAG

ACTCTCCTGTGCAGCCTCTGGATTCACCTTCAGTACCTATGGCATGCACT

GGGTCCGCCAGGCTCCAGGCAAGGGGCTGGAGTGGGTGGCAGTTATATCA

TATGATGGAGGTACTAAATACTATGCAGACTCCGTGAAGGGCCGATTCAC

CATCTCCAGAGACAATTCCATGAAAACGCTCTATCTGCAAATGAACAGCC

TGAGAACTGAGGACACGGCTGTGTATTACTGTGCGAAAGATCTGGGGGAC

CTACCCCCGGGCCTTGACTACTGGGGCCAGGGGACAATGGTCACCGTCTC

GAGT

>CC21R3P1_E7 VH amino acid sequence
(SEQ ID NO: 83)
QLVESGGGVVQPGRSLRLSCAASGFTFSTYGMHWVRQAPGKGLEWVAVIS

YDGGTKYYADSVKGRFTISRDNSMKTLYLQMNSLRTEDTAVYYCAKDLGD

LPPGLDYWGQGTMVTVSS

>CC21R3P1_E7 VL nucleic acid sequence
(SEQ ID NO: 84)
CAGTCTGTGCTGACTCAGCCACCCTCAGCGTCTGGGACCCCCGGGCAGAG

GGTCACCATCTCTTGTTCTGGAAGCAGCTCCAACATCGGAAGTAATACTG

TAAACTGGTACCAGCAGCTCCCAGGAGCGGCCCCCAAACTCCTCATCTAT

ACTAATAATCAGCGGCCCTCAGGGGTCCCTGACCGATTCTCTGGCTCCAA

GTCTGGCACCTCAGCCTCCCTGGCCATCAGTGGGCTCCAGTCTGAGGATG

AGGCTGATTATTACTGTGCAGCATGGGATGACAGCCTGAATGGTAATGTG

GTATTCGGCGGAGGGACCAAGGTCACCGTCCTA

>CC21R3P1_E7 VL amino acid sequence
(SEQ ID NO: 85)
QSVLTQPPSASGTPGQRVTISCSGSSSNIGSNTVNWYQQLPGAAPKLLIY

TNNQRPSGVPDRFSGSKSGTSASLAISGLQSEDEADYYCAAWDDSLNGNV

VFGGGTKVTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the E7 antibody have the following sequences: TYGMH (SEQ ID NO:86); VISYDGGTKYY-ADSVKG (SEQ ID NO:87); and DLGDLPPGLDY (SEQ ID NO:88). The light chain CDRs of the E7 antibody have the following sequences: SGSSSNIGSNTVN (SEQ ID NO:47); TNNQRPS(SEQ ID NO:89); and AAWDDSLNGNVV (SEQ ID NO: 90).

An exemplary huIP-10 monoclonal antibody is the CC21R3P1_H6 ("H6") antibody described herein. As shown below, the H6 antibody includes a heavy chain variable region (SEQ ID NO:92) encoded by the nucleic acid sequence shown in SEQ ID NO:91, and a light chain variable region (SEQ ID NO:94) encoded by the nucleic acid sequence shown in SEQ ID NO:93.

>CC21R3P1_H6 VH nucleic acid sequence
(SEQ ID NO: 91)
CAGGTGCAGCTGGTGGAGTCTGGGGGAGGCGTGGCTCAGTCTGGGAAGTC

CCTGAGACTCTCCTGTGCAGCCTCTGGATTCACCTTCAGTAACTATGGCA

TGCACTGGGTCCGCCAGGCTCCAGGCAAGGGGCTGGAGTGGCTGGCAGTC

ATATCATATGATGGAAGTAACAGATACTATGCAGACTCCGTGAAGGGCCG

ATTCACCATCTCCAGAGACAATTCCAACAACACACTGAATCTGCAAATGA

GCAGCCTGAGAGCTGAGGACACGGCTCTATATTACTGTGCGAAAGATGCC

GGGGGGCCGCTTGATTACTGGGGCAAGGGCACCCTGGTCACCGTCTCGAG

T

>CC21R3P1_H6 VH amino acid sequence
(SEQ ID NO: 92)
QVQLVESGGGVAQSGKSLRLSCAASGFTFSNYGMHWVRQAPGKGLEWLAV

ISYDGSNRYYADSVKGRFTISRDNSNNTLNLQMSSLRAEDTALYYCAKDA

GGPLDYWGKGTLVTVSS

>CC21R3P1_H6 VL nucleic acid sequence
(SEQ ID NO: 93)
CAGTCTGTGCTGACTCAGCTGACTCAGCCACCCTCGGTGTCACTGGCCCC

AGGACAGACGGCCACCATTACTTGTGGGGGAGACAACATTGGACGTAAAA

GTGTGCACTGGTACCAGCAGAAGCCAGGCCAGGCCCCTGTGTTGGTCGTC

TATGATGACACCGACCGGCCCTCAGGGATCCCTGAGCGATTCTCTGGCTC

CAACTCTGGGAACACGGCCACCCTAACCATCAGCAGGGTCGAAGCCGGGG

ATGAGGCCGACTATTACTGTCAGGTGTGGGATAGTAGTATTGATCATTCT

TGGGTGTTCGGCGGAGGGACCAAGCTGACCGTCCTAG

>CC21R3P1_H6 VL amino acid sequence
(SEQ ID NO: 94)
QSVLTQLTQPPSVSLAPGQTATITCGGDNIGRKSVHWYQQKPGQAPVLVV

YDDTDRPSGIPERFSGSNSGNTATLTISRVEAGDEADYYCQVWDSSIDHS

WVFGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the H6 antibody have the following sequences: NYGMH (SEQ ID NO:95); VISYDGSNRYY-ADSVKG (SEQ ID NO:96); and DAGGPLDY (SEQ ID NO:97). The light chain CDRs of the H6 antibody have the following sequences: GGDNIGRKSVH (SEQ ID NO:98); DDTDRPS (SEQ ID NO:99); and QVWDSSIDHSWV (SEQ ID NO:100).

An exemplary huIP-10 monoclonal antibody is the CC21R3P4_F4 ("F4") antibody described herein. As shown below, the F4 antibody includes a heavy chain variable region (SEQ ID NO:109) encoded by the nucleic acid sequence shown in SEQ ID NO:108, and a light chain variable region (SEQ ID NO:111) encoded by the nucleic acid sequence shown in SEQ ID NO:110.

>CC21R3P4_F4 VH nucleic acid sequence
(SEQ ID NO: 108)
CAGGTGCAGCTGGTGGAGTCTGGGGGAGGCGTGGCTCACTCTGGGAAGTC

CCTGAGACTCTCCTGTGCAGCCTCTGGATTCACCTTCAGTAACTATGGCA

TGCACTGGGTCCGCCAGGCTCCAGGCAAGGGGCTGGAGTGGCTGGCAGTC

ATATCATATGATGGGAGTAATAGATACTATGCAGACTCCGTGAAGGGCCG

ATTCACCATCTCCAGAGACAATTCCAACAACACGCTGAATCTGCAAATGA

GCAGCCTGAGAGCTGAGGACACGGCTCTGTATTACTGTGCGAAAGATGCC

GGGGGGCCGCTTGATTACTGGGGCCGGGGCACCCTGGTCACCGTCTCGAG

T

>CC21R3P4_F4 VH amino acid sequence
(SEQ ID NO: 109)
QVQLVESGGGVAHSGKSLRLSCAASGFTFSNYGMHWVRQAPGKGLEWLAV

ISYDGSNRYYADSVKGRFTISRDNSNNTLNLQMSSLRAEDTALYYCAKDA

GGPLDYWGRGTLVTVSS

>CC21R3P4_F4 VL nucleic acid sequence
(SEQ ID NO: 110)
TCCTATGTGCTGACTCAGCCACCCTCGGTGTCAGTGGCCCCAGGACAGAT

GGCCAGAATTACCTGTGGGGGAAACAACATTGGAGATAAAAGTGTGCAAT

GGTACCAGCAGAGGCCAGGCCAGGCCCCTCTACTGGTCGTCTATGATGAT

AGCGACCGGCCCTCAGGGATCCCTGAGCGCTTCTCTGGCTCCTACTCTAG

GAACACGGCCACCCTGACCATCAGCAGGGTCGAAGCCGGGGATGAGGCCG

ACTATTACTGTCAGGTGTGGGATAGTAGTAGTGATCATCCGGAGGTGGTT

TTCGGCGGAGGGACCAAGCTGACCGTCCTA

>CC21R3P4_F4 VL amino acid sequence
(SEQ ID NO: 111)
SYVLTQPPSVSVAPGQMARITCGGNNIGDKSVQWYQQRPGQAPLLVVYDD

SDRPSGIPERFSGSYSRNTATLTISRVEAGDEADYYCQVWDSSSDHPEVV

FGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the F4 antibody have the following sequences: NYGMH (SEQ ID NO:95); VISYDGSNRYY-ADSVKG (SEQ ID NO:96); and DAGGPLDY (SEQ ID NO:97). The light chain CDRs of the F4 antibody have the following sequences: GGNNIGDSKVQ (SEQ ID NO:112); DDSDRPS (SEQ ID NO:113); and QVWDSSSDHPEVV (SEQ ID NO: 114).

An exemplary huIP-10 monoclonal antibody is the CC21R3P5_C5 ("C5") antibody described herein. As shown below, the C5 antibody includes a heavy chain variable region (SEQ ID NO:116) encoded by the nucleic acid sequence shown in SEQ ID NO:115, and a light chain variable region (SEQ ID NO:118) encoded by the nucleic acid sequence shown in SEQ ID NO:117.

>CC21R3P5_C5 VH nucleic acid sequence
(SEQ ID NO: 115)
CAGGTCCAGCTGGTGCAGTCTGGGGGAGGCGTGGTCCAGCCTGGGAGG

TCCCTGAGACTCTCCTGTGCAGCCTCTGGATTCACCTTCAGTACCTAT

GGCATGCACTGGGTCCGCCAGGCTCCAGGCAAGGGGCTGGAGTGGGTG

GCAGTTATATCATATGATGGAGGTACTAAATACTATGCAGACTCCGTG

AAGGGCCGATTCACCATCTCCAGAGACAATTCCATGAAAACGCTCTAT

CTGCAAATGAACAGCCTGAGAACTGAGGACACGGCTGTGTATTACTGT

GCGAAAGATCTGGGGGACCTACCCCCGGGCCTTGACTACTGGGGCCGA

GGGACAATGGTCACCGTCTCGAGT

>CC21R3P5_C5 VH amino acid sequence
(SEQ ID NO: 116)
QVQLVQSGGGVVQPGRSLRLSCAASGFTFSTYGMHWVRQAPGKGLEWV

AVISYDGGTKYYADSVKGRFTISRDNSMKTLYLQMNSLRTEDTAVYYC

AKDLGDLPPGLDYWGRGTMVTVSS

>CC21R3P5_C5 VL nucleic acid sequence
(SEQ ID NO: 117)
TCCTATGAGCTGACTCAGCCACCCTCAGTGTCAGTGGCCCTGGGACAG

ACGGCCACGATTACCTGTGGGGGGAGCAGTATTGAGAGTAAAAGTGTA

```
CACTGGTACCAGGAGAAGCCAGGCCAGGCCCCTGTCCTGGTCATCTAT

AAAGATTCCAACCGGCCCTCTGTGATCCCTGAGCGATTCTCTGGCTCC

AACTCGGGGAACACGGCCACCCTGACCATCGGCAGAGCCCAAGCCGGG

GATGAGGCTGACTATTACTGTCAGGTGTGGGACAGCAGTACTGGTGTG

GTATTCGGCGGAGGGACCAAGCTGACCGTCCTA
>CC21R3P5_C5 VL amino acid sequence
                                        (SEQ ID NO: 118)
SYELTQPPSVSVALGQTATITCGGSSIESKSVHWYQEKPGQAPVLVIY

KDSNRPSVIPERFSGSNSGNTATLTIGRAQAGDEADYYCQVWDSSTGV

VFGGGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the C5 antibody have the following sequences: TYGMH (SEQ ID NO:86); VISYDGGTKYYADSVKG (SEQ ID NO:87); and DLGDLPPGLDY (SEQ ID NO:88). The light chain CDRs of the C5 antibody have the following sequences: GGSSIESKSVH (SEQ ID NO:119); KDSNRPS (SEQ ID NO:120); and QVWDSSTGVV (SEQ ID NO: 121).

An exemplary huIP-10 monoclonal antibody is the CE7C1R3H8_J9 ("J9") antibody described herein. As shown below, the J9 antibody includes a heavy chain variable region (SEQ ID NO:123) encoded by the nucleic acid sequence shown in SEQ ID NO:122, and a light chain variable region (SEQ ID NO:125) encoded by the nucleic acid sequence shown in SEQ ID NO:124.

```
>CE7C1R3H8_J9 VH nucleic acid sequence
                                        (SEQ ID NO: 122)
CAGGTCCAGTTGGTGGAGTCTGGGGGAGGCGTGGTCCAGCCTGGGAGG

TCCCTGAGACTCTCCTGTGCAGCCTCTGGATTCACCTTCAGTACCTAT

GGCATGCACTGGGTCCGCCAGGCTCCAGGCAAGGGGCTGGAGTGGGTG

GCAGTTATATCATATGATGGAGGTACTAAATACTATGCAGACTCCGTG

AAGGGCCGATTCACCATCTCCAGAGACAATTCCATGAAAACGCTCTAT

CTGCAAATGAACAGCCTGAGAACTGAGGACACGGCTGTGTATTACTGT

GCGAAAGATCTGGGGGACCTACCCCCGGGCCTTGACTACTGGGGCCAG

GGGACAATGGTCACCGTCTCGAGT
>CE7C1R3H8_J9 VH amino acid sequence
                                        (SEQ ID NO: 123)
QVQLVESGGGVVQPGRSLRLSCAASGFTFSTYGMHWVRQAPGKGLEWV

AVISYDGGTKYYADSVKGRFTISRDNSMKTLYLQMNSLRTEDTAVYYC

AKDLGDLPPGLDYWGQGTMVTVSS
>CE7C1R3H8_J9 VL nucleic acid sequence
                                        (SEQ ID NO: 124)
CAGTCTGTGCTGACTCAGCCACCCTCAGCGTCTGGGACCCCCGGGCAG

AGGGTCACCATCTCTTGTTCTGGAAGCAGCTCCAACATCGGAAGTAAT

ACTGTAAACTGGTACCAGCAGCTCCCAGGAGCGGCCCCCAAACTCCTC

ATCTATACTAATAATCAGCGGCCCTCAGGGGTCCCCGACCGATTCTCT

GGCTCCAAGTCTGGCACCTCAGCCTCCCTGGCCATCAGTGGGCTCCAG

TCTGAGGATGAGGCTGATTATTACTGTGCAGCATGGGATGACAGCTCG

GAGCCTCGTGTGGTATTCGGCGGAGGGACCAAGGTCACCGTCCTA
>CE7C1R3H8_J9 VL amino acid sequence
                                        (SEQ ID NO: 125)
QSVLTQPPSASGTPGQRVTISCSGSSSNIGSNTVNWYQQLPGAAPKLL

TYTNNQRFSGVPDRFSGSKSGTSASLAISGLQSEDEADYYCAAWDDSS

EPRVVFGGGTKVTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the J9 antibody have the following sequences: TYGMH (SEQ ID NO:86); VISYDGGTKYYADSVKG (SEQ ID NO:87); and DLGDLPPGLDY (SEQ ID NO:88). The light chain CDRs of the J9 antibody have the following sequences: SGSSSNIGSNTVN (SEQ ID NO:47); TNNQRPS (SEQ ID NO:89); and AAWDDSSEPRVV (SEQ ID NO: 126).

An exemplary huIP-10 monoclonal antibody is the CC21R3P1_B9 ("B9") antibody described herein. As shown below, the B9 antibody includes a heavy chain variable region (SEQ ID NO:137) encoded by the nucleic acid sequence shown in SEQ ID NO:136, and a light chain variable region (SEQ ID NO:139) encoded by the nucleic acid sequence shown in SEQ ID NO:138.

```
>CC21R3P1_B9 VH nucleic acid sequence
                                        (SEQ ID NO: 136)
GAGGTGCAGCTGGTGCAGTCTGGGGGAGGCGTGGTCCAGCCTGGGAGG

TCCCTGAGACTCTCCTGTGCAGCCTCTGGATTCACCTTCAGTAGCTAT

GGCATGCACTGGGTCCGCCAGGCTCCAGGCAAGGGGCTGGAGTGGGTG

GCAGTTATATCATATGATGGAAGTAATAAATACTATGCAGACTCCGTG

AAGGGCCGATTCACCATCTCCAGAGACAATTCCAAGAACACGCTGTAT

CTGCAAATGAACAGCCTGAGAGCTGAGGACACGGCTGTGTATTACTGT

GCGAAAGACGGTGGCTGGTACGACTGGTACTTCGATCTCTGGGGCAGG

GGAACCCTGGTCACCGTCTCGAGT
>CC21R3P1_B9 VH amino acid sequence
                                        (SEQ ID NO: 137)
EVQLVQSGGGVVQPGRSLRLSCAASGFTFSSYGMHWVRQAPGKGLEWV

AVISYDGSNKYYADSVKGRFTISRDNSKNTLYLQMNSLRAEDTAVYYC

AKDGGWYDWYFDLWGRGTLVTSS
>CC21R3P1_B9 VL nucleic acid sequence
                                        (SEQ ID NO: 138)
TCTTCTGAGCTGACTCAGGACCCTGATGTGTCCGTGGCCTTGGGACAG

ACAGTCAGGATCACATGCCAAGGAGACAGCCTCACCAGCTATTATGCA

AGCTGGTACCAGCAGAAGCCAGGACAGGCCCCTGTACTTGTCATCTCT

GGTAATGACAACCGGCCCTCAGGGATCCCAGACCGATTCTCTGGCTCC

AACTCAGGAAACACAGCTTCCTTGACCATCACTGGGGCTCAGGCGGAA
```

```
GATGCGGCTGACTATTACTGTGGCTCCCGGGACAGCAGCGGTTACCAA

GTGGTGTTCGGCGCAGGGACCAAGCTGACCGTCCTA

>CC21R3P1_B9 VL amino acid sequence
                                      (SEQ ID NO: 139)
SSELTQDPDVSVALGQTVRITCQGDSLTSYYASWYQQKPGQAPVLVIS

GNDNRPSGIPDRFSGSNSGNTASLTITGAQAEDAADYYCGSRDSSGYQ

VVFGAGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the B9 antibody have the following sequences: SYGMH (SEQ ID NO:34); VISYDGSNKYYADSVKG (SEQ ID NO:6); and DGGWYDWYFDL (SEQ ID NO:140). The light chain CDRs of the B9 antibody have the following sequences: QGDSLTSYYAS (SEQ ID NO:141); GNDNRPS (SEQ ID NO:142); and GSRDSSGYQVV (SEQ ID NO: 143).

An exemplary huIP-10 monoclonal antibody is the CC21R3P1_F1 ("CC_F1") antibody described herein. As shown below, the CC_F1 antibody includes a heavy chain variable region (SEQ ID NO:26) encoded by the nucleic acid sequence shown in SEQ ID NO:25, and a light chain variable region (SEQ ID NO:28) encoded by the nucleic acid sequence shown in SEQ ID NO:27.

```
>CC21R3P1_F1 VH nucleic acid sequence
                                      (SEQ ID NO: 25)
CAGGTGCAGCTGGTGGAGTCTGGGGGAGGCGTGGTCCAGCCTGGGAGG

TCCCACACACTCTCCTGTGCAGCCTCTGGATTCGCCTTCAAAAACTCT

GGCATACACTGGGTCCGCCAGGCTCCAGGCAAGGGACTGGAGTGGGTG

GCAGTTATATCATATGATGGAAGTAACAAATTCTACGCAGACTCCGTG

AAGGGCCGATTCACCATCTCCAGAGACAACTCCCAGAACACTGTATAT

CTGCAAATGACTGACCTGAGACCTGACGACACGGCTGTCTATTATTGT

GCAAGAGATGGGAGTGAGAGCGAGTACTTAGACTACTGGGGCAAGGGA

ACCCTGGTCACCGTCTCGAGT

>CC21R3P1_F1 VH amino acid sequence
                                      (SEQ ID NO: 26)
QVQLVESGGGVVQPGRSHTLSCAASGFAFKNSGIHWVRQAPGKGLEWV

AVISYDGSNKFYADSVKGRFTISRDNSQNTVYLQMTDLRPDDTAVYYC

ARDGSESEYLDYWGKGTLVTVSS

>CC21R3P1_F1 VL nucleic acid sequence
                                      (SEQ ID NO: 27)
AATTTTATGCTGACTCAGCCCCACTCTGTGTCGGAGTCTCCGGGGAAG

ACGGTGACCATCTCCTGCACCGGCAGCGGTGGCAGCATTGACAGAAAC

TATGTGCAGTGGTACCAGCAGCGCCCGGGCAGTGCCCCCATCACTGTG

ATCTATGAGGATAACCAAAGACCCTCTGGGGTCCCGGATCGATTCTCT

GGCTCCATCGACAGCTCCTCCAACTCTGCCTCCCTCACCATCTCTGGA

CTACGGACTGACGACGAGGCTGACTACTACTGTCAGTCTTATGATAGC

ATCAATCTTTGGGTTTTCGGCGGAGGGACCAAGGTCACCGTCCTAGG

>CC21R3P1_F1 VL amino acid sequence
                                      (SEQ ID NO: 28)
NFMLTQPHSVSESPGKTVTISCTGSGGSIDRNYVQWYQQRPGSAPITV

IYEDNQRPSGVPDRFSGSIDSSSNSASLTISGLRTDDEADYYCQSYDS

INLWVEGGGTKVTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the CC_F1 antibody have the following sequences: NSGIH (SEQ ID NO:5); VISYDGSNKFYADSVKG (SEQ ID NO:15); and DGSESEYLDY (SEQ ID NO:132). The light chain CDRs of the CC_F1 antibody have the following sequences: TGSGGSIDRNYVQ (SEQ ID NO:16); EDNQRPS (SEQ ID NO:9); and QSYDSINLWV (SEQ ID NO:29).

huIP-10 antibodies of the invention also include antibodies that include a heavy chain variable amino acid sequence that is at least 90%, 92%, 95%, 97%, 98%, 99% or more identical the amino acid sequence of SEQ ID NO: 2, 12, 18, 26, 31, 41, 51, 54, 61, 68, 75, 83, 92, 102, 109, 116, 123 or 137 and/or a light chain variable amino acid that is at least 90%, 92%, 95%, 97%, 98%, 99% or more identical the amino acid sequence of SEQ ID NO: 4, 14, 23, 28, 33, 43, 56, 63, 70, 77, 85, 94, 104, 111, 118, 125, 139 or 145.

Alternatively, the monoclonal antibody is an antibody that binds to the same epitope as NI-0801, C7, G11, B5, F3, CC_F1, B9, E5, H6, C5, D3, C3, F4, C1a, C1, E7, J9, CB_F1, A2 and/or G7.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, IgG and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, a scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM; e.g., $\leq 100$ nM, preferably $\leq 10$ nM and more preferably $\leq 200$ µM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an IP-10 epitope when the equilibrium binding constant ($K_d$) is $\leq$µM, e.g., $\leq 100$ nM, preferably $\leq 10$ nM, and more preferably 1 nM, as measured by assays such as radioligand binding assays or similar assays known to those skilled in the art. For example, the huIP-10 antibodies provided herein exhibit a IQ in the range approximately between $\leq 200$ pM to about 1 pM.

Those skilled in the art will recognize that it is possible to determine, without undue experimentation, if a human monoclonal antibody has the same specificity as a human monoclonal antibody of the invention (e.g., monoclonal antibody NI-0801, C7, G11, B5, F3, CB_F1, B9, E5, H6, C5, D3, C3, F4, C1a, C1, E7, J9, CC_F1, A1 or G7) by ascertaining whether the former prevents the latter from binding to a IP-10 antigen polypeptide. If the human monoclonal antibody being tested competes with a human monoclonal antibody of the invention, as shown by a decrease in binding by the human monoclonal antibody of the invention, then the two monoclonal antibodies bind to the same, or a closely related, epitope. Another way to determine whether a human monoclonal antibody has the specificity of a human monoclonal antibody of the invention is to pre-incubate the human monoclonal antibody of the invention with the IP-10 antigen polypeptide with which it is normally reactive, and then add the human monoclonal antibody being tested to determine if the human monoclonal antibody being tested is inhibited in its ability to bind the IP-10 antigen polypeptide. If the human monoclonal antibody being tested is inhibited then, in all likelihood, it has the same, or functionally equivalent, epitopic specificity as the monoclonal antibody of the invention.

Various procedures known within the art are used for the production of the monoclonal antibodies directed against a protein such as an IP-10 protein, or against derivatives, fragments, analogs homologs or orthologs thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies are prepared, for example, using the procedures described in the Examples provided below. Human monoclonal antibodies can be also prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

It is desirable to modify the antibody of the invention with respect to effector function, so as to enhance, e.g., the effectiveness of the antibody in treating immune-related diseases. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also includes $F_v$, $F_{ab}$, $F_{ab'}$ and $F_{(ab)2}$ huIP-10 fragments, single chain huIP-10 antibodies, bispecific huIP-10 antibodies and heteroconjugate huIP-10 antibodies.

Bispecific antibodies are antibodies that have binding specificities for at least two different antigens. In the present case, one of the binding specificities is for IP-10. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

Other approaches for generating bispecific antibodies are described, e.g., in WO 96/27011, which is hereby incorporated by reference in its entirety. Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. See e.g., Brennan et al., Science 229:81 (1985), which is hereby incorporated by reference in its entirety.

Additionally, Fab' fragments can be directly recovered from E. coli and chemically coupled to form bispecific antibodies. See e.g., Shalaby et al., J. Exp. Med. 175:217-225 (1992), which is hereby incorporated by reference in its entirety.

Various techniques for making and isolating bispecific antibody fragments directly from recombinant cell culture have also been described. For example, bispecific antibodies have been produced using leucine zippers. See e.g., Kostelny et al., J. Immunol. 148(5):1547-1553 (1992), which is hereby incorporated by reference in its entirety. The "diabody" technology described by Hollinger et al., Proc. Natl. Acad. Sci. USA 90:6444-6448 (1993), which is hereby incorporated by reference in its entirety, has provided an alternative mechanism for making bispecific antibody fragments. Another strategy for making bispecific antibody fragments by the use of single-chain Fv (sFv) dimers has also been reported. See, Gruber et al., J. Immunol. 152:5368 (1994), which is hereby incorporated by reference in its entirety.

Antibodies with more than two valencies are contemplated. For example, trispecific antibodies can be prepared. See, Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, IFNγ, CD28, or B7), or Fc receptors for IgG (FcγR), such as FcγRI (CD64), FcγRII (IFNγ2) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (DAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling is accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding is achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Preferred polypeptides in accordance with the invention comprise the human heavy chain immunoglobulin molecules presented herein and the human light chain immunoglobulin molecules presented herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end the lefthand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative.

Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to IP-10, under suitable binding conditions or (2) ability to block appropriate IP-10 binding. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $-CH_2NH-$, $-CH_2S-$, $-CH_2-CH_2-$, $-CH=CH-$ (cis and trans), $-COCH_2-$, $CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects. The term subject includes humans and other mammals.

Human Antibodies and Humanization of Antibodies

A huIP-10 antibody is generated, for example, using the procedures described in the Examples provided below. An IgG huIP-10 antibody is generated, for example, by converting a scFv clone an IgG format (see e.g., Example 9). For example, huIP-10 antibodies are reformatted into an IgG1 isotype.

In other, alternative methods, a huIP-10 antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of IP-10 or fragments thereof. In another approach, a huIP-10 antibody can be produced by a process wherein at least one step of the process includes immunizing a transgenic, non-human animal with human IP-10 protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and No. 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against IP-10 in order to vitiate concerns and/or effects of HAMA or HACA response.

The production of antibodies with reduced immunogenicity is also accomplished via humanization and display techniques using appropriate libraries. It will be appreciated that murine antibodies or antibodies from other species can be humanized or primatized using techniques well known in the art See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101, 5,585,089, 5,693,761, 5,693,792, 5,714, 350, and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as priers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL-31 sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright and Harris, supra., Hanes and Plucthau PEAS USA 94:4937-4942 (1997) (ribosomal display), Parmley and Smith Gene 73:305-318 (1988) (phage display), Scott TIB5 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to IP-10 expressing cells, IP-10 itself, forms of IP-10, epitopes or peptides thereof, and expression libraries thereto (See e.g., U.S. Pat. No. 5,703,057) which can thereafter be screened as described above for the activities described above.

Design and Generation of Other Therapeutics

In accordance with the present invention and based on the activity of the antibodies that are produced and characterized herein with respect to IP-10, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies one with a specificity to IP-10 and another to a second molecule that are conjugated together, (ii) a single antibody that has one chain specific to IP-10 and a second chain specific to a second molecule, or (iii) a single chain antibody that has specificity to IP-10 and the other molecule. Such bispecific antibodies are generated using techniques that are well known for example, in connection with (i) and (ii) See e.g., Fanger et al. Immunol Methods 4:72-81 (1994) and Wright and Harris, supra, and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing IP-10, and particularly those cells in which the antibodies of the invention are effective.

In connection with the generation of therapeutic peptides, through the utilization of structural information related to IP-10 and antibodies thereto, such as the antibodies of the invention or screening of peptide libraries, therapeutic peptides can be generated that are directed against IP-10. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the IP-10 molecule (or a form, such as a splice variant or alternate form) is functionally active in a disease process, it will also be possible to design gene and antisense therapeutics thereto through conventional techniques. Such modalities can be utilized for modulating the function of IP-10. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the IP-10 molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of IP-10. Such structures can be synthesized chemically or expressed in biological systems. This approach has been reviewed in Capsey et al. Genetically Engineered Human Therapeutic Drugs (Stockton Press, NY (1988)). Further, combinatorial libraries can be designed and synthesized and used in screening programs, such as high throughput screening efforts.

Therapeutic Administration and Formulations

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The huIP-10 antibodies and therapeutic formulations of the invention, which include a huIP-10 antibody of the invention, are used to treat or alleviate a symptom associated with an immune-related disorder, such as, for example, an autoimmune disease or an inflammatory disorder.

Autoimmune diseases include, for example, Acquired Immunodeficiency Syndrome (AIDS, which is a viral disease with an autoimmune component), alopecia greata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiffman syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The huIP-10 antibodies modulate an immune response in a subject, e.g., in a human subject. In one embodiment, the huIP-10 antibody compositions used to treat an immune-related disorder are administered in combination with any of a variety of anti-cytokine agents or anti-chemokine agents. Suitable anti-cytokine or anti-chemokine reagents recognize, for example, cytokines such as interleukin 1 (IL-1), IL-2, IL-4, IL-6, IL-12, IL-13, IL-15, IL-17, IL-18, IL-20, IL-21, IL-22, IL-23, IL-27 and IL-31, and/or chemokines such as MIP1 alpha, MIP1 beta, RANTES, MCP1, IP-10, ITAC, MIG, SDF and fractalkine.

In one embodiment, the huIP-10 antibodies and the huIP-10 antibody compositions used to treat an immune-related disorder are administered in conjunction with one or more additional agents, or a combination of additional agents. For example, the huIP-10 antibody and additional agent are formulated into a single therapeutic composition, and the huIP-10 antibody and additional agent are administered simultaneously. Alternatively, the huIP-10 antibody and additional agent are separate from each other, e.g., each is formulated into a separate therapeutic composition, and the huIP-10 antibody and the additional agent are administered simultaneously, or the huIP-10 antibody and the additional agent are administered at different times during a treatment regimen. For example, the huIP-10 antibody is administered prior to the administration of the additional agent, the huIP-10 antibody is administered subsequent to the administration of the additional agent, or the huIP-10 antibody and the additional agent are administered in an alternating fashion. As described herein, the huIP-10 antibody and additional agent are administered in single doses or in multiple doses.

For example, in the treatment of multiple sclerosis, the huIP-10 antibody, or therapeutic formulation thereof, is administered in conjunction with one or more additional agents such as interferon beta 1a, interferon beta 1b, glatiramer acetate, natalizumab, copaxone, and combinations thereof. The huIP-10 antibody and the additional agent are administered simultaneously, or the huIP-10 antibody and the additional agent are administered at different times during a treatment regimen.

In the treatment of Crohn's disease, the huIP-10 antibody, or therapeutic formulation thereof, is administered in conjunction with one or more additional agents such as an antibiotic, an aminosalicylate, Infliximab, Adalimumab, and combinations thereof. Suitable antibiotics include, e.g., metronidazole and/or ciprofloxacin. Suitable aminosalicylates include, for example, mesalamine and/or sulfasalazine. The huIP-10 antibody and the additional agent are administered simultaneously, or the huIP-10 antibody and the additional agent are administered at different times during a treatment regimen.

In the treatment of ulcerative colitis, the huIP-10 antibody, or therapeutic formulation thereof, is administered in conjunction with one or more additional agents such as 6-mercaptopurine, azathioprine, Infliximab and combinations thereof. The huIP-10 antibody and the additional agent are administered simultaneously, or the huIP-10 antibody and the additional agent are administered at different times during a treatment regimen.

In the treatment of psoriasis, the huIP-10 antibody, or therapeutic formulation thereof, is administered in conjunction with one or more additional agents such as alefacept, efalizumab, Adalimumab, Infliximab, cyclosporine, Methotrexate, and combinations thereof. The huIP-10 antibody and the additional agent are administered simultaneously, or the huIP-10 antibody and the additional agent are administered at different times during a treatment regimen.

In the treatment of atherosclerosis, the huIP-10 antibody, or therapeutic formulation thereof, is administered in conjunction with one or more additional agents such as warfarin, a cholesterol lowering drug, and combinations thereof. Suitable cholesterol lowering drugs include, for example, statins and fibrates. The huIP-10 antibody and the additional agent are administered simultaneously, or the huIP-10 antibody and the additional agent are administered at different times during a treatment regimen.

The huIP-10 antibodies and therapeutic formulations thereof are used in methods of treating or alleviating a symptom associated with an immune-related disorder. For example, the compositions of the invention are used to treat or alleviate a symptom of any of the autoimmune diseases and inflammatory disorders described herein. Symptoms associated with immune-related disorders include, for example, inflammation, fever, loss of appetite, weight loss, abdominal symptoms such as, for example, abdominal pain, diarrhea or constipation, joint pain or aches (arthralgia), fatigue, rash, anemia, extreme sensitivity to cold (Raynaud's phenomenon), muscle weakness, muscle fatigue, changes in skin or tissue tone, shortness of breath or other abnormal breathing patterns, chest pain or constriction of the chest muscles, abnormal heart rate (e.g., elevated or lowered), light sensitivity, blurry or otherwise abnormal vision, and reduced organ function.

The huIP-10 antibody and therapeutic formulations thereof are administered to a subject suffering from an immune-related disorder, such as an autoimmune disease or an inflammatory disorder. A subject suffering from an autoimmune disease or an inflammatory disorder is identified by methods known in the art. For example, subjects suffering from an autoimmune disease such as Crohn's disease, lupus or psoriasis, are identified using any of a variety of clinical and/or laboratory tests such as, physical examination, radiologic examination and blood, urine and stool analysis to evaluate immune status. For example, patients suffering from lupus are identified, e.g., by using the anti-nuclear antibody test (ANA) to determine if auto-antibodies to cell nuclei are present in the blood. Patients suffering from Crohn's are identified, e.g., using an upper gastrointestinal (GI) series and/or a colonoscopy to evaluate the small and large intestines, respectively. Patients suffering from psoriasis are identified, e.g., using microscopic examination of tissue taken from the affected skin patch, while patients suffering from rheumatoid arthritis are identified using, e.g., blood tests and/or x-ray or other imaging evaluation. Patients suffering from atherosclerosis are identified, e.g., using blood tests, electrocardiograms (ECG), stress testing, coronary angiography, ultrasound, and computed tomography (CT).

Administration of a huIP-10 antibody to a patient suffering from an immune-related disorder such as an autoimmune disease or an inflammatory disorder is considered successful if any of a variety of laboratory or clinical results is achieved. For example, administration of a huIP-10 antibody to a patient suffering from an immune-related disorder such as an autoimmune disease or an inflammatory disorder is considered successful one or more of the symptoms associated with the disorder is alleviated, reduced, inhibited or does not progress to a further, i.e., worse, state. Administration of a huIP-10 antibody to a patient suffering from an immune-related disorder such as an autoimmune disease or an inflammatory disorder is considered successful if the disorder, e.g., an autoimmune disorder, enters remission or does not progress to a further, i.e., worse, state.

Diagnostic and Prophylactic Formulations

The fully human anti-IP-10 MAbs of the invention are used in diagnostic and prophylactic formulations. In one embodiment, a huIP-10 MAb of the invention is administered to patients that are at risk of developing one of the aforementioned autoimmune diseases. A patient's predisposition to one or more of the aforementioned autoimmune diseases can be determined using genotypic, serological or biochemical markers.

In another embodiment of the invention, a huIP-10 antibody is administered to human individuals diagnosed with one or more of the aforementioned autoimmune diseases. Upon diagnosis, a huIP-10 antibody is administered to mitigate or reverse the effects of autoimmunity.

Antibodies of the invention are also useful in the detection of IP-10 in patient samples and accordingly are useful as diagnostics. For example, the huIP-10 antibodies of the invention are used in in vitro assays, e.g., ELISA, to detect IP-10 levels in a patient sample.

In one embodiment, a huIP-10 antibody of the invention is immobilized on a solid support (e.g., the well(s) of a microtiter plate). The immobilized antibody serves as a capture antibody for any IP-10 that may be present in a test sample. Prior to contacting the immobilized antibody with a patient sample, the solid support is rinsed and treated with a blocking agent such as mink protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of IP-10 antigen in the test sample is determined by comparison with a standard curve developed from the standard samples.

It will be appreciated that based on the results obtained using the huIP-10 antibodies of the invention in an in vitro diagnostic assay, it is possible to stage a disease (e.g., an autoimmune or inflammatory disorder) in a subject based on expression levels of the IP-10 antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Cloning, Expression and Purification of Human IP-10

Cloning

The gene encoding the mature protein human IP-10 (hIP10) (NM001565) was cloned in an expression plasmid pET43 (Novagen Madison, Wis.) by PCR amplification. The sequence for the Factor X protease cleavage site was introduced at the C-terminus of NusA. The sequence for the Avi-Tag (Avidity, Denver Colo.) biotinylation site was introduced at the C-terminus of the chemokine coding sequence. The pET-derived plasmids were used for the co-transformation of bacterial strain Origami B with pACYC184-BirA plasmid that encodes the biotin ligase gene.

Expression of NusA-hIP-10 Fusion Protein

An overnight culture of bacteria harboring the expression construct was diluted 1:30 into Terrific broth (InvitroGen) containing 50 µg/mL Ampicillin, 10 µg/mL Kanamicin, 5 µg/mL Tetracycline, 20 µg/mL Chloramphenicol and 50 µM Biotin. The culture was incubated at 37° C. with shaking until OD 600=0.7 was reached. IPTG was then added to a final concentration of 1 mM, incubated for 15 min. at 37° C. and overnight at 25° C.

Purification and Cleavage of Fusion Proteins

Bacterial pellets were resuspended in Bugbuster (Novagen) containing Benzonase Nuclease and protease inhibitor Complete EDTA-free (Roche) and incubated for 1 hour at 4° C. The soluble and insoluble fractions were separated by centrifugation at 10,000 g for 15 min at 4° C. Soluble and insoluble protein fractions were analyzed by SDS-PAGE (Novex gels, InvitroGen). The soluble fraction was diluted 1/2 with Buffer A (Tris-HCl 100 mM pH 8.0, NaCl 600 mM, $CaCl_2$ 10 mM, Imidazole 40 mM), mixed with 50% (v/v) Ni-NTA agarose (Qiagen) previously equilibrated in Buffer B (Tris-HCl 50 mM pH 8.0, NaCl 300 mM, $CaCl_2$ 5 mM, Imidazole 20 mM). The mixture was incubated for 30 min at RT with gentle shaking. The beads obtained after centrifugation were loaded in Poly-Prep chromatography columns (Biorad), washed three times with 5 volumes of Buffer B and eluted with Buffer C (Tris-HCl 50 mM pH 8.0, NaCl 200 mM, $CaCl_2$ 5 mM, Imidazole 400 mM). Elution fractions containing the protein were pooled and desalted using PD-10 columns (Amersham). NusA-chemokine fusion proteins were cleaved by Factor X (Novagen, Madison, Wis.) by incubating 1 mg protein with 25 U Factor X at 30° C. for up to 24 h in cleavage buffer (Tris-HCl 50 mM pH 8.0, NaCl 200 mM, $CaCl_2$ 5 mM). For some of the fusions proteins, the parameters for optimal cleavage were slightly different but were easily determined by varying incubation time (4-24 h) and/or temperature (25-37° C.). The cleaved protein was analyzed by SDS-PAGE and the activity tested by chemotaxis.

Example 2

Cloning, Expression of hCXCR3, the Receptor of hIP-10

A murine pre B lymphoma L1.2 cell line that stably expresses a chemokine receptor was generated by transfection. The cDNA encoding hCXCR3 was cloned by PCR using lymph node cDNA (Clontech, Palo Alto, Calif.) as a template. The PCR product was digested with Xba I and Not I and ligated into mammalian expression vector pcDNA 3.1-C (In-vitrogen) The sequence of the coding region of the receptor was verified by sequencing. L1.2 cells ($5 \times 10^6$) were transfected by electroporation with 20 µg of linearized CXCR3 expression plasmid. Stable clones of receptor-expressing L1.2 cells were established by limiting dilution in the presence of 1 mg/mL Geneticin.

Receptor expression level was determined by flow cytometry (FACScan, Becton Dickinson, Mountain View, Calif.) using monoclonal antibody directed against hCXCR3 (Sigma, St. Louis, Mo.).

Example 3

Production of Native Human IP-10

THP1 cells were cultured in 10 ml media at a concentration at $1 \times 10^6$/ml with 50 ng/ml recombinant human interferon gamma (IFNγ). Following overnight incubation at 37° C., cells were centrifuged, supernatant was collected and the concentration of IP-10 calculated via an ELISA assay.

Example 4

Cells Expressing Human IP-10 on Cell Surface

Chinese hamster ovary (CHO) cells (available from American Type Culture Collection (ATCC)) were stably transfected with c-myc-tagged human IP-10 cDNA that was subcloned into pcDNA 3.1 plasmids (Invitrogen, Carlsbad Calif.) containing neomycin resistance genes. Transfectants were selected by using this antibiotic, and successive cell sorting was accomplished by flow cytometry using an anti-6xHis (Sigma) antibody. Surface expression of human IP-10 was confirmed via flow cytometry using an anti-IP-10 mAb 266 (R&D Systems, Minneapolis Minn.).

Example 5

Screening of Human scFv Libraries

General procedures for construction and handling of human scFv libraries are described in Vaughan et al., (Nat. Biotech. 1996, 14:309-314), hereby incorporated by reference in its entirety. Libraries of human scFv were screened against hIP-10 according to the following procedure.

Liquid Phase Selections.

Aliquots of scFv phage libraries ($10^{12}$ Pfu) obtained from Cambridge Antibody Technology (Cambridge, UK) were blocked with PBS containing 3% (w/v) skimmed milk for one hour at room temperature on a rotary mixer. Blocked phage was then deselected on streptavidin magnetic beads (Dynal M-280) for one hour at room temperature on a rotary mixer. Deselected phage was then incubated with in vivo biotinylated hIP-10 (100 nM) for two hours at room temperature on a rotary mixer. This selection step was performed either on NusA-hIP-10 biotinylated fusion protein or on biotinylated-hIP-10 released from the fusion by proteolytic cleavage. Beads were captured using a magnetic stand followed by four washes with PBS/0.1% Tween 20 and 3 washes with PBS. Beads were then directly added to 10 ml of exponentially growing TG1 cells and incubated for one hour at 37° C. with slow shaking (100 rpm). An aliquot of the infected TG1 was serial diluted to titer the selection output. The remaining infected TG1 were spun at 3000 rpm for 15 minutes and re-suspended in 0.5 ml 2xTY-AG (2xTY media containing 100 µg/ml ampicillin and 2% glucose) and spread on 2xTYAG agar Bioassay plates. After overnight incubation at 30° C. 10 ml of 2xTYAG was added to the plates and the cells were scraped form the surface and transferred to a 50 ml polypropylene tube. 2×TYAG containing 50% glycerol was added to the cell suspension to obtain a final concentration of 17% glycerol. Aliquots of the selection round were kept at −80° C.

Cell Surface Selections.

Aliquots of scFv phage libraries ($10^{12}$ Pfu) obtained from Cambridge Antibody Technology (Cambridge, UK) were blocked with PBS containing 3% (w/v) skimmed milk for one hour at room temperature on a rotary mixer. Blocked phage was then deselected for one hour at 37° C./5% $CO_2$ on CHO cells transfected with an empty pDisplay vector (in a T75 flask 80% confluence) and that had been previously blocked with PBS containing 2% (w/v) skimmed milk. Deselected phage was then incubated CHO-pDisplay-hIFNγ cells for one hour at room temperature with gentle shaking. Cells were then washed ten times with PBS. Bound phage was eluted by adding directly 10 ml of exponentially growing TG1 to the T75 flask and incubating for one hour at 37° C. with slow shaking. An aliquot of the infected TG1 was serial diluted to titer the selection output. Infected TG1 were spun at 3000 rpm for 15 minutes and re-suspended in 0.5 ml 2×TY-AG (2×TY media containing 100 μg/ml ampicilin and 2% glucose) and spread on 2×TYAG agar Bioassay plates. After overnight incubation at 30° C. 10 ml of 2×TYAG was added to the plates and the cells were scraped form the surface and transferred to a 50 ml polypropylene tube. 2×TYAG containing 50% glycerol was added to the cell suspension to obtain a final concentration of 17% glycerol. Aliquots of the selection round were kept at −80° C.

Phage Rescue.

100 μl of cell suspension obtained from previous selection rounds were added to 20 ml of 2×TYAG and grown at 37° C. with agitation (240 rpm) until an $OD_{600}$ of 0.3 to 0.5 was reached. The culture was then super-infected with $3.3 \times 10^{10}$ MK13K07 helper phage and incubated for one hour at 37° C. (150 rpm). The medium was then changed by centrifugating the cells at 2000 rpm for 10 minutes, removing the medium and resuspending the pellet in 20 ml of 2×TY-AK (100 mg/ml ampicillin; 50 μg/ml kanamycin). The culture was then grown overnight at 30° C. (240 rpm).

Monoclonal Phage Rescue for ELISA.

Single clones were picked into a microtiter plate containing 150 μl of 2×TYAG media (2% glucose) per well and grown at 37° C. (100-120 rpm) for 5-6 h. M13K07 helper phage was added to each well to obtain a multiplicity of infection (MOI) of 10 (i.e., 10 phage for each cell in the culture) and incubated at 37° C. (100 rpm) for 1 h. Following growth, plates were centrifuged at 3,200 rpm for 10 min. Supernatant was carefully removed, cells re-suspended in 150 μl 2×TYAK medium and grown overnight at 30° C. (120 rpm). For the ELISA, the phage are blocked by adding 150 μl of 2× concentration PBS containing 5% skimmed milk powder followed by one hour incubation at room temperature. The plates were then centrifuged 10 minutes at 3000 rpm and the phage containing supernatant used for the ELISA.

Phage ELISA.

ELISA plates (Maxisorb, NUNC) were coated overnight with 2 μg/ml hIFNγ in PBS. Control plates were coated with 2 μg/ml BSA. Plates were then blocked with 3% skimmed milk/PBS at room temperature for 1 h. Plates were washed 3 times with PBS 0.05% Tween 20 before transferring the pre-blocked phage supernatants and incubation for one hour at room temperature. Plates were then washed 3 times with PBS 0.05% Tween 20. 50 μl of 3% skimmed milk/PBS containing (HRP)-conjugated anti-M13 antibody (Amersham, diluted 1:10,000) to each well. Following incubation at room temperature for 1 hr, the plates were washed 5 times with PBS 0.05% Tween 20. The ELISA was then revealed by adding 500 of TMB (Sigma) and 50 μl of $2NH_2SO_4$ to stop the reaction. Absorption intensity was read at 450 nm.

Phage Clone Sequencing

Single clones were placed in a microtiter plate containing 150 μl of 2×TYAG media (2% glucose) per well and grown at 30° C. (120 rpm) overnight. The next day 5 μl of culture was transferred into another plate containing 45 μl of $dH_2O$ and mixed. The plates was then frozen at −20° C. After thawing, 1 μl of this suspension was used for PCR amplification using standard PCR protocols with primer specific for pCANTAB6: mycseq, 5'-CTCTTCTGAGATGAGTTTTTG-3' (SEQ ID NO: 130) and gene3leader, 5'-TTATTATTCG-CAATTCCTTTAGTTGTTCCT-3' (SEQ ID NO: 131).

The PCR reactions were purified in 96 well format using the Montage PCRμ96 system (Millipore). 5 μl of the eluted DNA was sequencing using the mycseq and gene3leader primers.

ScFv Periplasmic Preparation for Functional Tests.

Individual clones were inoculated into a deep well microtiter plate containing 0.9 ml of 2×TYAG media (0.1% glucose) per well and grown at 37° C. for 5-6 h (250 rpm). 100 μl per well of 0.2 mM IPTG in 2×TY medium were then added to give a final concentration of 0.02 mM IPTG. Plates were then incubated overnight at 30° C. with shaking at 250 rpm. The deep-well plates were centrifuged at 2,500 rpm for 10 min and the supernatant carefully removed. The pellets were re-suspended in 150 μl TES buffer (50 mM Tris/HCl (pH 8), 1 mM EDTA (pH 8), 20% sucrose, complemented with Complete protease inhibitor, Roche). A hypotonic shock was produced by adding 150 μl of diluted TES buffer (1:5 TES:water dilution) and incubation on ice for 30 min. Plates were then centrifuged at 4000 rpm for 10 minutes to remove cells and debris. The supernatants were carefully transferred into another microtiter plate and kept on ice for immediate testing in functional assays or ELISAs.

Large Scale scFv Purification

A starter culture of 1 ml of 2×TYAG was inoculated with a single colony from a freshly streaked 2×TYAG agar plate and incubated with shaking (240 rpm) at 37° C. for 5 hours. 0.9 ml of this culture was used to inoculate a 400 ml culture of the same media and was grown overnight at 30° C. with vigorous shaking (300 rpm).

The next day the culture was induced by adding 400 μl of 1M IPTG and incubation was continued for an additional 3 hours. The cells were collected by centrifugation at 5,000 rpm for 10 minutes at 4° C. Pelleted cells were resuspended in 10 ml of ice-cold TES buffer complemented with protease inhibitors as described above. Osmotic shock was achieved by adding 15 ml of 1:5 diluted TES buffer and incubation for 1 hour on ice. Cells were centrifuged at 10,000 rpm for 20 minutes at 4° C. to pellet cell debris. The supernatant was carefully transferred to a fresh tube. Imidazole was added to the supernatant to a final concentration of 10 mM. 1 ml of Ni-NTA resin (Qiagen), equilibrated in PBS was added to each tube and incubated on a rotary mixer at 4° C. (20 rpm) for 1 hour.

The tubes were centrifuged at 2,000 rpm for 5 minutes and the supernatant carefully removed. The pelleted resin was resuspended in 10 ml of cold (4° C.) Wash buffer 1 (50 mM $NaH_2PO_4$, 300 mM NaCl, 10 mM imidazole, pH to 8.0). The suspension was added to a polyprep column (Biorad). 8 ml of cold Wash Buffer 2 (50 mM $NaH_2PO_4$, 300 mM NaCl, 20 mM imidazole, pH to 8.0) were used to wash the column by gravity flow. The scFv were eluted from the column with 2 ml of Elution buffer (50 mM $NaH_2PO_4$, 300 mM NaCl, 250 mM imidazole, pH to 8.0). Fractions were analyzed by absorption at 280 nm and protein containing fractions were pooled before buffer exchange on a PD10 desalting column (Amersham) equilibrated with PBS. The scFv in PBS were analyzed by SDS-PAGE and quantified by absorption at 280 nm. The purified scFv were aliquoted and stored at −20° C. and at 4° C.

Example 6

Inhibition of hIP-10 Induced Calcium Flux Using scFv Extracts

Periplasmic extracts of various hIP-10 scFv were produced as described above. L1.2 cells expressing hCXCR3 were cultured in RPMI medium supplemented with 10% FCS. Extracts containing the scFv were incubated with 2-10 nM of hIP-10 (Peprotech, Rocky Hill N.J.) for 30 minutes at room temperature. Cells were washed in PBS and loaded with 2 µM Fura 2/AM. 100 µl of loaded cells were added to each well of a 96-well black, transparent flat-bottom plate and calcium flux kinetics were recorded by measuring the fluorescence at 514 nm upon excitation at 340 or 380 nm on a Flex station II instrument (Molecular Devices). The inhibitory activity of each scFv extract was assessed by comparison to an extract containing an irrelevant scFv. The positive scFv candidates were expressed in larger scale as described above in Example 5 and confirmed in dose-response experiments in calcium flux assays (Table 4).

TABLE 4

Potency of antibodies tested in scFv format in chemotaxis and calcium flux functional assays. Chemotaxis was performed using either 2 nM (¶), 1 nM, or 0.2 nM (§) of hIP-10, while calcium flux was induced with 10 nM of hIP-10. Antibodies in the top part of the table were obtained after affinity maturation.

| Clone ID | Chemotaxis IC$_{50}$ (nM) | Calcium flux IC$_{50}$ (nM) |
| --- | --- | --- |
| CF1N1R3P4_C7 | 0.12§ | ND |
| CF1H1R3P3_G11 | 0.39§ | 7.8 |
| CF1H1R3P4_B5 | 0.51§ | 2.4 |
| CF1A11R3P3_F3 | 1.8 | 14 |
| CE7C1R3H8_J9 | 0.9 | ND |
| CC21R3P1_F1 | 18¶ | 36 |
| CC21R3P1_B9 | 107 | 107 |
| CB21R3P3_E5 | 36¶ | 39 |
| CC21R3P1_H6 | 36 | 71 |
| CC21R3P5_C5 | 90 | 89 |
| CB1R3P4_D3 | 72 | 179 |
| CB2R2P4_C3 | 15 | 14 |
| CC21R3P4_F4 | 36 | 107 |
| CC21R3P1_C1a | 108 | 37 |
| CC21R3P3_C1 | 72 | 71 |
| CC21R3P1_E7 | 71¶ | 250 |
| CB21R3P1_F1 | 40¶ | 36 |
| CC21R3P1_A2 | 7 | 36 |
| CB21R3P6_G7 | 10 | 46 |

Example 7 scFv Inhibition of hIP-10-Induced Cell Chemotaxis

Wild type L1.2 cells and L1.2 cells expressing hCXCR3 were cultured in RPMI medium supplemented with 10% FCS. The day before the experiment cells were incubated with 0.6 mg/ml of butyric acid. Different concentrations of purified scFv were incubated with 0.2-10 nM rhIP-10 and placed in the bottom chamber of chemotaxis 96-well plate (Neuroprobe). The filter plate was placed on top of the chemotaxis plate and each well was overlaid with 20 µl of a $10^6$ cells/ml suspension. The plate was incubated for 2 hours at 37° C. Cells that migrated through the filter were stained with DRAQ5 (Alexis Corporation) and counted on an FMAT 8200 reader (Applied Biosystems, Foster City Calif.). The IC$_{50}$ (where 50% of the hIP-10 induced cell migration is inhibited, i.e., 50% inhibitory concentration), for each candidate antibody was determined (Table 4).

Example 8

Reformatting scFv into IgG Format

The V$_H$ and V$_L$ sequence of selected scFv were amplified with specific oligonucleotides introducing a leader sequence and a HindIII restriction site at the 5' end. An ApaI or an AvrII site was introduced at the 3' end of the heavy and light chain sequence, respectively. The amplified V$_H$ sequences were digested HindIII/ApaI and cloned into the pCon_gamma1 expression vector (LONZA, Basel, Switzerland). The amplified V$_L$ sequences were digested HindIII/AvrII and cloned into the pCon_lambda2 expression vector (LONZA). The constructions were verified by sequencing before transfection into mammalian cells.

The V$_H$ and V$_L$ cDNA sequences in their appropriate expression vectors were transfected into mammalian cells using the Fugene 6 Transfection Reagent (Roche, Basel, Switzerland). Briefly, Peak cells were cultured in 6-well plates at a concentration of 6×$10^5$ cells per well in 2 ml culture media containing fetal bovine serum. The expression vectors, encoding the candidate V$_H$ and V$_L$ sequences, were co-transfected into the cells using the Fugene 6 Transfection Reagent according to manufacturer's instructions. One day following transfection, the culture media was aspirated, and 3 ml of fresh serum-free media was added to cells and cultured for three days at 37° C. Following three days culture period, the supernatant was harvested for IgG purified on protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE.

The nucleic acid and amino acid sequences of the IgG1 reformatted NI-0801 antibody is shown below:

>NI-0801 Light Chain Amino Acid Sequence
(SEQ ID NO: 134)
NFMLTQPHSVSESPGKTVTISCTGSGGSIASNYVQWYQQRPGSSPTTV

IYEDNQRPSGVPDRFSGSIDSSSNSASLTISGLKTEDEADYYCQSYDP

LPVWVFGGGTKLTVLGQPKAAPSVTLFPPSSEELQANKATLVCLISDF

YPGAVTVAWKADSSPVKAGVETTTPSKQSNNKYAASSYLSLTPEQWKS

HRSYSCQVTHEGSTVEKTVAPTECS

>NI-0801 Heavy Chain Amino Acid Sequence
(SEQ ID NO: 135)
QVQLVESGGGVVQPGRSLRLSCAASGFTFSNSGIHWVRQAPGKGLEWV

AVISYDGSNKYYADSVKGRFTISRDNSKNTLYLQMNSLRAEDTAVYYC

ARLRDNAEYTDYWGQGTLVTVSSASTKGPSVFPLAPSSKSTSGGTAAL

-continued

GCLVKDYFPEPVTVSWNSGALTSGVHTFPAVLQSSGLYSLSSVVTVPS

SSLGTQTYICNVNHKPSNTKVDKRVEPKSCDKTHTCPPCPAPELLGGP

SVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHE

ALHNHYTQKSLSLSPGK

Example 9

Figure 1B:
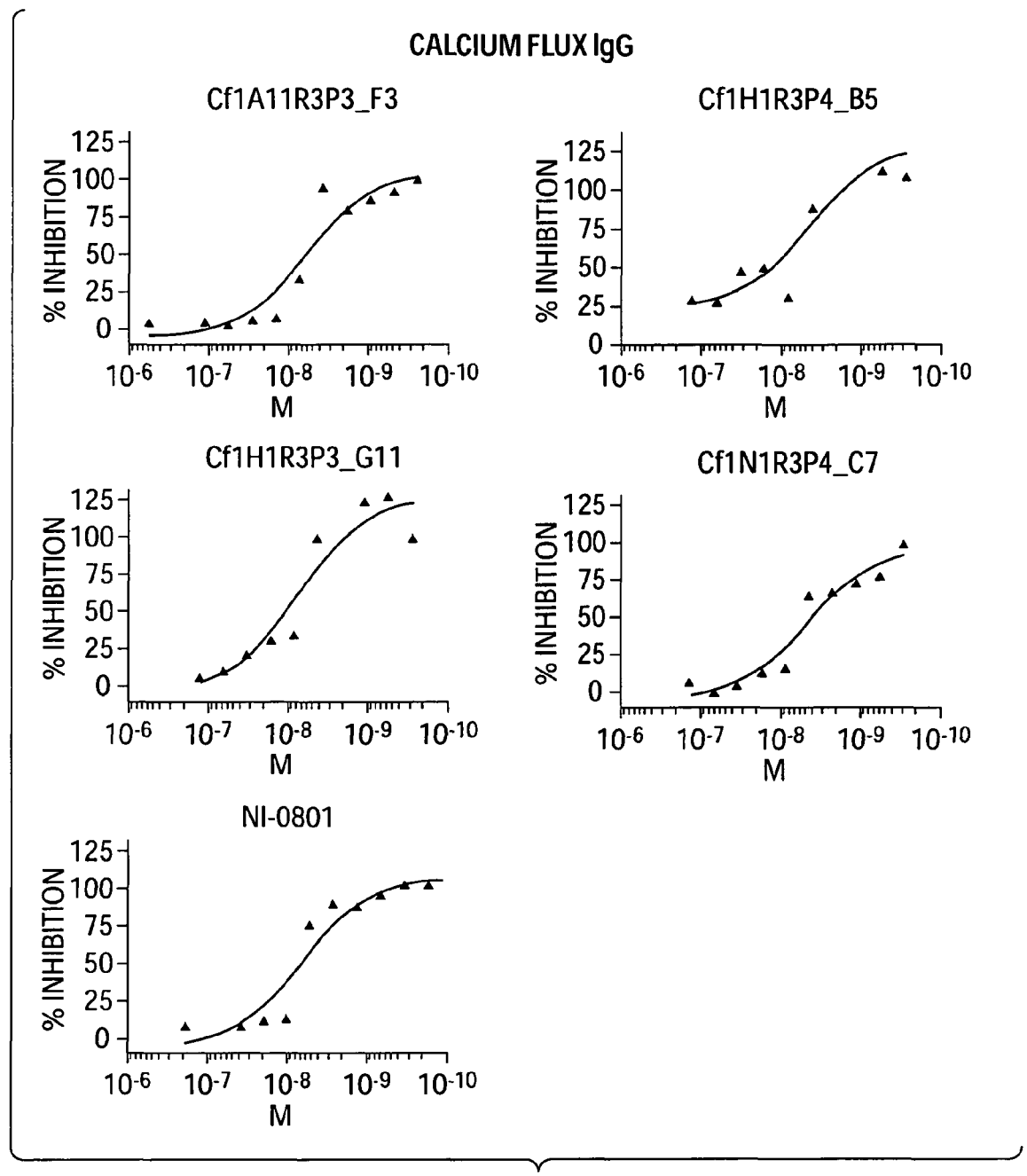
Figure 2A:
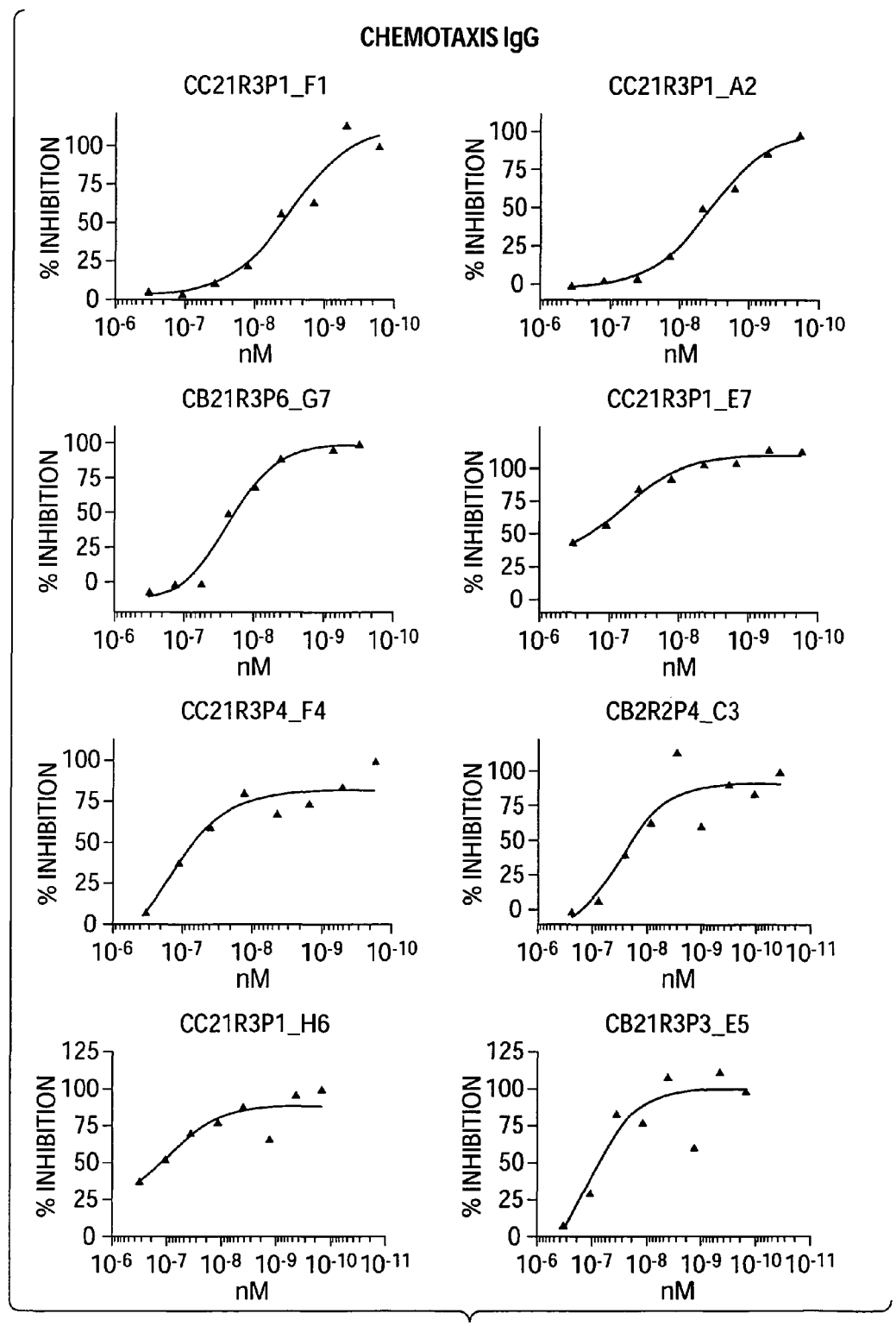
FIGS. 2A-2B depict the dose-dependent neutralizing activity on recombinant hIP-10.
Figure 2B:
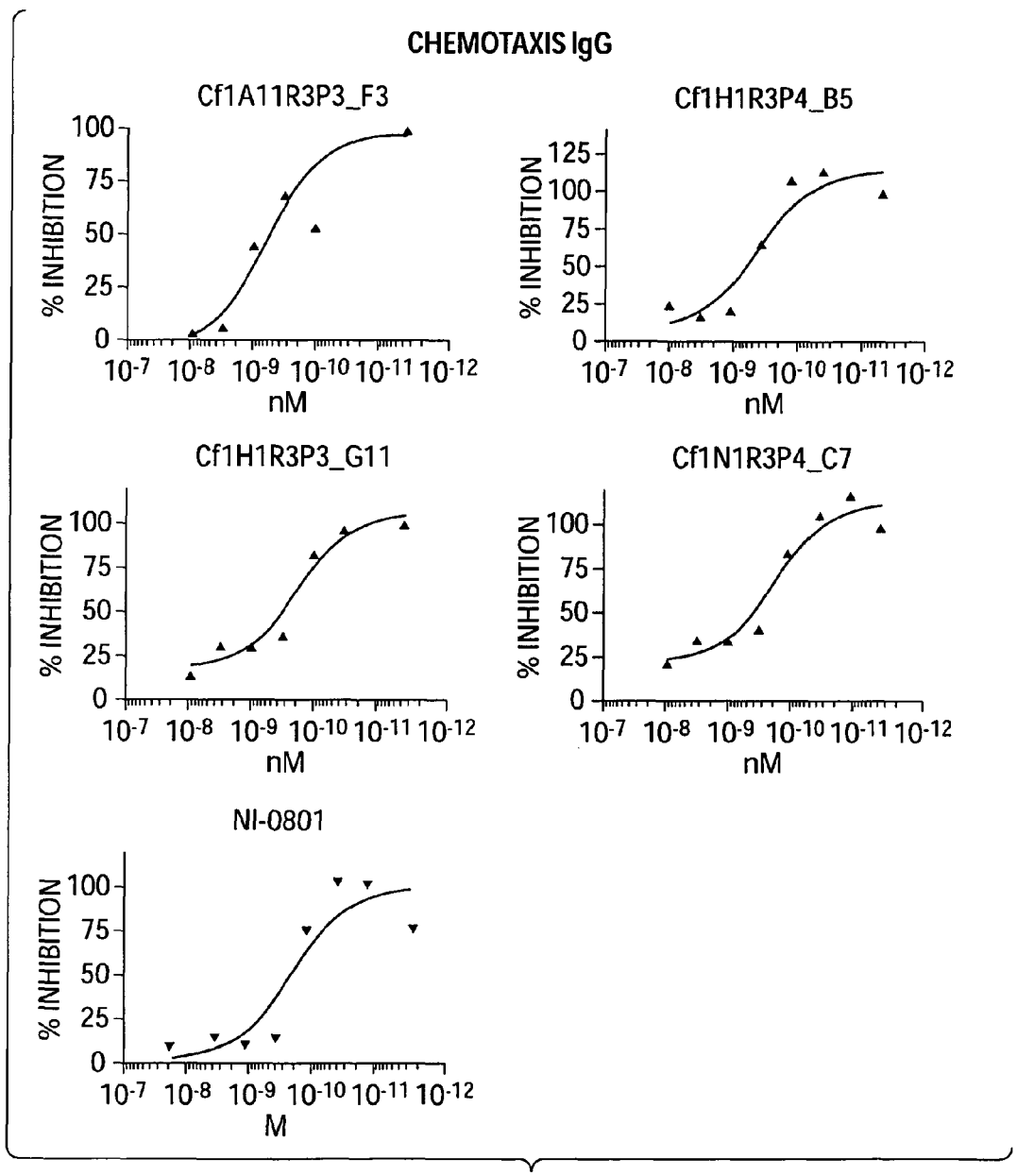
Figure 3A:
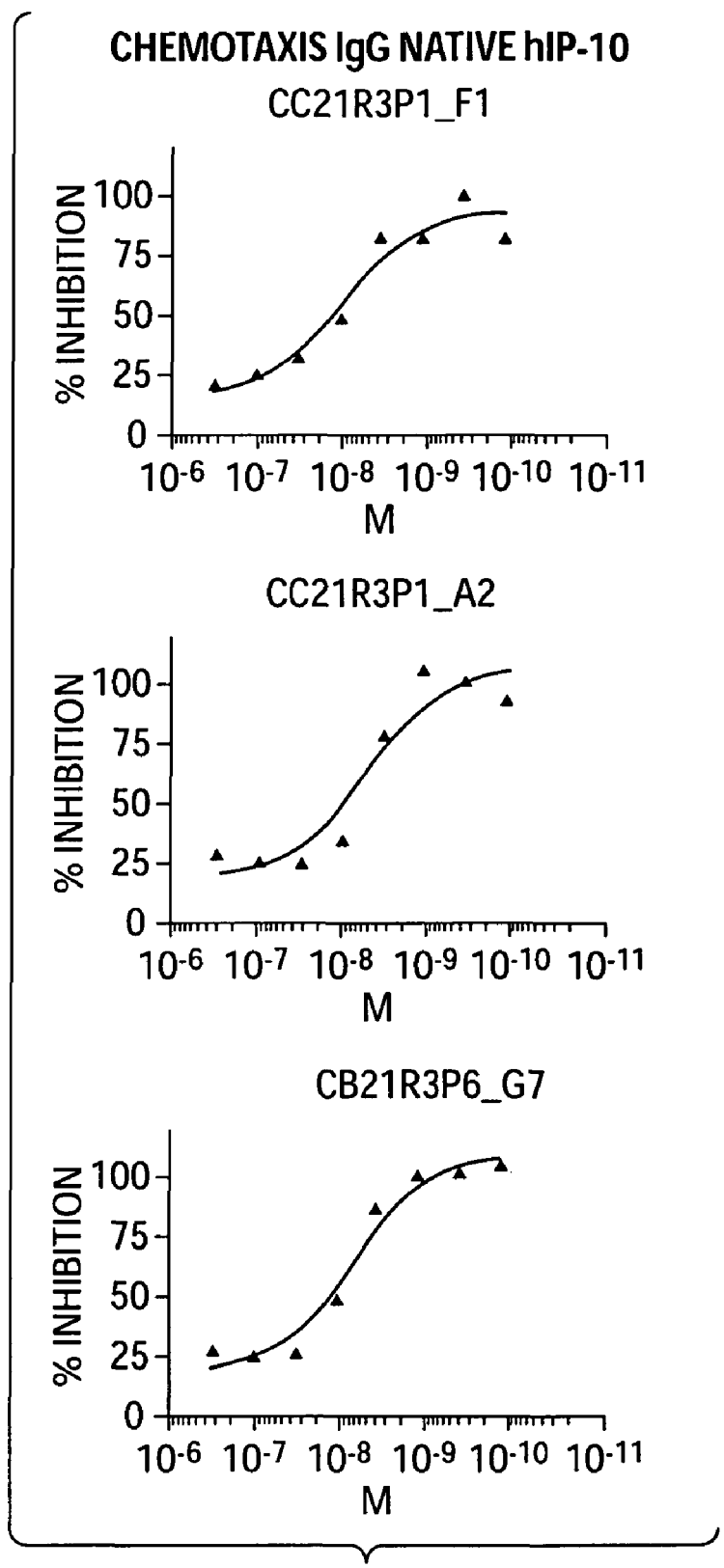
Figure 3B:
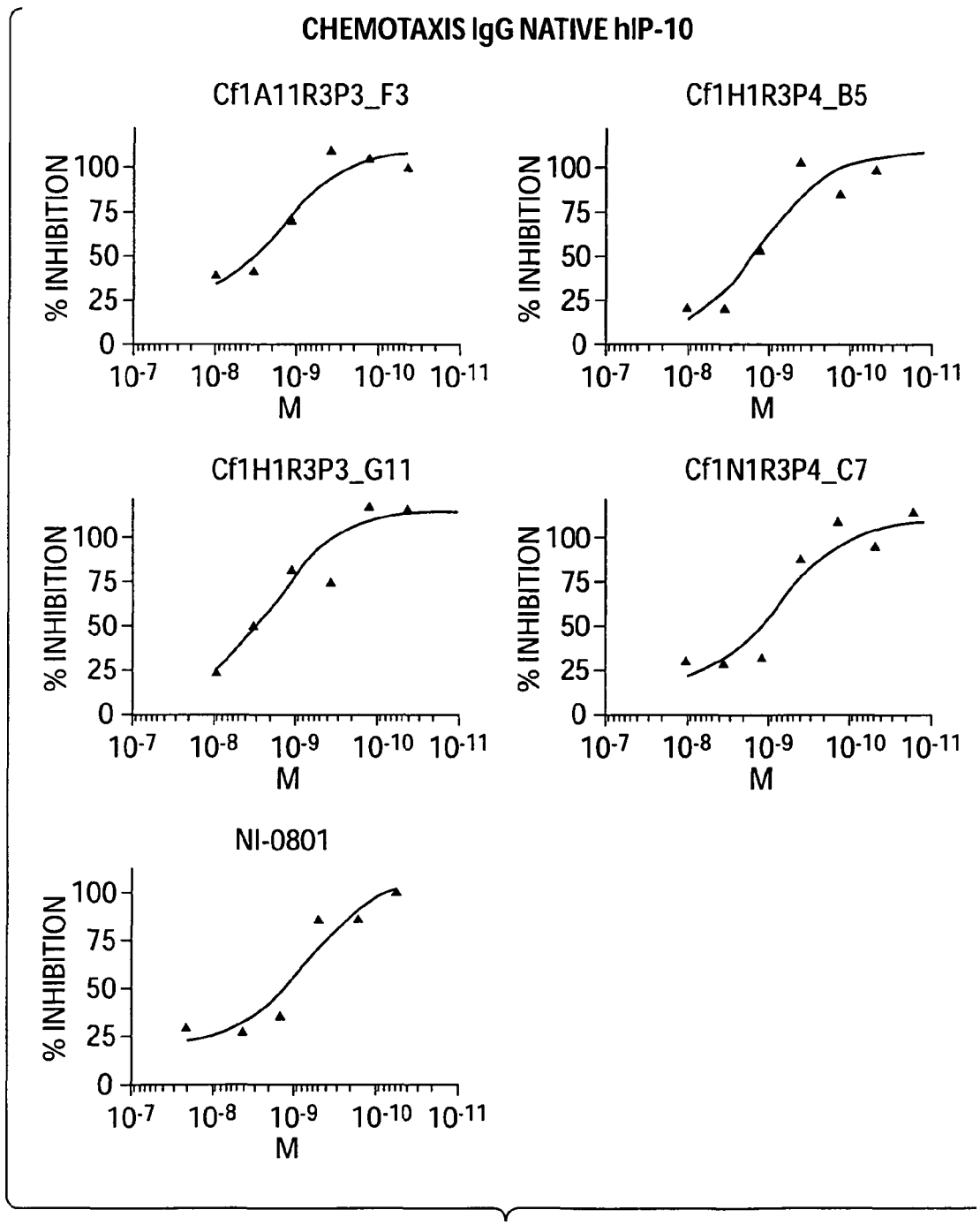

Inhibition of hIP-10-Induced Calcium Flux or Cell Chemotaxis Using Reformatted scFv into IgG1 Format scFv were reformatted into an IgG format as described above in Example 8. The neutralizing potential of the IgG on hIP-10-induced calcium flux or cell chemotaxis was evaluated using the cell-based assays described in Example 6 and 8. As shown in FIGS. 1, 2 and 3 these IgG clones inhibit the activity of both recombinant and native hIP-10 in a dose-dependent manner. The $IC_{50}$ values in these assays for each antibodies are summarized in Tables 5 and 6.

TABLE 5

Potency of antibodies tested in IgG1 format in chemotaxis and calcium flux functional assays. Chemotaxis was performed using either 1 nM, or 0.2 nM ($§$) of rhIP-10 while calcium flux was induced with 10 nM of rhIP-10. Antibodies in the top part of the table were obtained after affinity maturation.

| Clone ID | Chemotaxis $IC_{50}$ (nM) | Calcium flux $IC_{50}$ (nM) |
| --- | --- | --- |
| NI-0801 | 0.24$^§$ | 6.3 |
| Cf1N1R3P4_C7 | 0.19$^§$ | 4.1 |
| Cf1H1R3P3_G11 | 0.2$^§$ | 7.9 |
| Cf1H1R3P4_B5 | 0.42$^§$ | 4.7 |
| Cf1A11R3P3_F3 | 0.69$^§$ | 5.9 |
| CC21R3P1_F1 | 3 | 9.8 |
| CB21R3P3_E5 | 122 | ND |
| CC21R3P1_H6 | 75 | >200 |
| CB2R2P4_C3 | 33 | >200 |
| CC21R3P4_F4 | 157 | >200 |
| CC21R3P1_E7 | 56 | >200 |
| CC21R3P1_A2 | 3.2 | 9.8 |
| CB21R3P6_G7 | 8.8 | 6.2 |

TABLE 6

Potency of antibodies tested in IgG1 format in chemotaxis functional assay performed using native human IP-10 (hIP-10) at 0.6 nM.

| Clone ID | Chemotaxis $IC_{50}$ (nM) |
| --- | --- |
| NI-0801 | 0.58 |
| CF1N1R3P4_C7 | 0.64 |
| CF1H1R3P3_G11 | 1.9 |
| CF1H1R3P4_B5 | 1.2 |
| CF1A11R3P3_F3 | 1.7 |
| CC21R3P1_F1 | 11 |
| CC21R3P1_A2 | 6.2 |
| CB21R3P6_G7 | 7.8 |

Example 10

Antibody Binding to hIP-10 Immobilized on Glycosaminoglycan

Figure 4:
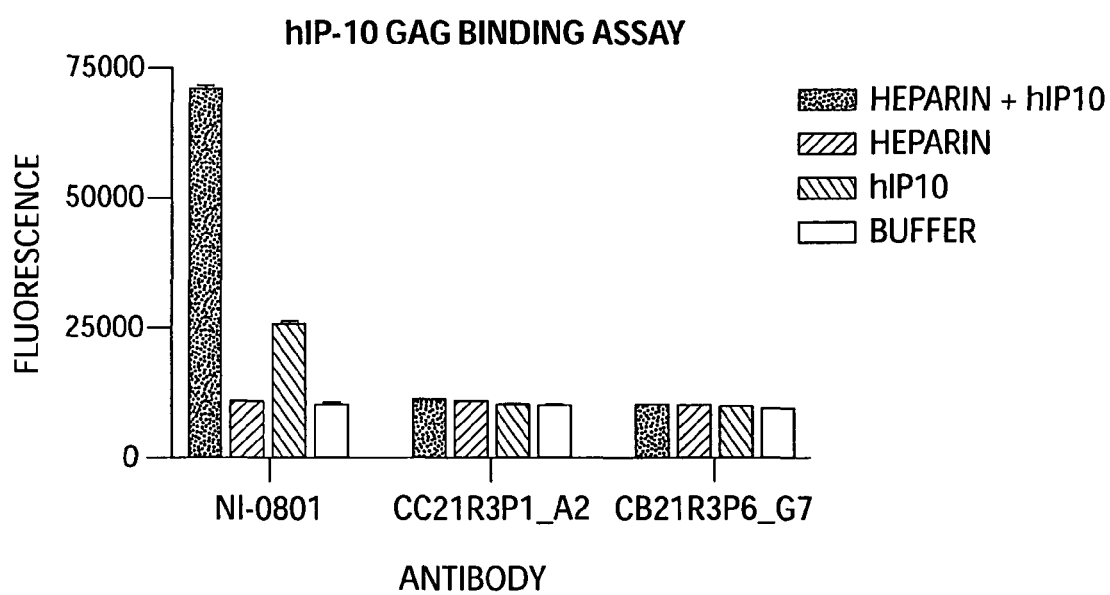
FIG. 4 is a graph depicting the capacity of huIP-10 antibodies to bind hIP-10 in the context of glycosaminoglycan (GAG).

As with many chemokines, hIP-10 is able to oligomerize and bind to glycosaminoglycans (GAG) expressed at surface of cells such as endothelial cells. In order to make sure that the antibodies were able to bind to hIP-10 in this context, they were tested in the following assay. Maxisorb 96 well plates were coated with anti-human Fc (Jackson, West Grove, Pa.) as capturing reagent for the human IgG to be tested. FITC-labeled heparin (Sigma, St. Louis, Mo.) was used as a prototypic GAG and was incubated with hIP-10 before addition to the captured anti-hIP10 antibodies. Binding was revealed using an HRP-coupled anti-FITC Fab (Roche, Basel, Switzerland). As shown in FIG. 4 some antibodies were able to bind hIP-10 when bound to GAG whereas others were unable to do so probably because their epitope on hIP-10 was no longer accessible within the oligomeric structure. The capacity of the antibodies to bind hIP-10 in the context of GAG is summarized in Table 7.

TABLE 7

Ability of antibodies to bind to hIP-10 immobilized on GAG.

| Clone ID | Binding to hIP-10 on GAG |
| --- | --- |
| NI-0801 | yes |
| CF1N1R3P4_C7 | yes |
| CF1H1R3P3_G11 | yes |
| CF1H1R3P4_B5 | yes |
| CF1A11R3P3_F3 | yes |
| CC21R3P1_F1 | yes |
| CB21R3P3_E5 | yes |
| CC21R3P1_H6 | yes |
| CC21R3P1_A2 | no |
| CB21R3P6_G7 | no |
| CC21R3P4_F4 | yes |

Example 11

Affinity Maturation of Antibody CC_F1

The selected lead candidate (CC21R3P1_F1) was subjected to affinity maturation in order to increase its affinity for hIP-10 and its potency in hIP-10 neutralization assays. Stretches of 5 residues in the CDR3 of the heavy or light chain were randomized in order to generate 6 libraries (Library size ranging from $5 \times 10^7$ to $2 \times 10^8$). Three high stringency selection rounds were performed as described in Example 5. Screening for improved variant was performed using scFv periplasmic extracts in an epitope competition assay. Briefly, the parent antibody (CC21R3P1_F1) was coated on plates and diluted periplasmic scFv extracts were added to each well. Biotinylated hIP-10 was then added and incubated for 2 hours at room temperature. After washing, hIP-10 remaining bound to the coated parent antibody was revealed using streptavidin coupled HRP (Jackson, West Grove Pa.). As a reference to identify improved variants, CC21R3P1_F1 scFv was used to compete coated CC21R3P1_F1 in an IgG format. The clone CF1A11R3P3_F3 was identified as a more potent antibody in competition assays well as chemotaxis and calcium flux assays.

A second round of affinity maturation was performed on clone CF1A11R3P3_F3 by combining its heavy chain with light chains that were selected during the CC21R3P1_F1 affinity maturation process. This second round lead to the identification of the clones CF1H1R3P4_B5 and CF1H1R3P3_G11. A third round of affinity maturation was performed on the heavy chain CDR3 of clone CF1H1R3P3_G11 and a further improved antibody variant, CF1N1R3P4_C7, was isolated. (Tables 4, 5 and 6)

In parallel a second candidate, CC21R3P1_E7, was also subjected to a similar affinity maturation process targeting the CDR3 of the light chain. In this process, the clone CE7C1R3H8_J9 was isolated and was more potent in chemotaxis assays when compared to the parent antibody.

Example 12

Back-Mutation of hIP-10 Antibody Clone C7 to Germline Sequence

In the studies described herein, the nucleotides and amino acid residues in the nucleic acid and amino acid sequence of the CF1N1R3P4_C7 clone were mutated to correspond to the nucleotide or amino acid residue found in the germline sequence. This process is referred to herein as "back-mutation".

Figure 5:
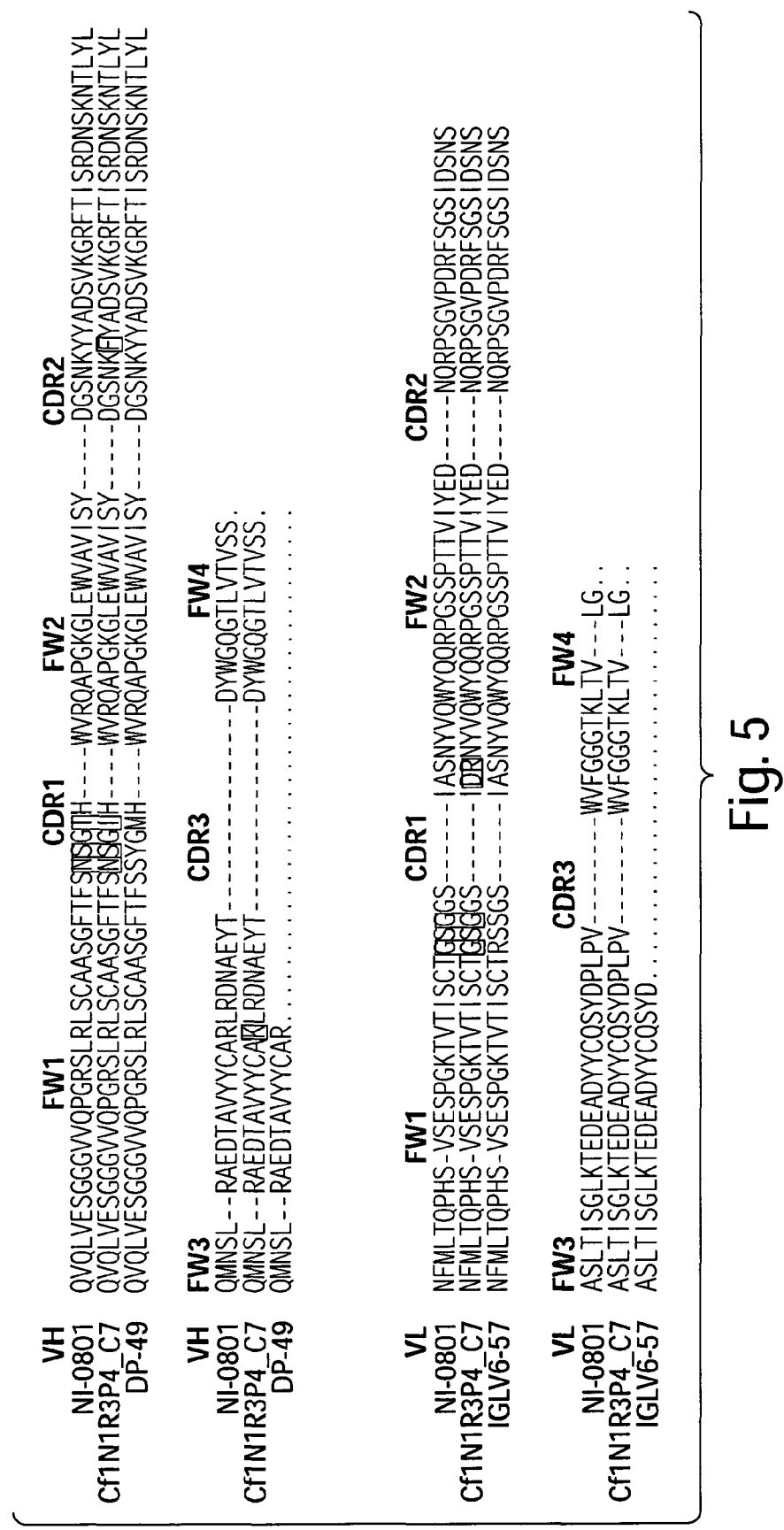
FIG. 5 is an illustration comparing the immunoglobulin heavy variable gene of antibody NI-0801 (SEQ ID NO: 2), antibody CF1N1R3P4_C7 (SEQ ID NO: 12) and the human germ line DP-49 or IGHV3-30 (SEQ ID NO: 20) and comparing the immunoglobulin light variable gene of antibody NI-0801 (SEQ ID NO: 4), antibody CF1N1R3P4_C7 (SEQ ID NO: 14) and the human germ line DP-49 or IGHV3-30 (SEQ ID NO: 146). The C7 VH has 5 mutations compared to IGHV3-30, three in the CDR1, one in CDR2 and one in the framework four. The C7 VL has 4 mutations compared to IGLV6-57, all located in the CDR1. The mutated amino acid residues are boxed in FIG. 5.

CF1N1R3P4_C7 heavy chain: The immunoglobulin heavy variable gene of antibody CF1N1R3P4_C7 had a 96% homology to the human germ line DP-49 or IGHV3-30 (GenBank Accession number M99663). CF1N1R3P4_C7 VH has 5 mutations compared to IGHV3-30, three in the CDR1, one in CDR2 and one in the framework four. The mutated amino acid residues are boxed in FIG. 5. The five mutations are: Ser to Asn at Kabat position 31; Tyr to Ser at Kabat position 32; Met to Ile at Kabat position 34; Tyr to Phe at Kabat position 58 and Arg to Lys at Kabat positions 94. All five amino acids of CF1N1R3P4_C7 VH were individually back mutated to their germline equivalent and the impact of the mutation on the antibody potency was evaluated in chemotaxis and calcium flux functional assays. A significant decrease in potency was observed for all changes in the CDR1 and therefore the amino acids found in CF1N1R3P4_C7 were left unchanged in the final NI-0801 sequence. The mutations in the CDR2 as well as at the end of the framework four did not alter the antibody potency and were therefore were introduced in the NI-0801 VH sequence. The immunoglobulin heavy joining (IGHJ) region of CF1N1R3P4_C7 was compared to the six human functional IGHJ regions. The IGHJ region of CF1N1R3P4_C7 was identified as IGHJ4 with a 100% homology outside the CDR3 encoding region.

CF1N1R3P4_C7 light chain: The immunoglobulin lambda variable gene (VL) of antibody CF1N1R3P4_C7 belongs to the IGLV6-57 or V1-22 subgroup (GenBank Accession Number Z73673). CF1N1R3P4_C7-VL has 4 mutations compared to IGLV6-57, all located in the CDR1. The mutated amino acid residues are shown in boxes in FIG. 5. The four mutations are: Arg to Gly at Kabat position 25; Ser to Gly at Kabat position 27; Ala to Asp and Ser to Arg at Kabat positions 29 and 30, respectively. The four mutations in the framework regions were changed pair wise (i.e. Gly25Arg/Gly27Ser and Asp29Ala/Arg30Ser). A significant decrease in potency was observed in Gly25Arg/Gly27Ser mutant and therefore the amino acids found in CF1N1R3P4_C7 at these positions were left unchanged. The mutations Asp29Ala/Arg30Ser did not alter the antibody potency and these two amino acids were mutated to their germline equivalents in the NI-0801 VL sequence.

The immunoglobulin heavy joining (IGLJ) region of CF1N1R3P4_C7 was compared to the seven human functional IGLJ regions. The IGLJ region of CF1N1R3P4_C7 was identified as IGL3J4 with a 100% homology outside the CDR3 encoding region.

Example 13

Affinity and Binding Kinetics of hIP-10 Antibodies

The affinity and binding kinetics of NI-0801 and CC21R3P1_F1 were characterized on a Biacore 2000 instrument (Biacore AB, Uppsala, Sweden). 200RU (response unit) of a goat anti-human polyclonal IgG (ahIgG; Biacore AB, Uppsala, Sweden) were immobilized by EDC/NHS chemistry on a C1 Biacore chip. This surface was used to capture NI-0801 or other human IgG1 that were characterized. The surface was regenerated after each cycle by injection of 10 mM glycine pH=1.5 at 30 µL/min, for 30 s followed by 1 min. of stabilization time in HBS-EP buffer.

Figure 6:
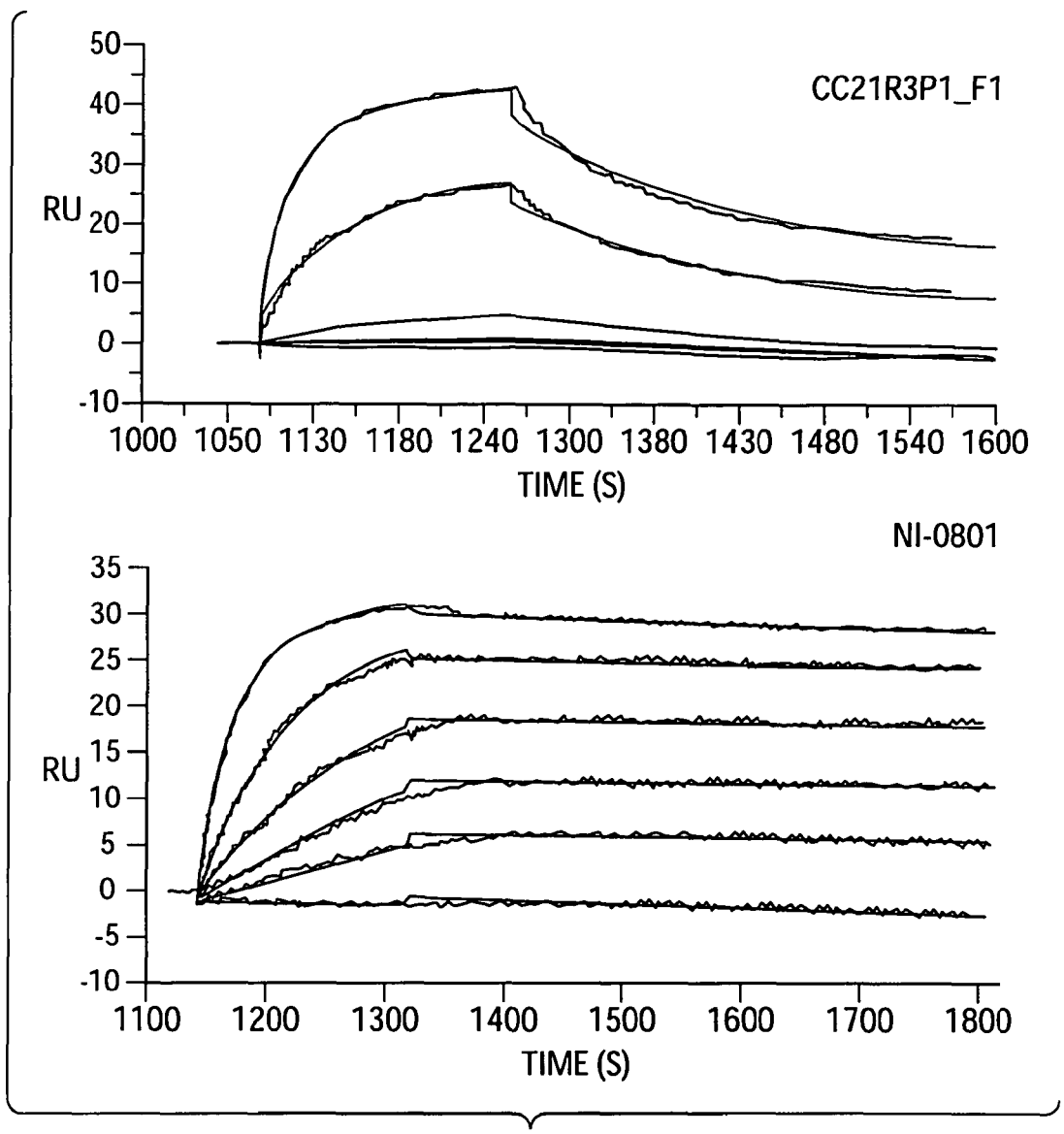
FIGS. 6A and 6B are graphs depicting the affinity of antibodies CC21R3P1_F1 and NI-0801 for hIP-10.

Binding was measured by passing either hIP-10 (Peprotech, Rocky Hill N.J.) or a NusA-hIP-10 fusion protein at the following concentrations: 34.7 nM, 11.6 nM, 3.85 nM, 1.28 nM, 0.428 nM, 0.142 nM and 0 nM. All solutions were diluted in HBS-EP buffer (Biacore AB, Uppsala, Sweden). Injection was performed at 50 µl/min for 3 min. followed by 12 min. of dissociation time and the temperature was set at 25° C. The data was fitted according to 1:1 Langmuir model and the $K_{on}$, $K_{off}$ and $K_D$ values determined. Very similar values were obtained using rhIP-10 or the NusA-hIP-10 fusion, but better response signals were obtained with the fusion protein due to its larger size that induces a better response on the Biacore. The affinity of antibodies and CC21R3P1_F1 and NI-0801 for hIP-10 are 90.2 nM and 109 pM, respectively (FIG. 6). It appears therefore that during the affinity maturation process the affinity of CC21R3P1_F1 was improved 90-fold. The Affinities and kinetic constants of both antibodies are summarized in Table 8.

TABLE 8

Kinetic and affinity constants measured by Biacore.

| Clone ID | Kon | Koff | KD (M) |
| --- | --- | --- | --- |
| CC21R3P1_F1 | $1.8 \times 10^5$ | $1.6 \times 10^{-3}$ | $9.2 \times 10^{-9}$ |
| NI-0801 | $6.8 \times 10^5$ | $7.4 \times 10^{-5}$ | $1.09 \times 10^{-10}$ |

Example 14

Cross-Reactivity of hIP-10 Antibody

Figure 7:
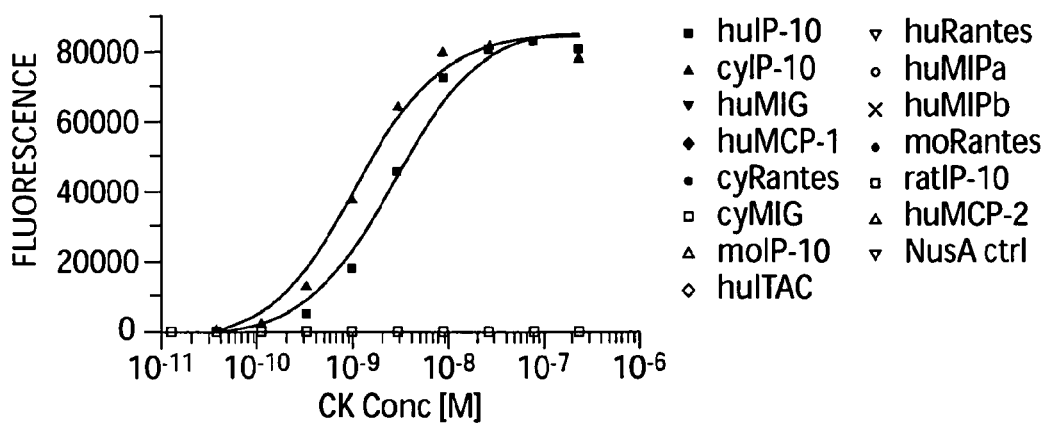
FIG. 7 is a graph depicting the cross-reactivity of the NI-0801 antibody with IP-10 from a variety of species and other human chemokines.

Binding assay: NI-0801 was tested for its ability to bind to IP-10 from different species using a capture ELISA format assay. Briefly, IP-10 cloned from cDNA isolated from mouse, rat, rabbit and cynomolgus as well as a panel of human chemokines was expressed and purified as described in Example 1. NI-0801 was coated and incubated with a concentration range of recombinant NusA fusion proteins. The level of binding was revealed using an anti-NusA antibody. As shown in FIG. 7, NI-0801 only cross reacts with cynomolgus IP-10 and not with IP-10 from other species nor with any of the other human chemokines tested.

Figure 8A:
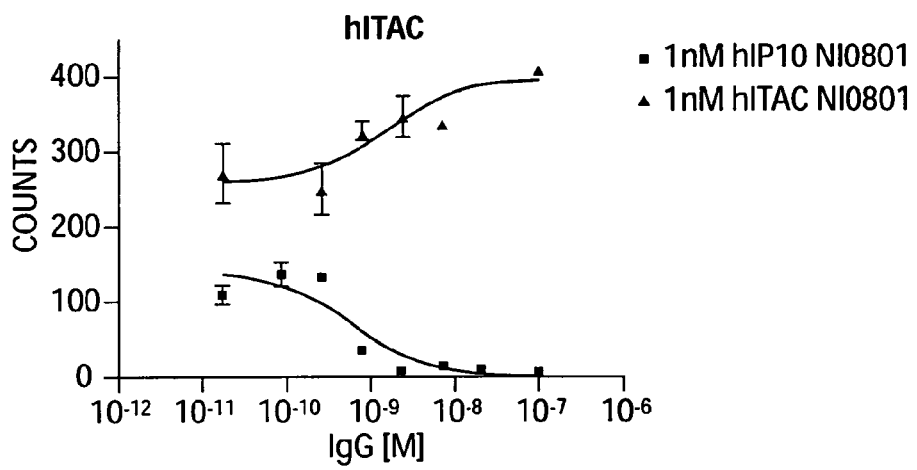
FIGS. 8A-8B are two graphs depicting the ability of recombinant hITAC, hMIG and hIP-10 to induce cells chemotaxis of hCXCR3 expressing L1.2 cells, and the ability of the NI-0801 antibody to neutralize the activity of these chemokines.
Figure 8B:
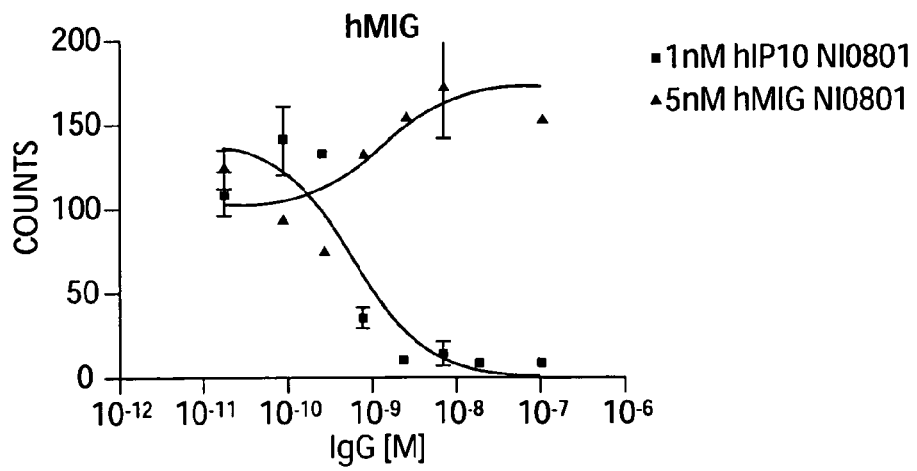
Figure 9:
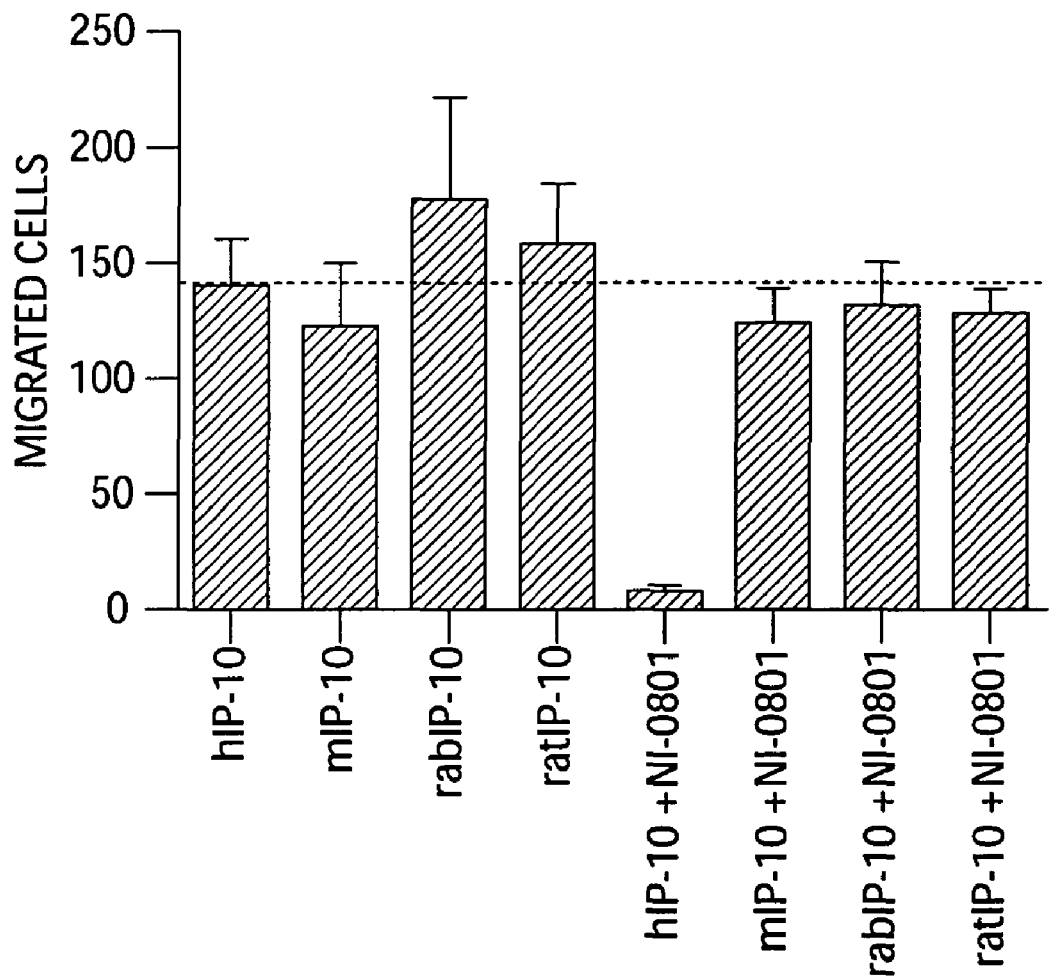
FIG. 9 is a graph depicting the neutralization potential of NI-0801 on IP-10 from a variety of different species.

Functional assays: Human ITAC and human MIG are chemokines that also signal via hCXCR3. NI-0801 was tested for its ability to neutralize these other hCXCR3 ligands in the chemotaxis assays described in Example 7. Recombinant hITAC, hMIG and hIP-10 (Peprotech) were all able to induce cells chemotaxis of hCXCR3 expressing L1.2 cells and NI-0801 was only able to neutralize the activity of hIP-10 (FIGS. 8A-8B). The neutralization potential of NI-0801 on IP-10 from different species was also assessed functionally. As shown in FIG. 9, recombinant human, mouse, rat and rabbit IP-10 are able to induce cell chemotaxis but only the activity of hIP-10 could be neutralized by a saturating dose of NI-0801 (50 µg/ml).

Example 15

Epitope Mapping of hIP-10 Antibody

Figure 10:
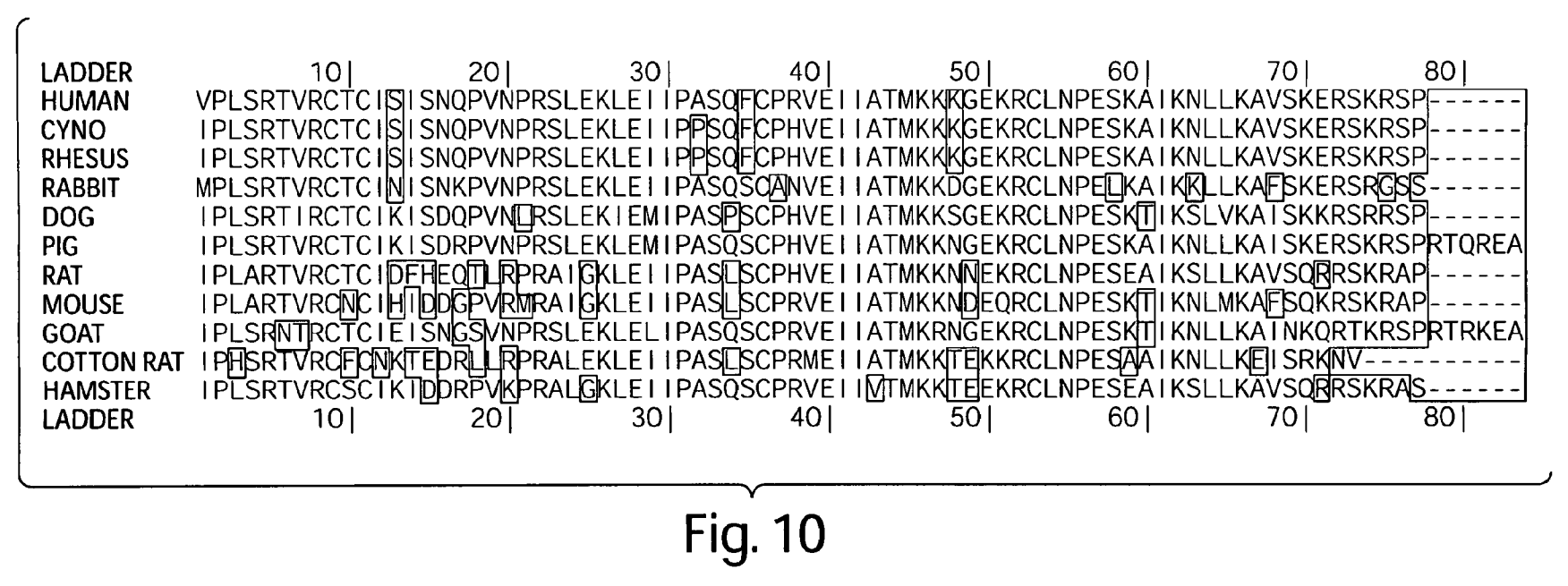
Figure 11:
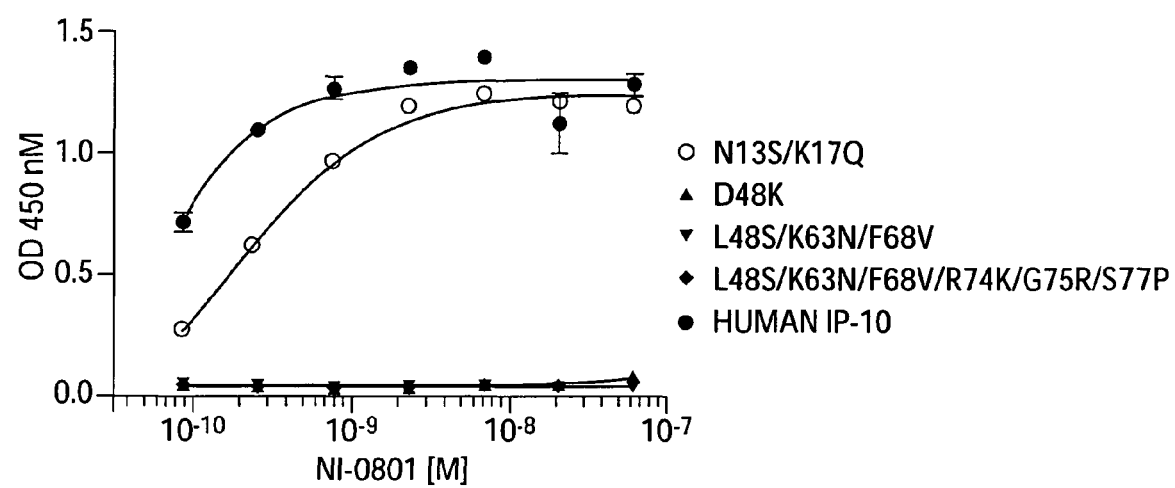
FIG. 11 is a graph depicting the ability of the NI-0801 antibody to bind mutated versions of rabbit IP-10.

In an ELISA assay, NI-0801 binds with equivalent apparent affinity to both human and cynomolgus IP-10 (FIG. 7). In order to identify residues potentially required on hIP-10 for binding to NI-0801, we aligned the IP-10 protein sequences from several species as shown in FIG. 10. In the alignment, we looked for residues that are conserved between the human and cynomolgus sequences and that are different in IP-10 from species to which NI-0801 is unable to bind. The sequence of rabbit IP-10 is close to the human IP-10 sequence although NI-0801 is unable to neutralize that protein. We identified several residues that are different in rabbit IP-10 when compared to both human and cynomolgus IP-10: N13, K17, D48, L48, K63, F68, R74, G75 and S77. Four mutants of rabbit IP-10 were generated by site directed mutagenesis in order to restore the human residues at those positions: [N13S/K17Q]; [D48K]; [L48S/K63N/F68V] and [L48S/K63N/F68V/R74K/G75R/S77P]. These mutant forms of rabbit IP-10 were expressed as NusA fusion proteins as described in Example 1. We then tested whether the introduction of these residues could restore NI-0801 binding to rabbit IP-10 in an ELISA assay. NusA-hIP-10 as well as the different NusA-rabbit IP-10 mutants were coated in a Maxisorb plate (Nunc) at 5 µg/ml over night at 4° C. After blocking with 3% PBS-BSA and incubation with a dose range of NI-0801 the plates were washed and incubated with a goat anti-human IgG Fcγ-specific antibody coupled to horse radish peroxidase (Jackson). After washing the signal was revealed with TMB (Roche) and stopped with $H_2SO_4$. The plates were read at 450 nm. As shown in FIG. 11, the [N13S/K17Q] mutant restores binding of NI-0801 to rabbit IP-10 indicating that S13 and Q17 are critical for the NI-0801 epitope integrity on human IP-10.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated fully human monoclonal anti-IP-10 antibody or fragment thereof, wherein said antibody comprises:
   (a) a $V_H$ CDR1 region comprising the amino acid sequence of SEQ ID NO: 5;
   (b) a $V_H$ CDR2 region comprising the amino acid sequence of SEQ ID NO: 15; and
   (c) a $V_H$ CDR3 region comprising the amino acid sequence of SEQ ID NO: 21;
   (d) a $V_L$ CDR1 region comprising the amino acid sequence of SEQ ID NO: 16;
   (e) a $V_L$ CDR2 region comprising the amino acid sequence of SEQ ID NO: 9; and
   (f) a $V_L$ CDR3 region comprising the amino acid sequence of SEQ ID NO: 29, wherein said antibody binds IP-10.

2. The antibody of claim 1, wherein said antibody is an IgG isotype.

3. The antibody of claim 1, wherein said antibody is an IgG1 isotype.

4. An isolated fully human monoclonal antibody, wherein said antibody comprises the heavy chain variable amino acid sequence of SEQ ID NO: 18, wherein said antibody further comprises the light chain variable amino acid sequence of SEQ ID NO: 28, and wherein said antibody binds IP-10.

5. The antibody of claim 4, wherein said antibody is an IgG isotype.

6. The antibody of claim 4, wherein said antibody is an IgG1 isotype.

7. A pharmaceutical composition comprising the antibody of claim 1 and a carrier.

* * * * *

SEQUENCE LISTING

```
<160> NUMBER OF SEQ ID NOS: 158

<210> SEQ ID NO 1
<211> LENGTH: 357
<212> TYPE: DNA
<213> ORGANISM: Artificial Sequence
<220> FEATURE:
<223> OTHER INFORMATION: chemically synthesized

<400> SEQUENCE: 1
caggtgcagc tggtggagtc tggggggaggc gtggtccagc ctgggaggtc cctgagactc      60
tcctgtgcag cctctggatt caccttcagt aactctggca tacactgggt ccgccaggct     120
ccaggcaagg gactggagtg ggtggcagtt atatcatatg atggaagtaa caaatactac     180
gcagactccg tgaagggccg attcaccatc tccagagaca actccaagaa cactctgtat     240
ctgcaaatga acagcctgag agctgaggac acggctgtct attattgtgc aagattgagg     300
gataatgcgg agtatactga ttactggggc cagggaaccc tggtcaccgt ctcgagt       357

<210> SEQ ID NO 2
<211> LENGTH: 119
<212> TYPE: PRT
<213> ORGANISM: Artificial Sequence
<220> FEATURE:
<223> OTHER INFORMATION: chemically synthesized

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ser
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Arg Asp Asn Ala Glu Tyr Thr Asp Tyr Trp Gly Gln Gly
                100                 105                 110

Thr Leu Val Thr Val Ser Ser
            115

<210> SEQ ID NO 3
<211> LENGTH: 334
<212> TYPE: DNA
<213> ORGANISM: Artificial Sequence
<220> FEATURE:
<223> OTHER INFORMATION: chemically synthesized

<400> SEQUENCE: 3
aattttatgc tgactcagcc ccactctgtg tcggagtctc cggggaagac ggtaaccatc      60
tcctgcaccg gcagcggtgg cagcattgcc agcaactatg tgcagtggta ccaacagcgc     120
ccgggcagtt cccccaccac tgtcatctat gaggataacc agagaccctc tggggtccct     180
gatcggttct ctggctccat cgacagctcc tccaattctg cctccctcac catctctggg     240
ctgaagactg aggacgaggc tgactactac tgtcagtctt atgatccgct tccggtgtgg     300
gttttcggcg gagggaccaa gctgaccgtc ctag                                 334

<210> SEQ ID NO 4
<211> LENGTH: 111
<212> TYPE: PRT
<213> ORGANISM: Artificial Sequence
<220> FEATURE:
<223> OTHER INFORMATION: chemically synthesized

<400> SEQUENCE: 4

Asn Phe Met Leu Thr Gln Pro His Ser Val Ser Glu Ser Pro Gly Lys
 1               5                  10                  15

Thr Val Thr Ile Ser Cys Thr Gly Ser Gly Gly Ser Ile Ala Ser Asn
                 20                  25                  30

Tyr Val Gln Trp Tyr Gln Gln Arg Pro Gly Ser Ser Pro Thr Thr Val
             35                  40                  45

Ile Tyr Glu Asp Asn Gln Arg Pro Ser Gly Val Pro Asp Arg Phe Ser
         50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Pro
                 85                  90                  95

Leu Pro Val Trp Val Phe Gly Gly Gly Thr Lys Leu Thr Val Leu
            100                 105                 110

<210> SEQ ID NO 5
<211> LENGTH: 5
<212> TYPE: PRT
<213> ORGANISM: Artificial Sequence
<220> FEATURE:
<223> OTHER INFORMATION: chemically synthesized

<400> SEQUENCE: 5

Asn Ser Gly Ile His
 1               5
```

```
<210> SEQ ID NO 6
<211> LENGTH: 17
<212> TYPE: PRT
<213> ORGANISM: Artificial Sequence
<220> FEATURE:
<223> OTHER INFORMATION: chemically synthesized

<400> SEQUENCE: 6

Val Ile Ser Tyr Asp Gly Ser Asn Lys Tyr Tyr Ala Asp Ser Val Lys
1               5                   10                  15

Gly

<210> SEQ ID NO 7
<211> LENGTH: 10
<212> TYPE: PRT
<213> ORGANISM: Artificial Sequence
<220> FEATURE:
<223> OTHER INFORMATION: chemically synthesized

<400> SEQUENCE: 7

Leu Arg Asp Asn Ala Glu Tyr Thr Asp Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: chemically synthesized

<400> SEQUENCE: 8

Thr Gly Ser Gly Gly Ser Ile Ala Ser Asn Tyr Val Gln
1               5                   10

<210> SEQ ID NO 9
<211> LENGTH: 7
<212> TYPE: PRT
<213> ORGANISM: Artificial Sequence
<220> FEATURE:
<223> OTHER INFORMATION: chemically synthesized

<400> SEQUENCE: 9

Glu Asp Asn Gln Arg Pro Ser
1               5

<210> SEQ ID NO 10
<211> LENGTH: 10
<212> TYPE: PRT
<213> ORGANISM: Artificial Sequence
<220> FEATURE:
<223> OTHER INFORMATION: chemically synthesized

<400> SEQUENCE: 10

Gln Ser Tyr Asp Pro Leu Pro Val Trp Val
1               5                   10

<210> SEQ ID NO 11
<211> LENGTH: 358
<212> TYPE: DNA
<213> ORGANISM: Artificial Sequence
<220> FEATURE:
<223> OTHER INFORMATION: chemically synthesized

<400> SEQUENCE: 11
caggtgcagc tggtggagtc tgggggaggc gtggtccagc ctggggaggtc cctgagactc      60 tcctgtgcag cctctggatt caccttcagt aactctggca tacactgggt ccgccaggct     120
```

```
ccaggcaagg gactggagtg ggtggcagtt atatcatatg atggaagtaa caaattctac    180
gcagactccg tgaagggccg attcaccatc tccagagaca actccaagaa cactctgtat    240
ctgcaaatga acagcctgag agctgaggac acggctgtct attattgtgc aaaattgagg    300
gataatgcgg agtatactga ttactggggc cagggaaccc tggtcaccgt ctcgagtg     358
```

<210> SEQ ID NO 12
<211> LENGTH: 119
<212> TYPE: PRT
<213> ORGANISM: Artificial Sequence
<220> FEATURE:
<223> OTHER INFORMATION: chemically synthesized

<400> SEQUENCE: 12

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ser
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Arg Asp Asn Ala Glu Tyr Thr Asp Tyr Trp Gly Gln Gly
            100                 105                 110

Thr Leu Val Thr Val Ser Ser
        115
```

<210> SEQ ID NO 13
<211> LENGTH: 333
<212> TYPE: DNA
<213> ORGANISM: Artificial Sequence
<220> FEATURE:
<223> OTHER INFORMATION: chemically synthesized

<400> SEQUENCE: 13

```
aattttatgc tgactcagcc ccactctgtg tcggagtctc cggggaagac ggtgaccatc    60
tcctgcaccg gcagcggtgg cagcattgac agaaactatg tgcagtggta ccagcagcgc    120
ccgggcagtt cccccaccac tgtgatctat gaggataacc aaagaccctc tggggtcccg    180
gatcgattct ctggctccat cgacagctcc tccaactctg cctccctcac catctctgga    240
ctaaaaactg aagacgaggc tgactactac tgtcagtctt atgatccgct tccggtgtgg    300
gttttcggcg gagggaccaa gctcaccgtc cta                                  333
```

<210> SEQ ID NO 14
<211> LENGTH: 111
<212> TYPE: PRT
<213> ORGANISM: Artificial Sequence
<220> FEATURE:
<223> OTHER INFORMATION: chemically synthesized

<400> SEQUENCE: 14

```
Asn Phe Met Leu Thr Gln Pro His Ser Val Ser Glu Ser Pro Gly Lys
1               5                   10                  15

Thr Val Thr Ile Ser Cys Thr Gly Ser Gly Gly Ser Ile Asp Arg Asn
            20                  25                  30
```

-continued

```
Tyr Val Gln Trp Tyr Gln Gln Arg Pro Gly Ser Ser Pro Thr Thr Val
         35                  40                  45
Ile Tyr Glu Asp Asn Gln Arg Pro Ser Gly Val Pro Asp Arg Phe Ser
     50                  55                  60
Gly Ser Ile Asp Ser Ser Asn Ser Ala Ser Leu Thr Ile Ser Gly
 65                  70                  75                  80
Leu Lys Thr Glu Asp Glu Ala Asp Tyr Tyr Cys Gln Ser Tyr Asp Pro
                 85                  90                  95
Leu Pro Val Trp Val Phe Gly Gly Gly Thr Lys Leu Thr Val Leu
            100                 105                 110

<210> SEQ ID NO 15
<211> LENGTH: 17
<212> TYPE: PRT
<213> ORGANISM: Artificial Sequence
<220> FEATURE:
<223> OTHER INFORMATION: chemically synthesized

<400> SEQUENCE: 15

Val Ile Ser Tyr Asp Gly Ser Asn Lys Phe Tyr Ala Asp Ser Val Lys
 1               5                  10                  15
Gly

<210> SEQ ID NO 16
<211> LENGTH: 13
<212> TYPE: PRT
<213> ORGANISM: Artificial Sequence
<220> FEATURE:
<223> OTHER INFORMATION: chemically synthesized

<400> SEQUENCE: 16

Thr Gly Ser Gly Gly Ser Ile Asp Arg Asn Tyr Val Gln
 1               5                  10

<210> SEQ ID NO 17
<211> LENGTH: 357
<212> TYPE: DNA
<213> ORGANISM: Artificial Sequence
<220> FEATURE:
<223> OTHER INFORMATION: chemically synthesized

<400> SEQUENCE: 17
caggtgcagc tggtggagtc tgggggaggc gtggtccagc ctgggaggtc cctgagactc    60
tcctgtgcag cctctggatt caccttcagt aactctggca tacactgggt ccgccaggct   120
ccaggcaagg gactggagtg gtggcagtt atatcatatg atggaagtaa caaattctac   180
gcagactccg tgaagggccg attcaccatc tccagacaa actccaagaa cactctgtat   240
ctgcaaatga acagcctgag agctgaggac acggctgtct attattgtgc aaaattgagg   300
gataatggtg agtacttaga ctactggggc cagggaaccc tggtcaccgt ctcgagt     357

<210> SEQ ID NO 18
<211> LENGTH: 119
<212> TYPE: PRT
<213> ORGANISM: Artificial Sequence
<220> FEATURE:
<223> OTHER INFORMATION: chemically synthesized

<400> SEQUENCE: 18

Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Asn Ser
```

```
            20                  25                  30
Gly Ile His Trp Val Arg Gln Ala Pro Gly Lys Gly Leu Glu Trp Val
        35                  40                  45

Ala Val Ile Ser Tyr Asp Gly Ser Asn Lys Phe Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Arg Asp Asn Gly Glu Tyr Leu Asp Tyr Trp Gly Gln Gly
            100                 105                 110

Thr Leu Val Thr Val Ser Ser
        115
```

<210> SEQ ID NO 19
<211> LENGTH: 333
<212> TYPE: DNA
<213> ORGANISM: Artificial Sequence
<220> FEATURE:
<223> OTHER INFORMATION: chemically synthesized

<400> SEQUENCE: 19

```
aattttatgc tgactcagcc ccactctgtg tcggagtctc cggggaagac ggtgaccatc    60
tcctgcaccg gcagcggtgg cagcattgac agaaactatg tgcagtggta ccagcagcgc   120
ccgggcagtt cccccaccac tgtgatctat gaggataacc aaagaccctc tggggtcccg   180
gatcgattct ctggctccat cgacagctcc tccaactctg cctccctcac catctctgga   240
ctaaaaactg aagacgaggc tgactactac tgtcagtctt atgatccgct tccggtgtgg   300
gttttcggcg gagggaccaa gctcaccgtc cta                                333
```

<210> SEQ ID NO 20
<211> LENGTH: 98
<212> TYPE: PRT
<213> ORGANISM: Homo sapiens

<400> SEQUENCE: 20

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 21
<211> LENGTH: 10
<212> TYPE: PRT
<213> ORGANISM: Artificial Sequence
<220> FEATURE:
<223> OTHER INFORMATION: chemically synthesized

<400> SEQUENCE: 21

<210> SEQ ID NO 22
<211> LENGTH: 334
<212> TYPE: DNA
<213> ORGANISM: Artificial Sequence
<220> FEATURE:
<223> OTHER INFORMATION: chemically synthesized

<400> SEQUENCE: 22

```
aattttatgc tgactcagcc ccactctgtg tcggagtctc cggggaagac ggtgaccatc      60
tcctgcaccg gcagcggtgg cagcattgac agaaactatg tgcagtggta ccagcagcgc     120
ccgggcagtt cccccaccac tgtgatctat gaggataacc aaagaccctc tggggtcccg     180
gatcgattct ctggctccat cgacagctcc tccaactctg cctccctcac catctctgga     240
ctaaaaactg aagacgaggc tgactactac tgtcagtctt atgtggagac gcctgagtgg     300
gttttcggcg agggaccaa gctcaccgtc ctag                                   334
```

<210> SEQ ID NO 23
<211> LENGTH: 111
<212> TYPE: PRT
<213> ORGANISM: Artificial Sequence
<220> FEATURE:
<223> OTHER INFORMATION: chemically synthesized

<400> SEQUENCE: 23

```
Asn Phe Met Leu Thr Gln Pro His Ser Val Ser Glu Ser Pro Gly Lys
1               5                   10                  15

Thr Val Thr Ile Ser Cys Thr Gly Ser Gly Gly Ser Ile Asp Arg Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Val Glu
                85                  90                  95

Thr Pro Glu Trp Val Phe Gly Gly Gly Thr Lys Leu Thr Val Leu
            100                 105                 110
```

<210> SEQ ID NO 24
<211> LENGTH: 10
<212> TYPE: PRT
<213> ORGANISM: Artificial Sequence
<220> FEATURE:
<223> OTHER INFORMATION: chemically synthesized

<400> SEQUENCE: 24

```
Gln Ser Tyr Val Glu Thr Pro Glu Trp Val
1               5                   10
```

<210> SEQ ID NO 25
<211> LENGTH: 357
<212> TYPE: DNA
<213> ORGANISM: Artificial Sequence
<220> FEATURE:
<223> OTHER INFORMATION: chemically synthesized

<400> SEQUENCE: 25

```
caggtgcagc tggtggagtc tgggggaggc gtggtccagc ctggagggtc ccacacactc      60
```

```
tcctgtgcag cctctggatt cgccttcaaa aactctggca tacactgggt ccgccaggct    120
ccaggcaagg gactggagtg ggtggcagtt atatcatatg atggaagtaa caaattctac    180
gcagactccg tgaagggccg attcaccatc tccagagaca actcccagaa cactgtatat    240
ctgcaaatga ctgacctgag acctgacgac acggctgtct attattgtgc aagagatggg    300
agtgagagcg agtacttaga ctactggggc aagggaaccc tggtcaccgt ctcgagt       357
```

<210> SEQ ID NO 26
<211> LENGTH: 119
<212> TYPE: PRT
<213> ORGANISM: Artificial Sequence
<220> FEATURE:
<223> OTHER INFORMATION: chemically synthesized

<400> SEQUENCE: 26

```
Gln Val Gln Leu Val Glu Ser Gly Gly Gly Val Val Gln Pro Gly Arg
1               5                   10                  15

Ser His Thr Leu Ser Cys Ala Ala Ser Gly Phe Ala Phe Lys Asn Ser
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asn Lys Phe Tyr Ala Asp Ser Val
    50                  55                  60

Lys Gly Arg Phe Thr Ile Ser Arg Asp Asn Ser Gln Asn Thr Val Tyr
65                  70                  75                  80

Leu Gln Met Thr Asp Leu Arg Pro Asp Asp Thr Ala Val Tyr Tyr Cys
                85                  90                  95

Ala Arg Asp Gly Ser Glu Ser Glu Tyr Leu Asp Tyr Trp Gly Lys Gly
            100                 105                 110

Thr Leu Val Thr Val Ser Ser
        115
```

<210> SEQ ID NO 27
<211> LENGTH: 335
<212> TYPE: DNA
<213> ORGANISM: Artificial Sequence
<220> FEATURE:
<223> OTHER INFORMATION: chemically synthesized

<400> SEQUENCE: 27

```
aattttatgc tgactcagcc ccactctgtg tcggagtctc cggggaagac ggtgaccatc     60
tcctgcaccg gcagcggtgg cagcattgac agaaactatg tgcagtggta ccagcagcgc    120
ccgggcagtg cccccatcac tgtgatctat gaggataacc aaagaccctc tggggtcccg    180
gatcgattct ctggctccat cgacagctcc tccaactctg cctccctcac catctctgga    240
ctacggactg acgacgaggc tgactactac tgtcagtctt atgatagcat caatctttgg    300
gttttcggcg gagggaccaa ggtcaccgtc ctagg                               335
```

<210> SEQ ID NO 28
<211> LENGTH: 111
<212> TYPE: PRT
<213> ORGANISM: Artificial Sequence
<220> FEATURE:
<223> OTHER INFORMATION: chemically synthesized

<400> SEQUENCE: 28

```
Asn Phe Met Leu Thr Gln Pro His Ser Val Ser Glu Ser Pro Gly Lys
1               5                   10                  15
```

```
Thr Val Thr Ile Ser Cys Thr Gly Ser Gly Gly Ser Ile Asp Arg Asn
         20                  25                  30

Tyr Val Gln Trp Tyr Gln Gln Arg Pro Gly Ser Ala Pro Ile Thr Val
     35                  40                  45

Ile Tyr Glu Asp Asn Gln Arg Pro Ser Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Arg Thr Asp Asp Glu Ala Asp Tyr Tyr Cys Gln Ser Tyr Asp Ser
                 85                  90                  95

Ile Asn Leu Trp Val Phe Gly Gly Gly Thr Lys Val Thr Val Leu
            100                 105                 110
```

<210> SEQ ID NO 29
<211> LENGTH: 10
<212> TYPE: PRT
<213> ORGANISM: Artificial Sequence
<220> FEATURE:
<223> OTHER INFORMATION: chemically synthesized

<400> SEQUENCE: 29

```
Gln Ser Tyr Asp Ser Ile Asn Leu Trp Val
1               5                   10
```

<210> SEQ ID NO 30
<211> LENGTH: 360
<212> TYPE: DNA
<213> ORGANISM: Artificial Sequence
<220> FEATURE:
<223> OTHER INFORMATION: chemically synthesized

<400> SEQUENCE: 30

```
caggtgcagc tggtgcagtt tggggggaggc gtggtccagc ctggggaggtc cttgagactc      60 tcctgtgcag cctctggatt caccttcagt agctatggca tgcactgggt ccgccaggct     120
ccaggcaagg ggctggagtg ggtggcagtt atatcatatg atggaagtat taaatactat     180
gcagactccg tgaagggccg attcaccatc tccagagaaa atgccaagaa ctccgtgtat     240
ctgcaaatgg acagcctgag agtcggggac acggctgtgt attactgtac aagagccggg     300
tatagtactg actggcatcc cgactactgg ggccagggga caatggtcac cgtctcgagt     360
```

<210> SEQ ID NO 31
<211> LENGTH: 120
<212> TYPE: PRT
<213> ORGANISM: Artificial Sequence
<220> FEATURE:
<223> OTHER INFORMATION: chemically synthesized

<400> SEQUENCE: 31

```
Gln Val Gln Leu Val Gln Phe Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
         35                  40                  45

Ala Val Ile Ser Tyr Asp Gly Ser Ile Lys Tyr Tyr Ala Asp Ser Val
 50                  55                  60

Lys Gly Arg Phe Thr Ile Ser Arg Glu Asn Ala Lys Asn Ser Val Tyr
 65                  70                  75                  80

Leu Gln Met Asp Ser Leu Arg Val Gly Asp Thr Ala Val Tyr Tyr Cys
                 85                  90                  95
```

```
Thr Arg Ala Gly Tyr Ser Thr Asp Trp His Pro Asp Tyr Trp Gly Gln
            100                 105                 110

Gly Thr Met Val Thr Val Ser Ser
            115                 120

<210> SEQ ID NO 32
<211> LENGTH: 324
<212> TYPE: DNA
<213> ORGANISM: Artificial Sequence
<220> FEATURE:
<223> OTHER INFORMATION: chemically synthesized

<400> SEQUENCE: 32
tcttctgagc tgactcagga ccctgctgtg tctgtggcct tgggacagac agtcaggatc      60
acatgccaag agacagcct cagaagctat tatgcaagct ggtaccagca gaagccagga     120 caggccctg tacttgccat ctatggtaaa acaaccggc cctcagggat cccagaccga     180
ttctctggct ccagctcagg aaacacagct tccttgacca tcactggggc tcaggcggaa     240
gatgaggctg actattactg taactcccgg gacagcagtg gtaaccatgt ggtattcggc     300
ggagggacca agctgaccgt ccta                                            324

<210> SEQ ID NO 33
<211> LENGTH: 108
<212> TYPE: PRT
<213> ORGANISM: Artificial Sequence
<220> FEATURE:
<223> OTHER INFORMATION: chemically synthesized

<400> SEQUENCE: 33

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Ala Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 34
<211> LENGTH: 5
<212> TYPE: PRT
<213> ORGANISM: Artificial Sequence
<220> FEATURE:
<223> OTHER INFORMATION: chemically synthesized

<400> SEQUENCE: 34

Ser Tyr Gly Met His
1               5

<210> SEQ ID NO 35
<211> LENGTH: 17
<212> TYPE: PRT
<213> ORGANISM: Artificial Sequence
<220> FEATURE:
<223> OTHER INFORMATION: chemically synthesized
```

<400> SEQUENCE: 35

Val Ile Ser Tyr Asp Gly Ser Ile Lys Tyr Tyr Ala Asp Ser Val Lys
1               5                   10                  15
Gly

<210> SEQ ID NO 36
<211> LENGTH: 11
<212> TYPE: PRT
<213> ORGANISM: Artificial Sequence
<220> FEATURE:
<223> OTHER INFORMATION: chemically synthesized

<400> SEQUENCE: 36

Ala Gly Tyr Ser Thr Asp Trp His Pro Asp Tyr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: chemically synthesized

<400> SEQUENCE: 37

Gln Gly Asp Ser Leu Arg Ser Tyr Tyr Ala Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: chemically synthesized

<400> SEQUENCE: 38

Gly Lys Asn Asn Arg Pro Ser
1               5

<210> SEQ ID NO 39
<211> LENGTH: 11
<212> TYPE: PRT
<213> ORGANISM: Artificial Sequence
<220> FEATURE:
<223> OTHER INFORMATION: chemically synthesized

<400> SEQUENCE: 39

Asn Ser Arg Asp Ser Ser Gly Asn His Val Val
1               5                   10

<210> SEQ ID NO 40
<211> LENGTH: 366
<212> TYPE: DNA
<213> ORGANISM: Artificial Sequence
<220> FEATURE:
<223> OTHER INFORMATION: chemically synthesized

<400> SEQUENCE: 40
caggtcacct tgagggagtc tggtcctgcg ctggtgaaac ccacacagac cctcacactg     60
acctgcacct tctctggatt ctcactcacc actagtggaa tgtctgtgat ttggatccgt    120
cagcccccag ggaaggccct ggagtggctt gcacgcattg attcggatga cgagaaacac    180
tacaacacat ctctgaagac caggctcgcc atctccaagg acacctccaa aaaccaggtg    240
gtccttacaa tgaccaacat ggaccctgtg gacacaggca cctattactg tgcacggctt    300

```
cgggctggtt caggtccata tgttttgac tcctgggggc aagggaccac ggtcaccgtc    360
tcgagt                                                              366
```

<210> SEQ ID NO 41
<211> LENGTH: 122
<212> TYPE: PRT
<213> ORGANISM: Artificial Sequence
<220> FEATURE:
<223> OTHER INFORMATION: chemically synthesized

<400> SEQUENCE: 41

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Thr Thr Ser
            20                  25                  30

Gly Met Ser Val Ile Trp Ile Arg Gln Pro Pro Gly Lys Ala Leu Glu
        35                  40                  45

Trp Leu Ala Arg Ile Asp Ser Asp Asp Glu Lys His Tyr Asn Thr Ser
    50                  55                  60

Leu Lys Thr Arg Leu Ala Ile Ser Lys Asp Thr Ser Lys Asn Gln Val
65                  70                  75                  80

Val Leu Thr Met Thr Asn Met Asp Pro Val Asp Thr Gly Thr Tyr Tyr
                85                  90                  95

Cys Ala Arg Leu Arg Ala Gly Ser Gly Pro Tyr Val Phe Asp Ser Trp
            100                 105                 110

Gly Gln Gly Thr Thr Val Thr Val Ser Ser
        115                 120
```

<210> SEQ ID NO 42
<211> LENGTH: 331
<212> TYPE: DNA
<213> ORGANISM: Artificial Sequence
<220> FEATURE:
<223> OTHER INFORMATION: chemically synthesized

<400> SEQUENCE: 42

```
cagtctgtgc tgactcagcc acccctcagcg tctgggaccc ccgggcagag ggtcaccatc    60
tcttgttctg gaagcagctc caacatcggg agtaacactg taaactggta ccagcgactc   120
ccaggagcgg ccccccaact cctcatctac aataatgacc agcggccctc agggatccct   180
gaccgattct ctggctccaa gtctggcacc tcaggctccc tggtcatcag tgggctccag   240
tctgaagacg aggctgatta ctactgtgcg tcatgggatg acagtctgaa tggtcgggtg   300
ttcggcggag ggaccaagct gaccgtccta g                                   331
```

<210> SEQ ID NO 43
<211> LENGTH: 110
<212> TYPE: PRT
<213> ORGANISM: Artificial Sequence
<220> FEATURE:
<223> OTHER INFORMATION: chemically synthesized

<400> SEQUENCE: 43

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Arg Leu Pro Gly Ala Ala Pro Gln Leu Leu
        35                  40                  45

Ile Tyr Asn Asn Asp Gln Arg Pro Ser Gly Ile Pro Asp Arg Phe Ser
```

```
                50                  55                  60
Gly Ser Lys Ser Gly Thr Ser Gly Ser Leu Val Ile Ser Gly Leu Gln
 65                  70                  75                  80

Ser Glu Asp Glu Ala Asp Tyr Tyr Cys Ala Ser Trp Asp Asp Ser Leu
                 85                  90                  95

Asn Gly Arg Val Phe Gly Gly Gly Thr Lys Leu Thr Val Leu
                100                 105                 110

<210> SEQ ID NO 44
<211> LENGTH: 7
<212> TYPE: PRT
<213> ORGANISM: Artificial Sequence
<220> FEATURE:
<223> OTHER INFORMATION: chemically synthesized

<400> SEQUENCE: 44

Thr Ser Gly Met Ser Val Ile
1               5

<210> SEQ ID NO 45
<211> LENGTH: 16
<212> TYPE: PRT
<213> ORGANISM: Artificial Sequence
<220> FEATURE:
<223> OTHER INFORMATION: chemically synthesized

<400> SEQUENCE: 45

Arg Ile Asp Ser Asp Asp Glu Lys His Tyr Asn Thr Ser Leu Lys Thr
1               5                   10                  15

<210> SEQ ID NO 46
<211> LENGTH: 12
<212> TYPE: PRT
<213> ORGANISM: Artificial Sequence
<220> FEATURE:
<223> OTHER INFORMATION: chemically synthesized

<400> SEQUENCE: 46

Leu Arg Ala Gly Ser Gly Pro Tyr Val Phe Asp Ser
1               5                   10

<210> SEQ ID NO 47
<211> LENGTH: 13
<212> TYPE: PRT
<213> ORGANISM: Artificial Sequence
<220> FEATURE:
<223> OTHER INFORMATION: chemically synthesized

<400> SEQUENCE: 47

Ser Gly Ser Ser Ser Asn Ile Gly Ser Asn Thr Val Asn
1               5                   10

<210> SEQ ID NO 48
<211> LENGTH: 7
<212> TYPE: PRT
<213> ORGANISM: Artificial Sequence
<220> FEATURE:
<223> OTHER INFORMATION: chemically synthesized

<400> SEQUENCE: 48

Asn Asn Asp Gln Arg Pro Ser
1               5

<210> SEQ ID NO 49
<211> LENGTH: 11
<212> TYPE: PRT
```

<213> ORGANISM: Artificial Sequence
<220> FEATURE:
<223> OTHER INFORMATION: chemically synthesized

<400> SEQUENCE: 49

Ala Ser Trp Asp Asp Ser Leu Asn Gly Arg Val
1               5                   10

<210> SEQ ID NO 50
<211> LENGTH: 369
<212> TYPE: DNA
<213> ORGANISM: Artificial Sequence
<220> FEATURE:
<223> OTHER INFORMATION: chemically synthesized

<400> SEQUENCE: 50
caggtgcagc tggtggagtc tgggggaggc gtggtccggc ctggggaggtc cctgagactc      60 tcctgtgcag cctctggatt caccttcagt agctatggca tgcactgggt ccgccaggct     120
ccaggcaagg ggctggagtg ggtggcagtt atatcatatg atggaagtat taaatactat     180
gcagactccg tgaagggccg attcaccatc tccagagaca attccaagaa cacgctgtat     240
ctgcaaatga acagcctgag agctgaggac acggccattt attactgtgc gagagtgatg     300
gggacggatc cccactccta ctactacatg gacgtctggg ggaaggggac cctggtcacc     360
gtctcgagt                                                              369

<210> SEQ ID NO 51
<211> LENGTH: 123
<212> TYPE: PRT
<213> ORGANISM: Artificial Sequence
<220> FEATURE:
<223> OTHER INFORMATION: chemically synthesized

<400> SEQUENCE: 51

Gln Val Gln Leu Val Glu Ser Gly Gly Gly Val Val Arg Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Val Met Gly Thr Asp Pro His Ser Tyr Tyr Tyr Met Asp Val
            100                 105                 110

Trp Gly Lys Gly Thr Leu Val Thr Val Ser Ser
        115                 120

<210> SEQ ID NO 52
<211> LENGTH: 14
<212> TYPE: PRT
<213> ORGANISM: Artificial Sequence
<220> FEATURE:
<223> OTHER INFORMATION: chemically synthesized

<400> SEQUENCE: 52

Val Met Gly Thr Asp Pro His Ser Tyr Tyr Tyr Met Asp Val
1               5                   10

<210> SEQ ID NO 53
<211> LENGTH: 354
<212> TYPE: DNA
<213> ORGANISM: Artificial Sequence
<220> FEATURE:
<223> OTHER INFORMATION: chemically synthesized

<400> SEQUENCE: 53

```
caggtgcagc tggtggagtc tgggggaggc gtggtccagc ctggggaggtc cctgagactc      60 tcctgtgcag cctctggatt caccttcagt agctatggca tgcactgggt ccgccaggct     120
ccaggcaagg gctggagtg gtggcagtt atatcatatg atggaagtat taaatactat     180
gcagactccg tgaagggccg attcaccatc tccagagaca attccaagaa cacgctgtat     240
ctgcaaatga acagcctgag agctgaggac cggctgtgt attactgtgc gagagcacca     300
gatggccacc aacttgacta ctggggcagg ggcaccctgg tcaccgtctc gagt          354
```

<210> SEQ ID NO 54
<211> LENGTH: 118
<212> TYPE: PRT
<213> ORGANISM: Artificial Sequence
<220> FEATURE:
<223> OTHER INFORMATION: chemically synthesized

<400> SEQUENCE: 54

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Ile Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
             85                  90                  95

Ala Arg Ala Pro Asp Gly His Gln Leu Asp Tyr Trp Gly Arg Gly Thr
        100                 105                 110

Leu Val Thr Val Ser Ser
        115
```

<210> SEQ ID NO 55
<211> LENGTH: 330
<212> TYPE: DNA
<213> ORGANISM: Artificial Sequence
<220> FEATURE:
<223> OTHER INFORMATION: chemically synthesized

<400> SEQUENCE: 55

```
aattttatgc tgactcagcc ccactctgtg tcggagtctc cggggaagac ggtaaccatc      60
tcctgcaccg gcagcagtgg cagcattgcc agcaactatg tgcagtggta ccagcagcgc     120
ccgggcagtg cccccaccac tgtgatctat gaagatgacc aaagacccctc tgacgtccct     180 gatcgcttct ctggctccat cgacagctcc tccaactctg cctccctcac catctctgga     240
ctgaggactg aggacgaggc tgactactac tgtcagtctt atgttagcag caagtgggtg     300
ttcggcggag ggaccaagct gaccgtccta                                      330
```

<210> SEQ ID NO 56

<211> LENGTH: 110
<212> TYPE: PRT
<213> ORGANISM: Artificial Sequence
<220> FEATURE:
<223> OTHER INFORMATION: chemically synthesized

<400> SEQUENCE: 56

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
        35                  40                  45

Ile Tyr Glu Asp Asp Gln Arg Pro Ser Asp Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Val Ser
                85                  90                  95

Ser Lys Trp Val Phe Gly Gly Gly Thr Lys Leu Thr Val Leu
            100                 105                 110

<210> SEQ ID NO 57
<211> LENGTH: 9
<212> TYPE: PRT
<213> ORGANISM: Artificial Sequence
<220> FEATURE:
<223> OTHER INFORMATION: chemically synthesized

<400> SEQUENCE: 57

Ala Pro Asp Gly His Gln Leu Asp Tyr
1               5

<210> SEQ ID NO 58
<211> LENGTH: 7
<212> TYPE: PRT
<213> ORGANISM: Artificial Sequence
<220> FEATURE:
<223> OTHER INFORMATION: chemically synthesized

<400> SEQUENCE: 58

Glu Asp Asp Gln Arg Pro Ser
1               5

<210> SEQ ID NO 59
<211> LENGTH: 9
<212> TYPE: PRT
<213> ORGANISM: Artificial Sequence
<220> FEATURE:
<223> OTHER INFORMATION: chemically synthesized

<400> SEQUENCE: 59

Gln Ser Tyr Val Ser Ser Lys Trp Val
1               5

<210> SEQ ID NO 60
<211> LENGTH: 402
<212> TYPE: DNA
<213> ORGANISM: Artificial Sequence
<220> FEATURE:
<223> OTHER INFORMATION: chemically synthesized

<400> SEQUENCE: 60
caggtgcagc tggtgcagtc tggggctgag gtgaagaagc ctgggtcctc ggtgacggtc        60

```
tcctgcaagg cctctggagg caccttcagc agcttttcta tcacctggct gcgacaggcc    120
cctggacaag gcttgagtg gatgggagag atcaccccta tgtttggtat agcaaactac    180
gcacagaagt tccagggtag ggtcacgatt agcgcggacg agtccacgag cacagcctac    240
atggagttga gtggcctgac atctgaagac acggccatgt attattgtgc gagagatggt    300
cggtttgatg tttccgatct tttgactgac aaacccaaag taacgataaa ctacaacggg    360
atggacgtct ggggccaagg caccctggtc accgtctcga gt                      402
```

<210> SEQ ID NO 61
<211> LENGTH: 134
<212> TYPE: PRT
<213> ORGANISM: Artificial Sequence
<220> FEATURE:
<223> OTHER INFORMATION: chemically synthesized

<400> SEQUENCE: 61

```
Gln Val Gln Leu Val Gln Ser Gly Ala Glu Val Lys Lys Pro Gly Ser
1               5                   10                  15

Ser Val Thr Val Ser Cys Lys Ala Ser Gly Gly Thr Phe Ser Ser Phe
            20                  25                  30

Ser Ile Thr Trp Leu Arg Gln Ala Pro Gly Gln Gly Leu Glu Trp Met
        35                  40                  45

Gly Glu Ile Thr Pro Met Phe Gly Ile Ala Asn Tyr Ala Gln Lys Phe
    50                  55                  60

Gln Gly Arg Val Thr Ile Ser Ala Asp Glu Ser Thr Ser Thr Ala Tyr
65                  70                  75                  80

Met Glu Leu Ser Gly Leu Thr Ser Glu Asp Thr Ala Met Tyr Tyr Cys
                85                  90                  95

Ala Arg Asp Gly Arg Phe Asp Val Ser Asp Leu Leu Thr Asp Lys Pro
            100                 105                 110

Lys Val Thr Ile Asn Tyr Asn Gly Met Asp Val Trp Gly Gln Gly Thr
        115                 120                 125

Leu Val Thr Val Ser Ser
    130
```

<210> SEQ ID NO 62
<211> LENGTH: 330
<212> TYPE: DNA
<213> ORGANISM: Artificial Sequence
<220> FEATURE:
<223> OTHER INFORMATION: chemically synthesized

<400> SEQUENCE: 62

```
cagtctgtgc tgactcagcc accctcagcg tctgggaccc ccgggcagag ggtcaccatc     60
tcttgttctg gaagcagctc caacatcggg agtaacactg taaactggta ccagcgactc    120
ccaggagcgg ccccccaact cctcatctac aataatgacc agcggccctc agggatccct    180
gaccgattct ctggctccaa gtctggcacc tcaggctccc tggtcatcag tgggctccag    240
tctgaagatg aggctgatta ctactgtgcg tcatgggatg acagtctgaa tggtcgggtg    300
ttcggcggag ggaccaagct gaccgtccta                                     330
```

<210> SEQ ID NO 63
<211> LENGTH: 110
<212> TYPE: PRT
<213> ORGANISM: Artificial Sequence
<220> FEATURE:
<223> OTHER INFORMATION: chemically synthesized

<400> SEQUENCE: 63

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Arg Leu Pro Gly Ala Ala Pro Gln Leu Leu
        35                  40                  45

Ile Tyr Asn Asn Asp Gln Arg Pro Ser Gly Ile Pro Asp Arg Phe Ser
50                  55                  60

Gly Ser Lys Ser Gly Thr Ser Gly Ser Leu Val Ile Ser Gly Leu Gln
65                  70                  75                  80

Ser Glu Asp Glu Ala Asp Tyr Tyr Cys Ala Ser Trp Asp Ser Leu
                85                  90                  95

Asn Gly Arg Val Phe Gly Gly Gly Thr Lys Leu Thr Val Leu
            100                 105                 110

<210> SEQ ID NO 64
<211> LENGTH: 5
<212> TYPE: PRT
<213> ORGANISM: Artificial Sequence
<220> FEATURE:
<223> OTHER INFORMATION: chemically synthesized

<400> SEQUENCE: 64

Ser Phe Ser Ile Thr
1               5

<210> SEQ ID NO 65
<211> LENGTH: 17
<212> TYPE: PRT
<213> ORGANISM: Artificial Sequence
<220> FEATURE:
<223> OTHER INFORMATION: chemically synthesized

<400> SEQUENCE: 65

Glu Ile Thr Pro Met Phe Gly Ile Ala Asn Tyr Ala Gln Lys Phe Gln
1               5                   10                  15

Gly

<210> SEQ ID NO 66
<211> LENGTH: 25
<212> TYPE: PRT
<213> ORGANISM: Artificial Sequence
<220> FEATURE:
<223> OTHER INFORMATION: chemically synthesized

<400> SEQUENCE: 66

Asp Gly Arg Phe Asp Val Ser Asp Leu Leu Thr Asp Lys Pro Lys Val
1               5                   10                  15

Thr Ile Asn Tyr Asn Gly Met Asp Val
            20                  25

<210> SEQ ID NO 67
<211> LENGTH: 378
<212> TYPE: DNA
<213> ORGANISM: Artificial Sequence
<220> FEATURE:
<223> OTHER INFORMATION: chemically synthesized

<400> SEQUENCE: 67
cagctggtgg agtctggagg aggcttgatc cagcctgggg ggtccctgag actttcctgt    60
gcagcctctg gattcagcgt cagtgacacc tacatgaact gggtccgcca ggctccaggg   120
```

```
aagggcctgg agtgggtgtc aagtatttat agcgatgata gcacatacta cgcagactcc    180
gtgaagggca gattcaccat ctccagagac aattccaaga acacgctgtt tcttcaaata    240
aacagtttga gaccgagga cacggctgtc tattactgtg cgagagataa ggagtatgta    300
```
*(line 3 reading: aacagtttga gagccgagga cacggctgtc tattactgtg cgagagataa ggagtatgta)*

```
acatcaactg ggggcgccta ctactacttc tactacatgg acgtctgggg ccagggcacc    360
ctggtcaccg tctcgagt                                                  378
```

<210> SEQ ID NO 68
<211> LENGTH: 126
<212> TYPE: PRT
<213> ORGANISM: Artificial Sequence
<220> FEATURE:
<223> OTHER INFORMATION: chemically synthesized

<400> SEQUENCE: 68

```
Gln Leu Val Glu Ser Gly Gly Gly Leu Ile Gln Pro Gly Gly Ser Leu
1               5                   10                  15

Arg Leu Ser Cys Ala Ala Ser Gly Phe Ser Val Ser Asp Thr Tyr Met
            20                  25                  30

Asn Trp Val Arg Gln Ala Pro Gly Lys Gly Leu Glu Trp Val Ser Ser
        35                  40                  45

Ile Tyr Ser Asp Asp Ser Thr Tyr Tyr Ala Asp Ser Val Lys Gly Arg
    50                  55                  60

Phe Thr Ile Ser Arg Asp Asn Ser Lys Asn Thr Leu Phe Leu Gln Ile
65                  70                  75                  80

Asn Ser Leu Arg Ala Glu Asp Thr Ala Val Tyr Tyr Cys Ala Arg Asp
                85                  90                  95

Lys Glu Tyr Val Thr Ser Thr Gly Gly Ala Tyr Tyr Tyr Phe Tyr Tyr
            100                 105                 110

Met Asp Val Trp Gly Gln Gly Thr Leu Val Thr Val Ser Ser
        115                 120                 125
```

<210> SEQ ID NO 69
<211> LENGTH: 330
<212> TYPE: DNA
<213> ORGANISM: Artificial Sequence
<220> FEATURE:
<223> OTHER INFORMATION: chemically synthesized

<400> SEQUENCE: 69

```
cagtctgtgc tgactcagcc accctcagcg tctgggaccc ccgggcagag agtctccatc     60
tcctgttctg gaagcagctc caacatcgga agtgatactg taactgtgta ccagcacctc    120
ccaggaacgg ccccccaaact cctcatctat aataataatc agcggccctc aggggtccct    180
gaccgattct ctggctccaa gtctggcacc tcagcctccc tggccatcag tgggctccag    240
tctgaggatg aggctgatta ttactgtgcc gcatgggatg acagcctgaa tggtctggta    300
ttcggcggag ggaccaaggt caccgtccta                                     330
```

<210> SEQ ID NO 70
<211> LENGTH: 110
<212> TYPE: PRT
<213> ORGANISM: Artificial Sequence
<220> FEATURE:
<223> OTHER INFORMATION: chemically synthesized

<400> SEQUENCE: 70

```
Gln Ser Val Leu Thr Gln Pro Pro Ser Ala Ser Gly Thr Pro Gly Gln
1               5                   10                  15

Arg Val Ser Ile Ser Cys Ser Gly Ser Ser Ser Asn Ile Gly Ser Asp
```

```
                20                  25                  30
Thr Val Asn Trp Tyr Gln His Leu Pro Gly Thr Ala Pro Lys Leu Leu
             35                  40                  45

Ile Tyr Asn Asn Asn Gln Arg Pro Ser Gly Val Pro Asp Arg Phe Ser
         50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Leu Val Phe Gly Gly Gly Thr Lys Val Thr Val Leu
            100                 105                 110
```

<210> SEQ ID NO 71
<211> LENGTH: 13
<212> TYPE: PRT
<213> ORGANISM: Artificial Sequence
<220> FEATURE:
<223> OTHER INFORMATION: chemically synthesized

<400> SEQUENCE: 71

```
Ser Gly Ser Ser Ser Asn Ile Gly Ser Asp Thr Val Asn
 1               5                  10
```

<210> SEQ ID NO 72
<211> LENGTH: 7
<212> TYPE: PRT
<213> ORGANISM: Artificial Sequence
<220> FEATURE:
<223> OTHER INFORMATION: chemically synthesized

<400> SEQUENCE: 72

```
Asn Asn Asn Gln Arg Pro Ser
 1               5
```

<210> SEQ ID NO 73
<211> LENGTH: 11
<212> TYPE: PRT
<213> ORGANISM: Artificial Sequence
<220> FEATURE:
<223> OTHER INFORMATION: chemically synthesized

<400> SEQUENCE: 73

```
Ala Ala Trp Asp Asp Ser Leu Asn Gly Leu Val
 1               5                  10
```

<210> SEQ ID NO 74
<211> LENGTH: 351
<212> TYPE: DNA
<213> ORGANISM: Artificial Sequence
<220> FEATURE:
<223> OTHER INFORMATION: chemically synthesized

<400> SEQUENCE: 74

```
caggtgcagc tggtggagtc tgggggaggc gtggtccagc ctggaggtc cctgagactc      60
tcctgtgcag cctctggatt caccttcagt agctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagacgag    300
tttgatgctt ttgatatctg gggccgaggg acaatggtca ccgtctcgag t             351
```

<210> SEQ ID NO 75

<211> LENGTH: 117
<212> TYPE: PRT
<213> ORGANISM: Artificial Sequence
<220> FEATURE:
<223> OTHER INFORMATION: chemically synthesized

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Glu Phe Asp Ala Phe Asp Ile Trp Gly Arg Gly Thr Met
            100                 105                 110

Val Thr Val Ser Ser
        115

<210> SEQ ID NO 76
<211> LENGTH: 324
<212> TYPE: DNA
<213> ORGANISM: Artificial Sequence
<220> FEATURE:
<223> OTHER INFORMATION: chemically synthesized

<400> SEQUENCE: 76
tcctatgtgc tgactcagcc ccccctcagtg tcggtggccc caggaacgac ggccaggatt    60
acctgtgggg gaaacaatat cggaagtagg agtgtgcatt ggtaccagca gaagccaggc   120 caggccccctc tactggtcat ctattatgat agtgaccggc cctcagggat ccctctgcga   180
ttctctggct ccaactctgg aaacacggcc accctgacca tcagtagggt cgaagccggg   240
gatgaggccg actattactg tcaggtgtgg gatactagta gtggtcatta tgtcttcgga   300
actgggacca aggtcaccgt ccta                                           324

<210> SEQ ID NO 77
<211> LENGTH: 108
<212> TYPE: PRT
<213> ORGANISM: Artificial Sequence
<220> FEATURE:
<223> OTHER INFORMATION: chemically synthesized

<400> SEQUENCE: 77

Ser Tyr Val Leu Thr Gln Pro Pro Ser Val Ser Val Ala Pro Gly Thr
1               5                   10                  15

Thr Ala Arg Ile Thr Cys Gly Gly Asn Asn Ile Gly Ser Arg Ser Val
            20                  25                  30

His Trp Tyr Gln Gln Lys Pro Gly Gln Ala Pro Leu Leu Val Ile Tyr
        35                  40                  45

Tyr Asp Ser Asp Arg Pro Ser Gly Ile Pro Leu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Ser Ser Gly His

```
                        85                  90                  95
Tyr Val Phe Gly Thr Gly Thr Lys Val Thr Val Leu
            100                 105

<210> SEQ ID NO 78
<211> LENGTH: 8
<212> TYPE: PRT
<213> ORGANISM: Artificial Sequence
<220> FEATURE:
<223> OTHER INFORMATION: chemically synthesized

<400> SEQUENCE: 78

Asp Glu Phe Asp Ala Phe Asp Ile
1               5

<210> SEQ ID NO 79
<211> LENGTH: 11
<212> TYPE: PRT
<213> ORGANISM: Artificial Sequence
<220> FEATURE:
<223> OTHER INFORMATION: chemically synthesized

<400> SEQUENCE: 79

Gly Gly Asn Asn Ile Gly Ser Arg Ser Val His
1               5                   10

<210> SEQ ID NO 80
<211> LENGTH: 7
<212> TYPE: PRT
<213> ORGANISM: Artificial Sequence
<220> FEATURE:
<223> OTHER INFORMATION: chemically synthesized

<400> SEQUENCE: 80

Tyr Asp Ser Asp Arg Pro Ser
1               5

<210> SEQ ID NO 81
<211> LENGTH: 11
<212> TYPE: PRT
<213> ORGANISM: Artificial Sequence
<220> FEATURE:
<223> OTHER INFORMATION: chemically synthesized

<400> SEQUENCE: 81

Gln Val Trp Asp Thr Ser Ser Gly His Tyr Val
1               5                   10

<210> SEQ ID NO 82
<211> LENGTH: 354
<212> TYPE: DNA
<213> ORGANISM: Artificial Sequence
<220> FEATURE:
<223> OTHER INFORMATION: chemically synthesized

<400> SEQUENCE: 82
cagctggtgg agtctggggg aggcgtggtc cagcctggga ggtccctgag actctcctgt      60
gcagcctctg gattcacctt cagtacctat ggcatgcact gggtccgcca ggctccaggc     120
aaggggctgg agtgggtggc agttatatca tatgatggag gtactaaata ctatgcagac     180
tccgtgaagg gccgattcac catctccaga gacaattcca tgaaaacgct ctatctgcaa     240
atgaacagcc tgagaactga ggacacggct gtgtattact gtgcgaaaga tctgggggac     300
ctaccccggg ccttgactac tggggccag gggacaatgg tcaccgtctc gagt            354
```

```
<210> SEQ ID NO 83
<211> LENGTH: 118
<212> TYPE: PRT
<213> ORGANISM: Artificial Sequence
<220> FEATURE:
<223> OTHER INFORMATION: chemically synthesized

<400> SEQUENCE: 83

Gln Leu Val Glu Ser Gly Gly Val Val Gln Pro Gly Arg Ser Leu
1               5                   10                  15

Arg Leu Ser Cys Ala Ala Ser Gly Phe Thr Phe Ser Thr Tyr Gly Met
            20                  25                  30

His Trp Val Arg Gln Ala Pro Gly Lys Gly Leu Glu Trp Val Ala Val
        35                  40                  45

Ile Ser Tyr Asp Gly Gly Thr Lys Tyr Tyr Ala Asp Ser Val Lys Gly
    50                  55                  60

Arg Phe Thr Ile Ser Arg Asp Asn Ser Met Lys Thr Leu Tyr Leu Gln
65                  70                  75                  80

Met Asn Ser Leu Arg Thr Glu Asp Thr Ala Val Tyr Tyr Cys Ala Lys
                85                  90                  95

Asp Leu Gly Asp Leu Pro Pro Gly Leu Asp Tyr Trp Gly Gln Gly Thr
            100                 105                 110

Met Val Thr Val Ser Ser
        115

<210> SEQ ID NO 84
<211> LENGTH: 333
<212> TYPE: DNA
<213> ORGANISM: Artificial Sequence
<220> FEATURE:
<223> OTHER INFORMATION: chemically synthesized

<400> SEQUENCE: 84
cagtctgtgc tgactcagcc acccctcagcg tctgggaccc ccgggcagag ggtcaccatc      60
tcttgttctg gaagcagctc caacatcgga agtaatactg taaactggta ccagcagctc     120
ccaggagcgg cccccaaact cctcatctat actaataatc agcggccctc aggggtccct     180
gaccgattct ctggctccaa gtctggcacc tcagcctccc tggccatcag tgggctccag     240
tctgaggatg aggctgatta ttactgtgca gcatgggatg acagcctgaa tggtaatgtg     300
gtattcggcg gagggaccaa ggtcaccgtc cta                                   333

<210> SEQ ID NO 85
<211> LENGTH: 111
<212> TYPE: PRT
<213> ORGANISM: Artificial Sequence
<220> FEATURE:
<223> OTHER INFORMATION: chemically synthesized

<400> SEQUENCE: 85

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Ala Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80
```

-continued

```
Ser Glu Asp Glu Ala Asp Tyr Tyr Cys Ala Ala Trp Asp Asp Ser Leu
            85                  90                  95

Asn Gly Asn Val Val Phe Gly Gly Gly Thr Lys Val Thr Val Leu
        100                 105                 110
```

<210> SEQ ID NO 86
<211> LENGTH: 5
<212> TYPE: PRT
<213> ORGANISM: Artificial Sequence
<220> FEATURE:
<223> OTHER INFORMATION: chemically synthesized

<400> SEQUENCE: 86

```
Thr Tyr Gly Met His
1               5
```

<210> SEQ ID NO 87
<211> LENGTH: 17
<212> TYPE: PRT
<213> ORGANISM: Artificial Sequence
<220> FEATURE:
<223> OTHER INFORMATION: chemically synthesized

<400> SEQUENCE: 87

```
Val Ile Ser Tyr Asp Gly Gly Thr Lys Tyr Tyr Ala Asp Ser Val Lys
1               5                   10                  15

Gly
```

<210> SEQ ID NO 88
<211> LENGTH: 11
<212> TYPE: PRT
<213> ORGANISM: Artificial Sequence
<220> FEATURE:
<223> OTHER INFORMATION: chemically synthesized

<400> SEQUENCE: 88

```
Asp Leu Gly Asp Leu Pro Pro Gly Leu Asp Tyr
1               5                   10
```

<210> SEQ ID NO 89
<211> LENGTH: 7
<212> TYPE: PRT
<213> ORGANISM: Artificial Sequence
<220> FEATURE:
<223> OTHER INFORMATION: chemically synthesized

<400> SEQUENCE: 89

```
Thr Asn Asn Gln Arg Pro Ser
1               5
```

<210> SEQ ID NO 90
<211> LENGTH: 12
<212> TYPE: PRT
<213> ORGANISM: Artificial Sequence
<220> FEATURE:
<223> OTHER INFORMATION: chemically synthesized

<400> SEQUENCE: 90

```
Ala Ala Trp Asp Asp Ser Leu Asn Gly Asn Val Val
1               5                   10
```

<210> SEQ ID NO 91
<211> LENGTH: 351
<212> TYPE: DNA
<213> ORGANISM: Artificial Sequence
<220> FEATURE:
<223> OTHER INFORMATION: chemically synthesized

<400> SEQUENCE: 91

```
caggtgcagc tggtggagtc tgggggaggc gtggctcagt ctgggaagtc cctgagactc      60
tcctgtgcag cctctggatt caccttcagt aactatggca tgcactgggt ccgccaggct     120
ccaggcaagg gctggagtg gctggcagtc atatcatatg atggaagtaa cagatactat     180
gcagactccg tgaagggccg attcaccatc tccagagaca attccaacaa cacactgaat     240
ctgcaaatga gcagcctgag agctgaggac acggctctat attactgtgc gaaagatgcc     300
ggggggccgc ttgattactg ggcaagggc accctggtca ccgtctcgag t               351
```

<210> SEQ ID NO 92
<211> LENGTH: 117
<212> TYPE: PRT
<213> ORGANISM: Artificial Sequence
<220> FEATURE:
<223> OTHER INFORMATION: chemically synthesized

<400> SEQUENCE: 92

```
Gln Val Gln Leu Val Glu Ser Gly Gly Gly Val Ala Gln Ser Gly Lys
1               5                   10                  15
Ser Leu Arg Leu Ser Cys Ala Ala Ser Gly Phe Thr Phe Ser Asn Tyr
            20                  25                  30
Gly Met His Trp Val Arg Gln Ala Pro Gly Lys Gly Leu Glu Trp Leu
        35                  40                  45
Ala Val Ile Ser Tyr Asp Gly Ser Asn Arg Tyr Tyr Ala Asp Ser Val
    50                  55                  60
Lys Gly Arg Phe Thr Ile Ser Arg Asp Asn Ser Asn Asn Thr Leu Asn
65                  70                  75                  80
Leu Gln Met Ser Ser Leu Arg Ala Glu Asp Thr Ala Leu Tyr Tyr Cys
                85                  90                  95
Ala Lys Asp Ala Gly Gly Pro Leu Asp Tyr Trp Gly Lys Gly Thr Leu
            100                 105                 110
Val Thr Val Ser Ser
        115
```

<210> SEQ ID NO 93
<211> LENGTH: 337
<212> TYPE: DNA
<213> ORGANISM: Artificial Sequence
<220> FEATURE:
<223> OTHER INFORMATION: chemically synthesized

<400> SEQUENCE: 93

```
cagtctgtgc tgactcagct gactcagcca cctcggtgt cactggcccc aggacagacg      60
gccaccatta cttgtggggg agacaacatt ggacgtaaaa gtgtgcactg gtaccagcag     120
aagccaggcc aggcccctgt gttggtcgtc tatgatgaca ccgaccggcc ctcagggatc     180
cctgagcgat tctctggctc caactctggg aacacggcca ccctaaccat cagcagggtc     240
gaagccgggg atgaggccga ctattactgt caggtgtggg atagtagtat tgatcattct     300
tgggtgttcg gcggagggac caagctgacc gtcctag                              337
```

<210> SEQ ID NO 94
<211> LENGTH: 112
<212> TYPE: PRT
<213> ORGANISM: Artificial Sequence
<220> FEATURE:
<223> OTHER INFORMATION: chemically synthesized

<400> SEQUENCE: 94

```
Gln Ser Val Leu Thr Gln Leu Thr Gln Pro Pro Ser Val Ser Leu Ala
1               5                   10                  15

Pro Gly Gln Thr Ala Thr Ile Thr Cys Gly Gly Asp Asn Ile Gly Arg
            20                  25                  30

Lys Ser Val His Trp Tyr Gln Lys Pro Gly Gln Ala Pro Val Leu
        35                  40                  45

Val Val Tyr Asp Asp Thr Asp Arg Pro Ser Ile Pro Glu Arg Phe
50                  55                  60

Ser Gly Ser Asn Ser Gly Asn Thr Ala Thr Leu Thr Ile Ser Arg Val
65                  70                  75                  80

Glu Ala Gly Asp Glu Ala Asp Tyr Tyr Cys Gln Val Trp Asp Ser Ser
                85                  90                  95

Ile Asp His Ser Trp Val Phe Gly Gly Gly Thr Lys Leu Thr Val Leu
                100                 105                 110

<210> SEQ ID NO 95
<211> LENGTH: 5
<212> TYPE: PRT
<213> ORGANISM: Artificial Sequence
<220> FEATURE:
<223> OTHER INFORMATION: chemically synthesized

<400> SEQUENCE: 95

Asn Tyr Gly Met His
1               5

<210> SEQ ID NO 96
<211> LENGTH: 17
<212> TYPE: PRT
<213> ORGANISM: Artificial Sequence
<220> FEATURE:
<223> OTHER INFORMATION: chemically synthesized

<400> SEQUENCE: 96

Val Ile Ser Tyr Asp Gly Ser Asn Arg Tyr Tyr Ala Asp Ser Val Lys
1               5                   10                  15

Gly

<210> SEQ ID NO 97
<211> LENGTH: 8
<212> TYPE: PRT
<213> ORGANISM: Artificial Sequence
<220> FEATURE:
<223> OTHER INFORMATION: chemically synthesized

<400> SEQUENCE: 97

Asp Ala Gly Gly Pro Leu Asp Tyr
1               5

<210> SEQ ID NO 98
<211> LENGTH: 11
<212> TYPE: PRT
<213> ORGANISM: Artificial Sequence
<220> FEATURE:
<223> OTHER INFORMATION: chemically synthesized

<400> SEQUENCE: 98

Gly Gly Asp Asn Ile Gly Arg Lys Ser Val His
1               5                   10

<210> SEQ ID NO 99
<211> LENGTH: 7
<212> TYPE: PRT
```

<213> ORGANISM: Artificial Sequence
<220> FEATURE:
<223> OTHER INFORMATION: chemically synthesized

<400> SEQUENCE: 99

Asp Asp Thr Asp Arg Pro Ser
1               5

<210> SEQ ID NO 100
<211> LENGTH: 12
<212> TYPE: PRT
<213> ORGANISM: Artificial Sequence
<220> FEATURE:
<223> OTHER INFORMATION: chemically synthesized

<400> SEQUENCE: 100

Gln Val Trp Asp Ser Ser Ile Asp His Ser Trp Val
1               5                   10

<210> SEQ ID NO 101
<211> LENGTH: 363
<212> TYPE: DNA
<213> ORGANISM: Artificial Sequence
<220> FEATURE:
<223> OTHER INFORMATION: chemically synthesized

<400> SEQUENCE: 101

```
caggtgcagc tggtggagtc tgggggaggc gtggtccagc ctggggaggtc cctgagactc    60
tcctgtgcag cctctggatt caccttcagt agctatggca tgcactgggt ccgccaggct   120
ccaggcaagg ggctggagtg ggtggcagtt atatcatatg atggaagtat aaaatactat   180
gcagactccg tgaagggccg attcaccatc tccagagaca attccaggaa cacgctgtat   240
ctgcagatga acagcctgag acctgaggac acggctgttt attactgtgc gaaagattgg   300
ggatttagcg gctccctaac atttgattat tggggccaag ggacaatggt caccgtctcg   360
agt                                                                 363
```

<210> SEQ ID NO 102
<211> LENGTH: 121
<212> TYPE: PRT
<213> ORGANISM: Artificial Sequence
<220> FEATURE:
<223> OTHER INFORMATION: chemically synthesized

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Trp Gly Phe Ser Gly Ser Leu Thr Phe Asp Tyr Trp Gly
            100                 105                 110

Gln Gly Thr Met Val Thr Val Ser Ser
        115                 120

<210> SEQ ID NO 103
<211> LENGTH: 324
<212> TYPE: DNA
<213> ORGANISM: Artificial Sequence
<220> FEATURE:
<223> OTHER INFORMATION: chemically synthesized

<400> SEQUENCE: 103

```
tcctatgtgc tgactcagcc accctcagtg tcagtggccc caggaaagac ggccaggatt      60
acctgtgggg gaaacaacat tggaagtaaa agtgtgcact ggtaccagca gaagccaggc     120
caggcccctg tgctggtcat ctattatgat agcgaccggc cctcaggat ccctgagcga      180 ttctctggct ccaactctgg gaacacggcc accctgacca tcagcagggt cgaagccggg     240
gatgaggccg actattactg tcaggtgtgg gatagtagta gtgatcatgt ggtattcggc     300
ggagggacca aggtcaccgt ccta                                            324
```

<210> SEQ ID NO 104
<211> LENGTH: 108
<212> TYPE: PRT
<213> ORGANISM: Artificial Sequence
<220> FEATURE:
<223> OTHER INFORMATION: chemically synthesized

<400> SEQUENCE: 104

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Val Thr Val Leu
            100                 105
```

<210> SEQ ID NO 105
<211> LENGTH: 12
<212> TYPE: PRT
<213> ORGANISM: Artificial Sequence
<220> FEATURE:
<223> OTHER INFORMATION: chemically synthesized

<400> SEQUENCE: 105

```
Asp Trp Gly Phe Ser Gly Ser Leu Thr Phe Asp Tyr
1               5                   10
```

<210> SEQ ID NO 106
<211> LENGTH: 11
<212> TYPE: PRT
<213> ORGANISM: Artificial Sequence
<220> FEATURE:
<223> OTHER INFORMATION: chemically synthesized

<400> SEQUENCE: 106

```
Gly Gly Asn Asn Ile Gly Ser Lys Ser Val His
1               5                   10
```

<210> SEQ ID NO 107
<211> LENGTH: 11
<212> TYPE: PRT
<213> ORGANISM: Artificial Sequence
<220> FEATURE:
<223> OTHER INFORMATION: chemically synthesized

<400> SEQUENCE: 107

Gln Val Trp Asp Ser Ser Asp His Val Val
1               5                   10

<210> SEQ ID NO 108
<211> LENGTH: 351
<212> TYPE: DNA
<213> ORGANISM: Artificial Sequence
<220> FEATURE:
<223> OTHER INFORMATION: chemically synthesized

<400> SEQUENCE: 108
caggtgcagc tggtggagtc tgggggaggc gtggctcact ctgggaagtc cctgagactc      60
tcctgtgcag cctctggatt caccttcagt aactatggca tgcactgggt ccgccaggct     120
ccaggcaagg ggctggagtg gctggcagtc atatcatatg atgggagtaa tagatactat     180
gcagactccg tgaagggccg attcaccatc tccagagaca attccaacaa cacgctgaat     240
ctgcaaatga gcagcctgag agctgaggac acggctctgt attactgtgc gaaagatgcc     300
ggggggccgc ttgattactg gggccggggc accctggtca ccgtctcgag t              351

<210> SEQ ID NO 109
<211> LENGTH: 117
<212> TYPE: PRT
<213> ORGANISM: Artificial Sequence
<220> FEATURE:
<223> OTHER INFORMATION: chemically synthesized

<400> SEQUENCE: 109

Gln Val Gln Leu Val Glu Ser Gly Gly Gly Val Ala His Ser Gly Lys
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Leu
        35                  40                  45

Ala Val Ile Ser Tyr Asp Gly Ser Asn Arg Tyr Tyr Ala Asp Ser Val
    50                  55                  60

Lys Gly Arg Phe Thr Ile Ser Arg Asp Asn Ser Asn Asn Thr Leu Asn
65                  70                  75                  80

Leu Gln Met Ser Ser Leu Arg Ala Glu Asp Thr Ala Leu Tyr Tyr Cys
                85                  90                  95

Ala Lys Asp Ala Gly Gly Pro Leu Asp Tyr Trp Gly Arg Gly Thr Leu
            100                 105                 110

Val Thr Val Ser Ser
        115

<210> SEQ ID NO 110
<211> LENGTH: 330
<212> TYPE: DNA
<213> ORGANISM: Artificial Sequence
<220> FEATURE:
<223> OTHER INFORMATION: chemically synthesized

<400> SEQUENCE: 110
tcctatgtgc tgactcagcc accctcggtg tcagtggccc caggacagat ggccagaatt      60

-continued

```
acctgtgggg gaaacaacat tggagataaa agtgtgcaat ggtaccagca gaggccaggc      120
caggcccctc tactggtcgt ctatgatgat agcgaccggc cctcaggat ccctgagcgc       180 ttctctggct cctactctag gaacacggcc accctgacca tcagcagggt cgaagccggg      240
gatgaggccg actattactg tcaggtgtgg gatagtagta gtgatcatcc ggaggtggtt      300
ttcggcggag ggaccaagct gaccgtccta                                        330
```

<210> SEQ ID NO 111
<211> LENGTH: 110
<212> TYPE: PRT
<213> ORGANISM: Artificial Sequence
<220> FEATURE:
<223> OTHER INFORMATION: chemically synthesized

<400> SEQUENCE: 111

Ser Tyr Val Leu Thr Gln Pro Pro Ser Val Ser Val Ala Pro Gly Gln
1               5                   10                  15

Met Ala Arg Ile Thr Cys Gly Gly Asn Asn Ile Gly Asp Lys Ser Val
            20                  25                  30

Gln Trp Tyr Gln Gln Arg Pro Gly Gln Ala Pro Leu Leu Val Val Tyr
        35                  40                  45

Asp Asp Ser Asp Arg Pro Ser Gly Ile Pro Glu Arg Phe Ser Gly Ser
    50                  55                  60

Tyr Ser Arg Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Pro Glu Val Val Phe Gly Gly Gly Thr Lys Leu Thr Val Leu
            100                 105                 110

<210> SEQ ID NO 112
<211> LENGTH: 11
<212> TYPE: PRT
<213> ORGANISM: Artificial Sequence
<220> FEATURE:
<223> OTHER INFORMATION: chemically synthesized

<400> SEQUENCE: 112

Gly Gly Asn Asn Ile Gly Asp Lys Ser Val Gln
1               5                   10

<210> SEQ ID NO 113
<211> LENGTH: 7
<212> TYPE: PRT
<213> ORGANISM: Artificial Sequence
<220> FEATURE:
<223> OTHER INFORMATION: chemically synthesized

<400> SEQUENCE: 113

Asp Asp Ser Asp Arg Pro Ser
1               5

<210> SEQ ID NO 114
<211> LENGTH: 13
<212> TYPE: PRT
<213> ORGANISM: Artificial Sequence
<220> FEATURE:
<223> OTHER INFORMATION: chemically synthesized

<400> SEQUENCE: 114

Gln Val Trp Asp Ser Ser Ser Asp His Pro Glu Val Val
1               5                   10

<210> SEQ ID NO 115
<211> LENGTH: 360
<212> TYPE: DNA
<213> ORGANISM: Artificial Sequence
<220> FEATURE:
<223> OTHER INFORMATION: chemically synthesized

<400> SEQUENCE: 115

```
caggtccagc tggtgcagtc tgggggaggc gtggtccagc ctggagagtc cctgagactc    60
tcctgtgcag cctctggatt caccttcagt acctatggca tgcactgggt ccgccaggct   120
ccaggcaagg ggctggagtg ggtggcagtt atatcatatg atggaggtac taaatactat   180
gcagactccg tgaagggccg attcaccatc tccagagaca attccatgaa aacgctctat   240
ctgcaaatga acagcctgag aactgaggac acggctgtgt attactgtgc gaaagatctg   300
ggggacctac ccccgggcct tgactactgg ggccgaggga caatggtcac cgtctcgagt   360
```

<210> SEQ ID NO 116
<211> LENGTH: 120
<212> TYPE: PRT
<213> ORGANISM: Artificial Sequence
<220> FEATURE:
<223> OTHER INFORMATION: chemically synthesized

<400> SEQUENCE: 116

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Gly Thr Lys Tyr Tyr Ala Asp Ser Val
    50                  55                  60

Lys Gly Arg Phe Thr Ile Ser Arg Asp Asn Ser Met Lys Thr Leu Tyr
65                  70                  75                  80

Leu Gln Met Asn Ser Leu Arg Thr Glu Asp Thr Ala Val Tyr Tyr Cys
                85                  90                  95

Ala Lys Asp Leu Gly Asp Leu Pro Pro Gly Leu Asp Tyr Trp Gly Arg
            100                 105                 110

Gly Thr Met Val Thr Val Ser Ser
        115                 120
```

<210> SEQ ID NO 117
<211> LENGTH: 321
<212> TYPE: DNA
<213> ORGANISM: Artificial Sequence
<220> FEATURE:
<223> OTHER INFORMATION: chemically synthesized

<400> SEQUENCE: 117

```
tcctatgagc tgactcagcc accctcagtg tcagtggccc tgggacagac ggccacgatt    60
acctgtgggg ggagcagtat tgagagtaaa agtgtacact ggtaccagga gaagccaggc   120
caggcccctg tcctggtcat ctataaagat tccaaccggc cctctgtgat ccctgagcga   180
ttctctggct ccaactcggg gaacacggcc accctgacca tcggcagagc ccaagccggg   240
gatgaggctg actattactg tcaggtgtgg gacagcagta ctggtgtggt attcggcgga   300
gggaccaagc tgaccgtcct a                                             321
```

<210> SEQ ID NO 118

```
<211> LENGTH: 128
<212> TYPE: PRT
<213> ORGANISM: Artificial Sequence
<220> FEATURE:
<223> OTHER INFORMATION: chemically synthesized

<400> SEQUENCE: 118

Cys His Glu Met Ile Cys Ala Leu Leu Tyr Ser Tyr Asn Thr His Glu
1               5                   10                  15

Ser Ile Glx Glu Asp Ser Tyr Glu Leu Thr Gln Pro Pro Ser Val Ser
            20                  25                  30

Val Ala Leu Gly Gln Thr Ala Thr Ile Thr Cys Gly Gly Ser Ser Ile
            35                  40                  45

Glu Ser Lys Ser Val His Trp Tyr Gln Glu Lys Pro Gly Gln Ala Pro
        50                  55                  60

Val Leu Val Ile Tyr Lys Asp Ser Asn Arg Pro Ser Val Ile Pro Glu
65                  70                  75                  80

Arg Phe Ser Gly Ser Asn Ser Gly Asn Thr Ala Thr Leu Thr Ile Gly
                85                  90                  95

Arg Ala Gln Ala Gly Asp Glu Ala Asp Tyr Tyr Cys Gln Val Trp Asp
            100                 105                 110

Ser Ser Thr Gly Val Val Phe Gly Gly Gly Thr Lys Leu Thr Val Leu
        115                 120                 125

<210> SEQ ID NO 119
<211> LENGTH: 11
<212> TYPE: PRT
<213> ORGANISM: Artificial Sequence
<220> FEATURE:
<223> OTHER INFORMATION: chemically synthesized

<400> SEQUENCE: 119

Gly Gly Ser Ser Ile Glu Ser Lys Ser Val His
1               5                   10

<210> SEQ ID NO 120
<211> LENGTH: 7
<212> TYPE: PRT
<213> ORGANISM: Artificial Sequence
<220> FEATURE:
<223> OTHER INFORMATION: chemically synthesized

<400> SEQUENCE: 120

Lys Asp Ser Asn Arg Pro Ser
1               5

<210> SEQ ID NO 121
<211> LENGTH: 10
<212> TYPE: PRT
<213> ORGANISM: Artificial Sequence
<220> FEATURE:
<223> OTHER INFORMATION: chemically synthesized

<400> SEQUENCE: 121

Gln Val Trp Asp Ser Ser Thr Gly Val Val
1               5                   10

<210> SEQ ID NO 122
<211> LENGTH: 360
<212> TYPE: DNA
<213> ORGANISM: Artificial Sequence
<220> FEATURE:
<223> OTHER INFORMATION: chemically synthesized

<400> SEQUENCE: 122
```

```
caggtccagt tggtggagtc tgggggaggc gtggtccagc ctgggaggtc cctgagactc      60
tcctgtgcag cctctggatt caccttcagt acctatggca tgcactgggt ccgccaggct     120
ccaggcaagg ggctggagtg ggtggcagtt atatcatatg atggaggtac taaatactat     180
gcagactccg tgaagggccg attcaccatc tccagagaca attccatgaa aacgctctat     240
ctgcaaatga acagcctgag aactgaggac acggctgtgt attactgtgc gaaagatctg     300
ggggacctac ccccgggcct tgactactgg ggccagggga caatggtcac cgtctcgagt     360
```

<210> SEQ ID NO 123
<211> LENGTH: 120
<212> TYPE: PRT
<213> ORGANISM: Artificial Sequence
<220> FEATURE:
<223> OTHER INFORMATION: chemically synthesized

<400> SEQUENCE: 123

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Ser Tyr Asp Gly Gly Thr Lys Tyr Tyr Ala Asp Ser Val
        50                  55                  60

Lys Gly Arg Phe Thr Ile Ser Arg Asp Asn Ser Met Lys Thr Leu Tyr
65                  70                  75                  80

Leu Gln Met Asn Ser Leu Arg Thr Glu Asp Thr Ala Val Tyr Tyr Cys
                85                  90                  95

Ala Lys Asp Leu Gly Asp Leu Pro Pro Gly Leu Asp Tyr Trp Gly Gln
            100                 105                 110

Gly Thr Met Val Thr Val Ser Ser
        115                 120
```

<210> SEQ ID NO 124
<211> LENGTH: 333
<212> TYPE: DNA
<213> ORGANISM: Artificial Sequence
<220> FEATURE:
<223> OTHER INFORMATION: chemically synthesized

<400> SEQUENCE: 124

```
cagtctgtgc tgactcagcc accctcagcg tctgggaccc ccgggcagag ggtcaccatc      60
tcttgttctg gaagcagctc caacatcgga agtaatactg taaactggta ccagcagctc     120
ccaggagcgg cccccaaact cctcatctat actaataatc agcggccctc aggggtcccc     180
gaccgattct ctggctccaa gtctggcacc tcagcctccc tggccatcag tgggctccag     240
tctgaggatg aggctgatta ttactgtgca gcatgggatg acagctcgga gcctcgtgtg     300
gtattcggcg gagggaccaa ggtcaccgtc cta                                  333
```

<210> SEQ ID NO 125
<211> LENGTH: 111
<212> TYPE: PRT
<213> ORGANISM: Artificial Sequence
<220> FEATURE:
<223> OTHER INFORMATION: chemically synthesized

<400> SEQUENCE: 125

```
Gln Ser Val Leu Thr Gln Pro Pro Ser Ala Ser Gly Thr Pro Gly Gln
```

```
                 1               5                  10                 15
Arg Val Thr Ile Ser Cys Ser Gly Ser Ser Asn Ile Gly Ser Asn
                20                  25                 30

Thr Val Asn Trp Tyr Gln Gln Leu Pro Gly Ala Ala Pro Lys Leu Leu
                35                  40                 45

Ile Tyr Thr Asn Asn Gln Arg Pro Ser Gly Val Pro Asp Arg Phe Ser
        50                  55                 60

Gly Ser Lys Ser Gly Thr Ser Ala Ser Leu Ala Ile Ser Gly Leu Gln
65                  70                  75                 80

Ser Glu Asp Glu Ala Asp Tyr Tyr Cys Ala Ala Trp Asp Asp Ser Ser
                85                  90                 95

Glu Pro Arg Val Val Phe Gly Gly Gly Thr Lys Val Thr Val Leu
                100                 105                110
```

<210> SEQ ID NO 126
<211> LENGTH: 12
<212> TYPE: PRT
<213> ORGANISM: Artificial Sequence
<220> FEATURE:
<223> OTHER INFORMATION: chemically synthesized

<400> SEQUENCE: 126

```
Ala Ala Trp Asp Asp Ser Ser Glu Pro Arg Val Val
1               5                  10
```

<210> SEQ ID NO 127
<211> LENGTH: 5
<212> TYPE: PRT
<213> ORGANISM: Artificial Sequence
<220> FEATURE:
<223> OTHER INFORMATION: chemically synthesized

<400> SEQUENCE: 127

```
Asp Thr Tyr Met Asn
1               5
```

<210> SEQ ID NO 128
<211> LENGTH: 16
<212> TYPE: PRT
<213> ORGANISM: Artificial Sequence
<220> FEATURE:
<223> OTHER INFORMATION: chemically synthesized

<400> SEQUENCE: 128

```
Ser Ile Tyr Ser Asp Asp Ser Thr Tyr Tyr Ala Asp Ser Val Lys Gly
1               5                  10                 15
```

<210> SEQ ID NO 129
<211> LENGTH: 20
<212> TYPE: PRT
<213> ORGANISM: Artificial Sequence
<220> FEATURE:
<223> OTHER INFORMATION: chemically synthesized

<400> SEQUENCE: 129

```
Asp Lys Glu Tyr Val Thr Ser Thr Gly Gly Ala Tyr Tyr Tyr Phe Tyr
1               5                  10                 15

Tyr Met Asp Val
                20
```

<210> SEQ ID NO 130
<211> LENGTH: 21
<212> TYPE: DNA
<213> ORGANISM: Artificial Sequence

```
<220> FEATURE:
<223> OTHER INFORMATION: chemically synthesized

<400> SEQUENCE: 130
ctcttctgag atgagttttt g                                              21

<210> SEQ ID NO 131
<211> LENGTH: 30
<212> TYPE: DNA
<213> ORGANISM: Artificial Sequence
<220> FEATURE:
<223> OTHER INFORMATION: chemically synthesized

<400> SEQUENCE: 131
ttattattcg caattccttt agttgttcct                                     30

<210> SEQ ID NO 132
<211> LENGTH: 10
<212> TYPE: PRT
<213> ORGANISM: Artificial Sequence
<220> FEATURE:
<223> OTHER INFORMATION: chemically synthesized

<400> SEQUENCE: 132

Asp Gly Ser Glu Ser Glu Tyr Leu Asp Tyr
1               5                   10

<210> SEQ ID NO 133
<211> LENGTH: 13
<212> TYPE: PRT
<213> ORGANISM: Artificial Sequence
<220> FEATURE:
<223> OTHER INFORMATION: chemically synthesized

<400> SEQUENCE: 133

Thr Gly Ser Ser Gly Ser Ile Ala Ser Asn Tyr Val Gln
1               5                   10

<210> SEQ ID NO 134
<211> LENGTH: 217
<212> TYPE: PRT
<213> ORGANISM: Artificial Sequence
<220> FEATURE:
<223> OTHER INFORMATION: chemically synthesized

<400> SEQUENCE: 134

Asn Phe Met Leu Thr Gln Pro His Ser Val Ser Glu Ser Pro Gly Lys
1               5                   10                  15

Thr Val Thr Ile Ser Cys Thr Gly Ser Gly Ser Ile Ala Ser Asn
            20                  25                  30

Tyr Val Gln Trp Tyr Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Pro
                85                  90                  95

Leu Pro Val Trp Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
```

```
              130                 135                 140
Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215

<210> SEQ ID NO 135
<211> LENGTH: 449
<212> TYPE: PRT
<213> ORGANISM: Artificial Sequence
<220> FEATURE:
<223> OTHER INFORMATION: chemically synthesized

<400> SEQUENCE: 135

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Ser
                20                  25                  30

Gly Ile His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Arg Asp Asn Ala Glu Tyr Thr Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 136
<211> LENGTH: 360
<212> TYPE: DNA
<213> ORGANISM: Artificial Sequence
<220> FEATURE:
<223> OTHER INFORMATION: chemically synthesized

<400> SEQUENCE: 136

```
gaggtgcagc tggtgcagtc tggggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagacggt     300
ggctggtacg actggtactt cgatctctgg ggcagggaa  ccctggtcac cgtctcgagt     360
```

<210> SEQ ID NO 137
<211> LENGTH: 120
<212> TYPE: PRT
<213> ORGANISM: Artificial Sequence
<220> FEATURE:
<223> OTHER INFORMATION: chemically synthesized

<400> SEQUENCE: 137

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Asp Gly Gly Trp Tyr Asp Trp Tyr Phe Asp Leu Trp Gly Arg
            100                 105                 110

Gly Thr Leu Val Thr Val Ser Ser
        115                 120

<210> SEQ ID NO 138
<211> LENGTH: 324
<212> TYPE: DNA
<213> ORGANISM: Artificial Sequence
<220> FEATURE:
<223> OTHER INFORMATION: chemically synthesized

<400> SEQUENCE: 138
tcttctgagc tgactcagga ccctgatgtg tccgtggcct tgggacagac agtcaggatc      60
acatgccaag agacagcct caccagctat tatgcaagct ggtaccagca gaagccagga     120
caggcccctg tacttgtcat ctctggtaat gacaaccggc cctcagggat cccagaccga     180
ttctctggct ccaactcagg aaacacagct tccttgacca tcactggggc tcaggcggaa     240
gatgcggctg actattactg tggctcccgg gacagcagcg gttaccaagt ggtgttcggc     300
gcagggacca agctgaccgt ccta                                           324

<210> SEQ ID NO 139
<211> LENGTH: 108
<212> TYPE: PRT
<213> ORGANISM: Artificial Sequence
<220> FEATURE:
<223> OTHER INFORMATION: chemically synthesized

<400> SEQUENCE: 139

Ser Ser Glu Leu Thr Gln Asp Pro Asp Val Ser Val Ala Leu Gly Gln
1               5                   10                  15

Thr Val Arg Ile Thr Cys Gln Gly Asp Ser Leu Thr Ser Tyr Tyr Ala
            20                  25                  30

Ser Trp Tyr Gln Gln Lys Pro Gly Gln Ala Pro Val Leu Val Ile Ser
        35                  40                  45

Gly Asn Asp Asn Arg Pro Ser Gly Ile Pro Asp Arg Phe Ser Gly Ser
    50                  55                  60

Asn Ser Gly Asn Thr Ala Ser Leu Thr Ile Thr Gly Ala Gln Ala Glu
65                  70                  75                  80

Asp Ala Ala Asp Tyr Tyr Cys Gly Ser Arg Asp Ser Ser Gly Tyr Gln
                85                  90                  95

Val Val Phe Gly Ala Gly Thr Lys Leu Thr Val Leu
            100                 105

<210> SEQ ID NO 140
<211> LENGTH: 11
<212> TYPE: PRT
<213> ORGANISM: Artificial Sequence
<220> FEATURE:
<223> OTHER INFORMATION: chemically synthesized

<400> SEQUENCE: 140

Asp Gly Gly Trp Tyr Asp Trp Tyr Phe Asp Leu
1               5                   10

<210> SEQ ID NO 141
<211> LENGTH: 11
<212> TYPE: PRT
<213> ORGANISM: Artificial Sequence
```

<220> FEATURE:
<223> OTHER INFORMATION: chemically synthesized

<400> SEQUENCE: 141

Gln Gly Asp Ser Leu Thr Ser Tyr Tyr Ala Ser
1               5                   10

<210> SEQ ID NO 142
<211> LENGTH: 7
<212> TYPE: PRT
<213> ORGANISM: Artificial Sequence
<220> FEATURE:
<223> OTHER INFORMATION: chemically synthesized

<400> SEQUENCE: 142

Gly Asn Asp Asn Arg Pro Ser
1               5

<210> SEQ ID NO 143
<211> LENGTH: 11
<212> TYPE: PRT
<213> ORGANISM: Artificial Sequence
<220> FEATURE:
<223> OTHER INFORMATION: chemically synthesized

<400> SEQUENCE: 143

Gly Ser Arg Asp Ser Ser Gly Tyr Gln Val Val
1               5                   10

<210> SEQ ID NO 144
<211> LENGTH: 324
<212> TYPE: DNA
<213> ORGANISM: Artificial Sequence
<220> FEATURE:
<223> OTHER INFORMATION: chemically synthesized

<400> SEQUENCE: 144
tcttctgagc tgactcagga ccctgctgtg tctgtggcct tgggacagac agtcaggatc      60
acatgccaag agacagcct cagaagctat tatgcaagct ggtaccagcg gaagccagga     120
caggcccctg tacttgtcat ctatggtaaa acaaccggc cctcagggat cccagaccga     180
ttctctggct ccagctcagg aaacacagct tccttgacca tcactggggc tcaggcggaa     240
gatgaggctg actattactg taactcccgg gacagcagtg gtaaccatgt gcttttcggc     300
ggagggacca agctgaccgt ccta                                            324

<210> SEQ ID NO 145
<211> LENGTH: 108
<212> TYPE: PRT
<213> ORGANISM: Artificial Sequence
<220> FEATURE:
<223> OTHER INFORMATION: chemically synthesized

<400> SEQUENCE: 145

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Arg Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

```
Asp Glu Ala Asp Tyr Tyr Cys Asn Ser Arg Asp Ser Ser Gly Asn His
                85                  90                  95

Val Leu Phe Gly Gly Gly Thr Lys Leu Thr Val Leu
            100                 105
```

<210> SEQ ID NO 146
<211> LENGTH: 93
<212> TYPE: PRT
<213> ORGANISM: Homo sapiens

<400> SEQUENCE: 146

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Asn Ser Ala Ser Leu Thr Ile Ser Gly Leu Lys
65                  70                  75                  80

Thr Glu Asp Glu Ala Asp Tyr Tyr Cys Gln Ser Tyr Asp
                85                  90
```

<210> SEQ ID NO 147
<211> LENGTH: 77
<212> TYPE: PRT
<213> ORGANISM: Homo sapiens

<400> SEQUENCE: 147

```
Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75
```

<210> SEQ ID NO 148
<211> LENGTH: 77
<212> TYPE: PRT
<213> ORGANISM: Macaca fascicularis

<400> SEQUENCE: 148

```
Ile Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Pro
            20                  25                  30

Ser Gln Phe Cys Pro His Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75
```

```
<210> SEQ ID NO 149
<211> LENGTH: 77
<212> TYPE: PRT
<213> ORGANISM: Macaca mulatta

<400> SEQUENCE: 149

Ile Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Pro
            20                  25                  30

Ser Gln Phe Cys Pro His Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Arg Ser Lys Arg Ser Pro
65                  70                  75

<210> SEQ ID NO 150
<211> LENGTH: 77
<212> TYPE: PRT
<213> ORGANISM: Oryctolagus cuniculus

<400> SEQUENCE: 150

Met Pro Leu Ser Arg Thr Val Arg Cys Thr Cys Ile Asn Ile Ser Asn
1               5                   10                  15

Lys Pro Val Asn Pro Arg Ser Leu Glu Lys Leu Glu Ile Ile Pro Ala
            20                  25                  30

Ser Gln Ser Cys Ala Asn Val Glu Ile Ile Ala Thr Met Lys Lys Asp
        35                  40                  45

Gly Glu Lys Arg Cys Leu Asn Pro Glu Leu Lys Ala Ile Lys Lys Leu
    50                  55                  60

Leu Lys Ala Phe Ser Lys Glu Arg Ser Arg Gly Ser Ser
65                  70                  75

<210> SEQ ID NO 151
<211> LENGTH: 77
<212> TYPE: PRT
<213> ORGANISM: Canis familiaris

<400> SEQUENCE: 151

Ile Pro Leu Ser Arg Thr Ile Arg Cys Thr Cys Ile Lys Ile Ser Asp
1               5                   10                  15

Gln Pro Val Asn Leu Arg Ser Leu Glu Lys Ile Glu Met Ile Pro Ala
            20                  25                  30

Ser Pro Ser Cys Pro His Val Glu Ile Ile Ala Thr Met Lys Lys Ser
        35                  40                  45

Gly Glu Lys Arg Cys Leu Asn Pro Glu Ser Lys Thr Ile Lys Ser Leu
    50                  55                  60

Val Lys Ala Ile Ser Lys Lys Arg Ser Arg Arg Ser Pro
65                  70                  75

<210> SEQ ID NO 152
<211> LENGTH: 83
<212> TYPE: PRT
<213> ORGANISM: Sus scrofa

<400> SEQUENCE: 152

Ile Pro Leu Ser Arg Thr Val Arg Cys Thr Cys Ile Lys Ile Ser Asp
1               5                   10                  15

Arg Pro Val Asn Pro Arg Ser Leu Glu Lys Leu Glu Met Ile Pro Ala
```

```
                    20                  25                  30

Ser Gln Ser Cys Pro His Val Glu Ile Ile Ala Thr Met Lys Lys Asn
            35                  40                  45

Gly Glu Lys Arg Cys Leu Asn Pro Glu Ser Lys Ala Ile Lys Asn Leu
        50                  55                  60

Leu Lys Ala Ile Ser Lys Glu Arg Ser Lys Arg Ser Pro Arg Thr Gln
65                  70                  75                  80

Arg Glu Ala

<210> SEQ ID NO 153
<211> LENGTH: 77
<212> TYPE: PRT
<213> ORGANISM: Rattus norvegicus

<400> SEQUENCE: 153

Ile Pro Leu Ala Arg Thr Val Arg Cys Thr Cys Ile Asp Phe His Glu
1               5                   10                  15

Gln Thr Leu Arg Pro Arg Ala Ile Gly Lys Leu Glu Ile Ile Pro Ala
            20                  25                  30

Ser Leu Ser Cys Pro His Val Glu Ile Ile Ala Thr Met Lys Lys Asn
        35                  40                  45

Asn Glu Lys Arg Cys Leu Asn Pro Glu Ser Glu Ala Ile Lys Ser Leu
    50                  55                  60

Leu Lys Ala Val Ser Gln Arg Ser Lys Arg Ala Pro
65                  70                  75

<210> SEQ ID NO 154
<211> LENGTH: 77
<212> TYPE: PRT
<213> ORGANISM: Mus musculus

<400> SEQUENCE: 154

Ile Pro Leu Ala Arg Thr Val Arg Cys Asn Cys Ile His Ile Asp Asp
1               5                   10                  15

Gly Pro Val Arg Met Arg Ala Ile Gly Lys Leu Glu Ile Ile Pro Ala
            20                  25                  30

Ser Leu Ser Cys Pro Arg Val Glu Ile Ile Ala Thr Met Lys Lys Asn
        35                  40                  45

Asp Glu Gln Arg Cys Leu Asn Pro Glu Ser Lys Thr Ile Lys Asn Leu
    50                  55                  60

Met Lys Ala Phe Ser Gln Lys Arg Ser Lys Arg Ala Pro
65                  70                  75

<210> SEQ ID NO 155
<211> LENGTH: 83
<212> TYPE: PRT
<213> ORGANISM: Capra hircus

<400> SEQUENCE: 155

Ile Pro Leu Ser Arg Asn Thr Arg Cys Thr Cys Ile Glu Ile Ser Asn
1               5                   10                  15

Gly Ser Val Asn Pro Arg Ser Leu Glu Lys Leu Glu Leu Ile Pro Ala
            20                  25                  30

Ser Gln Ser Cys Pro Arg Val Glu Ile Ile Ala Thr Met Lys Arg Asn
        35                  40                  45

Gly Glu Lys Arg Cys Leu Asn Pro Glu Ser Lys Thr Ile Lys Asn Leu
    50                  55                  60

Leu Lys Ala Ile Asn Lys Gln Arg Thr Lys Arg Ser Pro Arg Thr Arg
```

```
<210> SEQ ID NO 156
<211> LENGTH: 73
<212> TYPE: PRT
<213> ORGANISM: Sigmodon hispidus

<400> SEQUENCE: 156

Ile Pro His Ser Arg Thr Val Arg Cys Phe Cys Asn Lys Thr Glu Asp
1               5                   10                  15
Arg Leu Leu Arg Pro Arg Ala Leu Glu Lys Leu Glu Ile Ile Pro Ala
            20                  25                  30
Ser Leu Ser Cys Pro Arg Met Glu Ile Ile Ala Thr Met Lys Lys Thr
        35                  40                  45
Glu Lys Lys Arg Cys Leu Asn Pro Glu Ser Ala Ala Ile Lys Asn Leu
    50                  55                  60
Leu Lys Glu Ile Ser Arg Lys Asn Val
65                  70

<210> SEQ ID NO 157
<211> LENGTH: 77
<212> TYPE: PRT
<213> ORGANISM: Cricetus cricetus

<400> SEQUENCE: 157

Ile Pro Leu Ser Arg Thr Val Arg Cys Ser Cys Ile Lys Ile Asp Asp
1               5                   10                  15
Arg Pro Val Lys Pro Arg Ala Leu Gly Lys Leu Glu Ile Ile Pro Ala
            20                  25                  30
Ser Gln Ser Cys Pro Arg Val Glu Ile Ile Val Thr Met Lys Lys Thr
        35                  40                  45
Glu Glu Lys Arg Cys Leu Asn Pro Glu Ser Gly Ala Ile Lys Ser Leu
    50                  55                  60
Leu Lys Ala Val Ser Gln Arg Arg Ser Lys Arg Ala Ser
65                  70                  75

<210> SEQ ID NO 158
<211> LENGTH: 11
<212> TYPE: PRT
<213> ORGANISM: Artificial Sequence
<220> FEATURE:
<223> OTHER INFORMATION: chemically synthesized

<400> SEQUENCE: 158

Asn Ser Arg Asp Ser Ser Gly Asn His Val Leu
1               5                   10
```